(12) United States Patent
Barouch et al.

(10) Patent No.: US 11,059,863 B2
(45) Date of Patent: *Jul. 13, 2021

(54) STABILIZED HUMAN IMMUNODEFICIENCY VIRUS (HIV) ENVELOPE (ENV) TRIMER VACCINES AND METHODS OF USING SAME

(71) Applicant: Beth Israel Deaconess Medical Center, Inc., Boston, MA (US)

(72) Inventors: Dan H. Barouch, Newton, MA (US); Joseph Patrick Nkolola, Watertown, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,573

(22) Filed: Nov. 1, 2018

(65) Prior Publication Data

US 2019/0055290 A1 Feb. 21, 2019

Related U.S. Application Data

(60) Continuation of application No. 15/897,554, filed on Feb. 15, 2018, now Pat. No. 10,160,788, which is a division of application No. 14/149,549, filed on Jan. 7, 2014, now Pat. No. 9,932,370.

(60) Provisional application No. 61/749,737, filed on Jan. 7, 2013.

(51) Int. Cl.
| | |
|---|---|
| C07K 14/16 | (2006.01) |
| C07K 14/005 | (2006.01) |
| A61K 39/21 | (2006.01) |
| A61K 39/12 | (2006.01) |
| A61K 39/00 | (2006.01) |

(52) U.S. Cl.
CPC ............ *C07K 14/005* (2013.01); *A61K 39/12* (2013.01); *A61K 39/21* (2013.01); *C07K 14/162* (2013.01); *A61K 2039/55505* (2013.01); *A61K 2039/55561* (2013.01); *A61K 2039/55566* (2013.01); *C12N 2740/16034* (2013.01); *C12N 2740/16111* (2013.01); *C12N 2740/16122* (2013.01); *C12N 2740/16134* (2013.01)

(58) Field of Classification Search
CPC .................. A61K 39/21; C07K 14/162; C12N 2740/16134; C12N 2740/16122; C12N 2740/16111
See application file for complete search history.

(56) References Cited

U.S. PATENT DOCUMENTS

| | | |
|---|---|---|
| 4,603,112 A | 7/1986 | Paoletti et al. |
| 5,639,649 A | 6/1997 | Almond et al. |
| 5,643,576 A | 7/1997 | Johnston et al. |
| 6,911,205 B2 | 6/2005 | Sodroski et al. |
| 7,592,014 B2 | 9/2009 | Binley et al. |
| 7,901,690 B2 | 3/2011 | Lu et al. |
| 7,939,083 B2 | 5/2011 | Dey et al. |
| 9,017,691 B2 | 4/2015 | Barouch et al. |
| 9,932,370 B2 * | 4/2018 | Barouch ................. A61P 31/18 |
| 2007/0298051 A1 | 12/2007 | Barouch et al. |
| 2011/0250220 A1 | 10/2011 | Dey et al. |
| 2012/0045472 A1 | 2/2012 | Harrison et al. |
| 2012/0076812 A1 | 3/2012 | Barouch et al. |
| 2013/0189754 A1 | 7/2013 | Parks et al. |
| 2014/0302080 A1 | 10/2014 | Barouch et al. |
| 2014/0348791 A1 | 11/2014 | Barouch et al. |
| 2015/0291935 A1 | 10/2015 | Barouch et al. |
| 2016/0024156 A1 | 1/2016 | Barouch et al. |

FOREIGN PATENT DOCUMENTS

| | | |
|---|---|---|
| CN | 102282175 A | 12/2011 |
| WO | 0119958 | 3/2001 |
| WO | 2004/044155 | 5/2004 |
| WO | 2006002079 | 1/2006 |
| WO | 2006020071 | 2/2006 |
| WO | 2006/040330 | 4/2006 |
| WO | 2007005934 | 1/2007 |
| WO | 2007/024941 A2 | 3/2007 |
| WO | 2007/104792 | 9/2007 |
| WO | 2007/149491 | 12/2007 |
| WO | 2008063331 | 5/2008 |
| WO | 2010/042942 A2 | 4/2010 |
| WO | 2010/059732 | 5/2010 |
| WO | 2012/030904 | 3/2012 |
| WO | 2013055908 | 4/2013 |
| WO | 2014047261 | 3/2014 |
| WO | 2015004158 A1 | 1/2015 |
| WO | 2015048770 | 4/2015 |

OTHER PUBLICATIONS

Gaschen et al, "Diversity Consideration in HIV-1 Vaccine Selection," Science, vol. 296, No. 5577, pp. 2354-2360 (Jun. 28, 2002).
Genbank Accession No. AF286227.1, "HIV-1 strain 97Za012 from South Africa, complete genome." Accessed Jan. 5, 2016.
GenBank Accession No. KC769514. Retrieved on Dec. 30, 2014 (2 pages).
Georgiev et al, "Delineating Antibody Recognition in Polyclonal Sera from Patterns of HIV-1 Isolate Neutralization," Science, vol. 340, No. 6133, pp. 751-756 (2013).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).

(Continued)

*Primary Examiner* — Jeffrey S Parkin
(74) *Attorney, Agent, or Firm* — Ice Miller LLP

(57) ABSTRACT

The invention features stabilized human immunodeficiency virus (HIV) envelope (Env) trimers. The invention also features vaccines, nucleic acids, and vectors to deliver and/or facilitate production of the stabilized HIV Env trimers. In addition, the invention features methods of making and using the stabilized HIV Env trimers of the invention.

21 Claims, 12 Drawing Sheets

Specification includes a Sequence Listing.

(56) References Cited

OTHER PUBLICATIONS

Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Gray et al, "Safety and Efficacy of the HVTN 503/Phambili Study: A Double-Blind Randomized Placebo-Controlled Test-of-Concept Study of a Clade-B-Based HIV-1 Vaccine in South Africa," Lancet Infectious Diseases, vol. 11, No. 7, pp. 507-515 (Jul. 2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Hammer et al, "Efficacy Trial of a DNA/rAd5 HIV-1 Preventive Vaccine," The New England Journal of Medicine, vol. 369, No. 22, pp. 2083-2092 (Nov. 28, 2013).
Haynes et al, "Immune-Correlates Analysis of an HIV-1 Vaccine Efficacy Trial," The New England Journal of Medicine, vol. 366, No. 14, pp. 1275-1286 (Apr. 5, 2012).
Huang et al, "Broad and Potent Neutralization of HIV-1 by a gp41-Specific Human Antibody," Nature, vol. 491, No. 7424, pp. 406-412 (2012).
Int'l Preliminary Report on Patentability dated Apr. 5, 2016 in Int'l Application No. PCT/US2014/059093.
Int'l Preliminary Report on Patentability dated Jul. 7, 2015 in Int'l Application No. PCT/US2014/010543.
Int'l Preliminary Search Report on Patentability dated Apr. 12, 2011 in Int'l Application No. PCT/US2009/060494.
Int'l Search Report and Written Opinion dated Jan. 22, 2015 in Int'l Patent Application No. PCT/US2014/059093.
Int'l Search Report and Written Opinion dated Apr. 23, 2010 in Int'l Application No. PCT/US2009/060494.
Int'l Search Report dated Mar. 21, 2014 in Int'l Application No. PCT/US2014/010543.
Jeffs et al, "Expression and Characterization of Recombinant Oligomeric Envelope Glycoproteins Derived From Primary Isolates of HIV-1," Vaccine, vol. 22, No. 8, pp. 1032-1046 (2004).
Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).
Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).
Kang et al, "Structural and Immunogenicity Studies of a Cleaved, Stabilized Envelope Trimer Derived from Subtype A HIV-1," Vaccine, vol. 27, pp. 5120-5132 (2009).
Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).
Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).
Kothe et al, "Ancestral and Consensus Envelope Immunogens for HIV-1 Subtype C," Virology, vol. 352, No. 2, pp. 438-449 (2006).
Kothe et al, "Antigenicity and Immunogenicity of HIV-1 Consensus Subtype B Envelope Glycoproteins," Virology, vol. 360, No. 1, pp. 218-234 (Mar. 30, 2007).
Kovacs et al, "HIV-1 Envelope Trimer Elicits More Potent Neutralizing Antibody Responses than Monomeric gp120," Proceedings of the National Academy of Sciences of the United States of America, vol. 109, No. 30, pp. 12111-12116 (Jul. 24, 2012).

Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).
Lee et al, "A Single Point Mutation in HIV-1 V3 Loop Alters the Immunogenic Properties of rgp120," Archives of Virology, vol. 145, pp. 2087-2103 (2000).
Levine, "Why Do We Not Yet Have a Human Immunodeficiency Virus Vaccine," J. Virol., vol. 82, No. 24, pp. 11998-12000 (Dec. 2008).
Li et al, "Broad HIV-1 Neutralization Mediated by CD4-Binding Site Antibodies," Nature Medicine, vol. 13, No. 9, pp. 1032-1039 (Sep. 2007).
Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).
Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).
Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).
Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).
Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).
Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).
Liao et al, "Co-Evolution of a Broadly Neutralizing HIV-1 Antibody and Founder Virus," Nature, vol. 496, No. 7446, pp. 469-476 (Apr. 25, 2013).
Lin et al, "Designing Immunogens to Elicit Broadly Neutralizing Antibodies to the HIV-1 Envelope Glycoprotein," Current HIV Research, vol. 5, No. 6, pp. 514-541 (2007).
Li et al, "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).
Lynch et al, "The Development of CD4 Binding Site Antibodies During HIV-1 Infection," Journal of Virology, vol. 86, No. 14, pp. 7588-7595 (Jul. 2012).
Malherbe et al, "Sequential Immunization with a Subtype B HIV-1 Envelope Quasispecies Partially Mimics the In Vivo Development of Neutralizing Antibodies," Journal of Virology, vol. 85, No. 11, pp. 5262-5274 (Jun. 2011).
Mangeat et al, "Lentiviral Vectors and Antiretroviral Intrinsic Immunity," Human Gene Therapy, vol. 16, No. 8, pp. 913-920 (Aug. 2005).
Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).
Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).
McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).
McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).

(56) References Cited

OTHER PUBLICATIONS

McCoy et al, "Potent and Broad Neutralization of HIV-1 by a Llama Antibody Elicited by Immunization," The Journal of Experimental Medicine, vol. 209, No. 6, pp. 1091-1103 (2012).
McElrath et al, "Induction of Immunity to Human Immunodeficiency Virus Type-1 by Vaccination," Immunity, vol. 33, pp. 542-554 (Oct. 29, 2010).
McGuire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vaine et al, "Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Vogel et al, "The Majority of Neutralizing Abs in HIV-1-Infected Patients Recognize Linear V3 Loop Sequences," The Journal of Immunology, vol. 153, pp. 1895-1904 (1994).
Walker et al, "Broad and Potent Neutralizing Antibodies from an African Donor Reveal a New HIV-1 Vaccine D Target," Science, vol. 326, Oct. 9, 2009.
Walker et al, "Broad and Potent Neutralizing Antibodies from an African Donor Reveal a New HIV-1 Vaccine Target," Science, vol. 326, No. 5950, pp. 285-289 (Oct. 9, 2009).
Walker et al, "Broad Neutralization Coverage of HIV by Multiple Highly Potent Antibodies," Nature, vol. 477, No. 7365, pp. 466-470 (Sep. 22, 2011).
Walker et al, "Toward an AIDS Vaccine," Science, vol. 320, pp. 760-764 (May 9, 2008).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).
Wattanapitayakul et al, "Recent Developments in Gene Therapy for Cardiac Disease," Biomed & Pharmacother, vol. 54, No. 1, pp. 487-504 (2000).
Wiznerowicz et al, "Harnessing HIV for Therapy, Basic Research and Biotechnology," Trends in Biotechnology, vol. 23, No. 1, pp. 42-47 (Jan. 2005).
Written Opinion dated Mar. 21, 2014 in Int'l Application No. PCT/US2014/010543.
Wu et al, "Rational Design of Envelope Identifies Broadly Neutralizing Human Monoclonal Antibodies to HIV-1," Science, vol. 329, No. 5993, pp. 856-861 (Aug. 13, 2010).
Wyatt et al, "The Antigenic Structure of the HIV gp120 Envelope Glycoprotein," Nature, vol. 393, pp. 705-711 (Jun. 18, 1998).

Yang et al, "Highly Stable Trimers Formed by Human Immunodeficiency Virus Type 1 Envelope Glycoproteins Fused with the Trimeric Motif of T4 Bacteriophage Fibritin," Journal of Virology, vol. 76, No. 9, pp. 4634-4642 (May 2002).
Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).
Yang et al, "Modifications That Stabilize Human Immunodeficiency Virus Envelope Glycoprotein Trimers in Solution," Journal of Virology, vol. 74, No. 10, pp. 4746-4754 (2000).
Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).
Zhang et al, "Expression, Purification, and Characterization of Recombinant HIV gp140. The gp41 Ectodomain of HIV or Simian Immunodeficiency Virus is Sufficient to Maintain the Retroviral Envelope Glycoprotein as a Trimer," The Journal of Biological Chemistry, vol. 276, No. 43, pp. 39577-39585 (Oct. 26, 2001).
Zhang et al, "Extensively Cross-Reactive Anti-HIV-1 Neutralizing Antibodies Induced by gp140 Immunization," PNAS, vol. 104, No. 24, pp. 10193-10198 (2007).
Zhou et al, "Structural Basis for Broad and Potent Neutralization of HIV-1 by Antibody VRC01," Science, vol. 329, No. 5993, pp. 811-817 (Aug. 13, 2010).
Zolla-Pazner et al, "Focusing the Immune Response on the V3 Loop, a Neutralizing Epitope of the HIV-1 gp210 Envelope," Virology, vol. 372, pp. 233-246 (2008).
McClellan et al, "Structure of HIV-1 gp120 V1/V2 Domain with Broadly Neutralizing Antibody PG9," Nature, vol. 480, No. 7377, pp. 336-343 (2011).
Montefiori et al, "Antibody-Based HIV-1 Vaccines: Recent Developments and Future Directions," PLOS Medicine, vol. 4, No. 12, pp. e348 (2007).
Montefiori, "Evaluating Neutralizing Antibodies Against HIV, SIV, and SHIV in Luciferase Reporter Gene Assays," Current Protocols in Immunology, vol. 12, No. 11, pp. 1-17 (2004).
Montefiori, "Measuring HIV Neutralization in a Luciferase Reporter Gene Assay," HIV Protocols Second 25 Edition, vol. 485, pp. 395-405 (2009).
Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).
Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
Nkolola et al, "Breadth Of Neutralizing Antibodies Elicited By Stable, Homogenous Clade And Clade C HIV-1 gp140 Envelope Trimers In Guinea Pigs," Journal of Virology, vol. 84, No. 7, pp. 3270-3279 (Apr. 2010).
Nkolola et al, "Characterization and Immunogenicily of a Novel Mosaic M HIV-1 gp140 Trimer," Journal of Virology, vol. 88, No. 17, pp. 9538-9552 (2014).
Nkolola et al, "Stability and Neutralization Capacity of a Novel Mosaic HIV-1 gp140 trimer in a Guinea Pig Model" AIDS Vaccine Poster, Ragon Institute, 1 pg. (2012).
Nkolola et al, "Stability and Neutralization Capacity of a Novel Mosaic HIV-1 gp140 Trimer in a Guinea Pig Model," Retrovirology, vol. 9, Supp. 2, pp. 299 (2012).
Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).
Page et al, "Studies on the Immunogenicity of Chinese Hamster Ovary Cell-Derived Recombinant gp120 (HIV-1111B)," Vaccine, vol. 9, pp. 47-52 (Jan. 1991).

(56) References Cited

OTHER PUBLICATIONS

Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pantophlet et al, "GP120: Target for Neutralizing HIV-1 Antibodies," Annu. Rev. Immunol., vol. 24, pp. 739-769 (2006).
Pejchal et al, "A Potent and Broad Neutralizing Antibody Recognizes and Penetrates the HIV Glycan Shield," Science, vol. 334, No. 6059, pp. 1097-1103 (2011).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).
Pinter, "Roles of HIV-1 Env Variable Regions in Viral Neutralization and Vaccine Development," Current HIV Research, vol. 5, No. 6, pp. 542-553 (2007).
Pitisuttithum et al, "Randomized, Double-Bind, Placebo-Controlled Efficacy Trial of a Bivalent Recombinant Glycoprotein 120 HIV-1 Vaccine Among Injection Drug Users in Bangkok, Thailand," The Journal of Infectious Diseases, vol. 194, pp. 1661-1671 (2006).
Plotkin et al, "Postscript Relating to New Allegations Made by Edward Hooper at The Royal Society Discussion Meeting on Sep. 11, 2000," Philosophical Transactions of the Royal Society of London B: Biological Sciences, vol. 356, No. 1410, pp. 825-829 (2001).
Plotkin, "Correlates of Protection Induced by Vaccination," Clinical and Vaccine Immunology, vol. 17, No. 7, pp. 1055-1065 (Jul. 2010).
Plotkin, "Immunologic Correlates of Protection Induced by Vaccination," Pediatric Infectious Disease Journal, vol. 20, No. 1, pp. 63-75 (2001).
Plotkin, "The RV144 Thai HIV Vaccine Trial," Human Vaccines, vol. 6, No. 2, p. 159 (Feb. 2010).
Polonis et al, "Recent Advances in the Characterization of HIV-1 Neutralization Assays for Standardized Evaluation of the Antibody Response to Infection and Vaccination," Virology, vol. 375, pp. 315-320 (2008).
Rerks-Ngarm et al, "Vaccination with ALVAC and AIDSVAX to Prevent HIV-1 Infection in Thailand," The New England Journal of Medicine, vol. 361, No. 23, pp. 222-233 (Dec. 3, 2009).
Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).
Santra et al, "Mosaic Vaccines Elicit CD8+ T Lymphocyte Responses in Monkeys that Confer Enhanced Immune Coverage of Diverse HIV Strains," Nature Medicine, vol. 16, No. 3, pp. 324-328 (Mar. 2010).
Saphire et al, "Crystal Structure of a Neutralizing Human IgG Against HIV-1: A Template for Vaccine Design," Science, vol. 293, No. 5532, pp. 1155-1159 (2001).
Sattentau, "Envelope Glycoprotein Trimers as HIV-1 Vaccine Immunogens", Vaccines, vol. 1, pp. 497-512 (2013).
Scheid et al, "Broad Diversity of Neutralizing Antibodies Isolated From Memory B Cells in HIV-Infected Individuals," D Nature, vol. 458, pp. 636-640 (Apr. 2, 2009).
Scheid et al, "Sequence and Structural Convergence of Broad and Potent HIV Antibodies That Mimic CD4 Binding," Science, vol. 333, pp. 1633-1637 (2011).

Seaman et al, "Standardized Assessment of NAb Responses Elicited in Rhesus Monkeys Immunized with Single- or Multi-Glade HIV-1 Envelope Immunogens," Virology, vol. 367, pp. 175-186 (2007).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Stamatatos et al, "Neutralizing Antibodies Generated During Natural HIV-1 Infection: Good News for an HIV-1 Vaccine?," Nature Medicine, vol. 15, No. 8, pp. 866-870 (2009).
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Amanna et al, "Contributions of Humoral and Cellular Immunity to Vaccine-Induced Protection in Humans," Virology, vol. 411, No. 2, pp. 206-215 (2011).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Barnett et al, "Development of V2-deleted trimeric envelope vaccine candidates from human immunodeficiency virus type 1 (HIV-1) subtypes B and C," Microbes Infect., vol. 7, vol. 14, pp. 1386-1391 (2005).
Barouch et al, "Mosaic HIV-1 Vaccines Expand the Breadth and Depth of Cellular Immune Responses in Rhesus Monkeys," Nature Medicine, vol. 16, No. 3, pp. 319-323 (Mar. 2010).
Barouch, "Challenges in the Development of an HIV-1 Vaccine," Nature, vol. 455, pp. 613-619 (Oct. 2008).
Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric gp120," Virology, vol. 360, pp. 329-340 (2007).
Berger et al, "Chemokine Receptors as HIV-1 Coreceptors: Roles in Viral Entry, Tropism and Disease," Annu. Rev. Immunol., vol. 17, pp. 657-700 (1999).
Berman et al, "Comparison of the Immune Response to Recombinant gp120 in Humans and Chimpanzees," AIDS, vol. 8, pp. 591-601 (1994).
Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Bower et al, "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).
Bower et al, "HIV-1 ENV gp 140 Trimers Elicit Neutralizing Antibodies Without Efficient Induction of Conformational Antibodies," Vaccine, vol. 24, pp. 5442-5451 (2006).
Buchbinder et al, "Efficacy Assessment of a Cell-Mediated Immunity HIV-1 Vaccine (The Step Study): A Double-Blind, Randomised, Placebo-Controlled, Test-of-Concept Trial," Lancet, vol. 372, No. 9653, pp. 1881-1893 (Nov. 29, 2008).
Burke et al, "Neutralizing Antibody Responses to Subtype B and C Adjuvanted HIV Envelope Protein Vaccination in Rabbits," Virology, vol. 387, pp. 147-155 (2009).

(56) References Cited

OTHER PUBLICATIONS

Burton et al, "HIV Vaccine Design and the Neutralizing Antibody Problem," Nature Immunology, vol. 5, No. 3, pp. 233-236 (Mar. 2004).
Calarese et al, "Antibody Domain Exchange is an Immunological Solution to Carbohydrate Cluster Recognition," Science, vol. 300, No. 5628, pp. 2065-2071 (2003).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Carrow et al, "High Prevalance of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Checkley et al, "HIV-1 Envelope Glycoprotein Biosynthesis, Trafficking, and Incorporation," Journal of Molecular Biology, vol. 410, No. 4, pp. 582-608 (2011).
Chen et al, "A Chimeric Protein of Simian Immunodeficiency Virus Envelope Glycoprotein gp140 and *Escherichia coli* Aspartate Transcarbamoylase," Journal of Virology, vol. 78, No. 9, pp. 4508-4516 (May 2004).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Cohen, "Naked DNA Points Way to Vaccines," Science, vol. 259, pp. 1691-1692 (Mar. 1993).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
Derby et al, "Isolation and Characterization of Monoclonal Antibodies Elicited by Trimeric HIV-1 ENV gp140 Protein 14 Immunogens," Virology, vol. 366, pp. 433-445 (2007).
Desrosiers, "Prospects for an AIDS Vaccine", Nature Medicine, vol. 10, No. 3, pp. 221-223 (2004).
Dey et al, "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).
Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).
Fischer et al, "Identification of a Peptide Mimicking the Binding Pattern of an Antiphospholipid Antibody," Immunobiology, vol. 211, No. 9, pp. 695-699 (2006).
Fischer et al, "Polyvalent Vaccines for Optimal Coverage of Potential T-Cell Epitopes in Global HIV-1 Variants," Nature Medicine, vol. 13, No. 1, pp. 100-106 (2007).
Flynn et al, "Placebo-Controlled Phase 3 Trial of a Recombinant Glycoprotein 120 Vaccine to Prevent HIV-1 Infection," J. Infect. Dis., vol. 191, pp. 654-665 (2005).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Frey et al, "A Fusion-Intermediate State of HIV-1 gp41 Targeted by Broadly Neutralizing Antibodies," Proceedings of be National Academy of Sciences of the United States of America, vol. 105, No. 10, pp. 3739-3744 (Mar. 11, 2008).
Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).
Gallo et al, "The HIV Env-mediated Fusion Reaction," Biochemics et Biophysica Acta, pp. 36-50 (2003).
Gallo, "The End or the Beginning of the Drive to an HIV-Preventive Vaccine: A View from over 20 Years", The Lancet, vol. 366, No. 9500, pp. 1894-1898 (Nov. 2005).
Gao et al, "A Comprehensive Panel of Near-Full-Length Clones and Reference Sequences for Non-Subtype B Isolates of Human Immunodeficiency Virus Type 1, "Journal of Virology, vol. 72, No. 7, pp. 5680-5698 (1998).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gao et al, "Centralized HIV-1 Envelope Immunogens and Neutralizing Antibodies," Current HIV Research, vol. 5, No. 5, pp. 572-577 (2007).
Gao et al, "Molecular Cloning and Analysis of Functional Envelope Genes from Human Immunodeficiency Virus Type 1 Sequence Subtypes A through G" Journal of Virology, vol. 70, No. 3, pp. 1651-1667 (Mar. 1996).

\* cited by examiner

Figure 1A

Mosaic gp140 Env1 version 1 (mEnv) (SEQ ID NO: 1)

MRVTGIRKNYQHLWRWGTMLLGILMICSAAGKLWVTVYYGVPV
WKEATTTLFCASDAKAYDTEVHNVWATHACVPTDPNPQEVVLE
NVTENFNMWKNNMVEQMHEDIISLWDQSLKPCVKLTPLCVTLN
CTDDVRNVTNNATNTNSSWGEPMEKGEIKNCSFNITTSIRNKV
QKQYALFYKLDVVPIDNDSNNTNYRLISCNTSVITQACPKVSF
EPIPIHYCAPAGFAILKCNDKKFNGTGPCTNVSTVQCTHGIRP
VVSTQLLLNGSLAEEEVVIRSENFTNNAKTIMVQLNVSVEINC
TRPNNNTRKSIHIGPGRAFYTAGDIIGDIRQAHCNISRANWNN
TLRQIVEKLGKQFGNNKTIVFNHSSGGDPEIVMHSFNCGGEFF
YCNSTKLFNSTWTWNNSTWNNTKRSNDTEEHITLPCRIKQIIN
MWQEVGKAMYAPPIRGQIRCSSNITGLLLTRDGGNDTSGTEIF
RPGGGDMRDNWRSELYKYKVVKIEPLGVAPTKAKRRVVQSEKS
AVGIGAVFLGFLGAAGSTMGAASMTLTVQARLLLSGIVQQQNN
LLRAIEAQQHLLQLTVWGIKQLQARVLAVERYLKDQQLLGIWG
CSGKLICTTTVPWNASWSNKSLDKIWNNMTWMEWEREINNYTS
LIYTLIEESQNQQEKNEQELLELDKWASLWNWFDISNWLWGYI
PEAPRDGQAYVRKDGEWVLLSTFL

Boxed:        signal/leader sequence
Underlined:   gp120
Plain:        gp41 ectodomain
___:          T4-fibritin "foldon" trimerization domain

Figure 1B

Mosaic gp140 Env1 version 2 (mEnv+) (SEQ ID NO: 2)

MRVRGIQRNCQHLWRWGTLILGMLMICSAAGKLWVTVYYGVPV
WKEATTTLFCASDAKAYDTEVHNVWATHACVPTDPNPQEVVLE
NVTENFNMWKNNMVEQMHEDIISLWDQSLKPCVKLTPLCVTLN
CTDDVRNVTNNATNTNSSWGEPMEKGEIKNCSFNITTSIRNKV
QKQYALFYKLDVVPIDNDSNNTNYRLISCNTSVITQACPKVSF
EPIPIHYCAPAGFAILKCNDKKFNGTGPCTNVSTVQCTHGIRP
VVSTQLLLNGSLAEEEVVIRSENFTNNAKTIMVQLNVSVEINC
TRPNNNTRKSIHIGPGRAFYTAGDIIGDIRQAHCNISRANWNN
TLRQIVEKLGKQFGNNKTIVFNHSSGGDPEIVMHSFNCGGEFF
YCNSTKLFNSTWTWNNSTWNNTKRSNDTEEHITLPCRIKQIIN
MWQEVGKAMYAPPIRGQIRCSSNITGLLLTRDGGNDTSGTEIF
RPGGGDMRDNWRSELYKYKVVKIEPLGVAPTKAKERVVQRER
AVGIGAVFLGFLGAAGSTMGAASMTLTVQARLLLSGIVQQQNN
LLRAIEAQQHLLQLTVWGIKQLQARVLAVERYLKDQQLLGIWG
CSGKLICTTTVPWNASWSNKSLDKIWNNMTWMEWEREINNYTS
LIYTLIEESQNQQEKNEQELLELDKWASLWNWFDISNWLWYIK
SRIEGRGSGGYIPEAPRDGQAYVRKDGEWVLLSTFL

Boxed: signal/leader sequence
Underlined: gp120
Circled: cleavage site mutations
Plain: gp41 ectodomain
......: Factor Xa site
___: T4-fibritin "foldon" trimerization domain

Figure 1C clade C Env (cEnv) (SEQ ID NO: 3)

MRVRGIQRNCQHLWRWGTLILGMLMICSAAENLWVGNMWVTVY
YGVPVWTDAKTTLFCASDTKAYDREVHNVWATHACVPTDPNPQ
EIVLENVTENFNMWKNDMVDQMHEDIISLWDQSLKPCVKLTPL
CVTLHCTNATFKNNVTNDMNKEIRNCSFNTTTEIRDKKQQGYA
LFYRPDIVLLKENRNNSNNSEYILINCNASTITQACPKVNFDP
IPIHYCAPAGYAILKCNNKTFSGKGPCNNVSTVQCTHGIKPVV
STQLLLNGSLAEKEIIIRSENLTDNVKTIIVHLNKSVEIVCTR
PNNNTRKSMRIGPGQTFYATGDIIGDIRQAYCNISGSKWNETL
KRVKEKLQENYNNNKTIKFAPSSGGDLEITTHSFNCRGEFFYC
NTTRLFNNNATEDETITLPCRIKQIINMWQGVGRAMYAPPIAG
NITCKSNITGLLLVRDGGEDNKTEEIFRPGGGNMKDNWRSELY
KYKVIELKPLGIAPTGAKERVVEREERAVGIGAVFLGFLGAAG
STMGAASLTLTVQARQLLSSIVQQQSNLLRAIEAQQHMLQLTV
WGIKQLQTRVLAIERYLKDQQLLGIWGCSGKLICTTNVPWNSS
WSNKSQTDIWNNMTWMEWDREISNYTDTIYRLLEDSQTQQEKN
EKDLLALDSWKNLWSWFDISNWLWYIKSRIEGRGSGGYIPEAP
RDGQAYVRKDGEWVLLSTFL

Boxed:        signal/leader sequence
Underlined:   gp120
Circled:      cleavage site mutations
Plain:        gp41 ectodomain
⁓⁓⁓:          Factor Xa site
___:          T4-fibritin "foldon" trimerization domain

Clade A

Clade B

7A

7B

Clade B

7C

7D

Clade C

8A

8B

Clade C

8C

8D

SEQUENCE LISTING

```
<160> NUMBER OF SEQ ID NOS: 34

<210> SEQ ID NO 1
<211> LENGTH: 712
<212> TYPE: PRT
<213> ORGANISM: Artificial Sequence
<220> FEATURE:
<223> OTHER INFORMATION: Synthetic Construct (Mosaic gp140 Env1)

<400> SEQUENCE: 1

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
```

```
            180                 185                 190
Asn Thr Asn Tyr Arg Leu Ile Ser Cys Asn Thr Ser Val Ile Thr Gln
            195                 200                 205
Ala Cys Pro Lys Val Ser Phe Glu Pro Ile Pro Ile His Tyr Cys Ala
    210                 215                 220
Pro Ala Gly Phe Ala Ile Leu Lys Cys Asn Asp Lys Lys Phe Asn Gly
225                 230                 235                 240
Thr Gly Pro Cys Thr Asn Val Ser Thr Val Gln Cys Thr His Gly Ile
                245                 250                 255
Arg Pro Val Val Ser Thr Gln Leu Leu Leu Asn Gly Ser Leu Ala Glu
            260                 265                 270
Glu Val Val Ile Arg Ser Glu Asn Phe Thr Asn Ala Lys Thr
    275                 280                 285
Ile Met Val Gln Leu Asn Val Ser Val Glu Ile Asn Cys Thr Arg Pro
    290                 295                 300
Asn Asn Asn Thr Arg Lys Ser Ile His Ile Gly Pro Gly Arg Ala Phe
305                 310                 315                 320
Tyr Thr Ala Gly Asp Ile Ile Gly Asp Ile Arg Gln Ala His Cys Asn
                325                 330                 335
Ile Ser Arg Ala Asn Trp Asn Asn Thr Leu Arg Gln Ile Val Glu Lys
                340                 345                 350
Leu Gly Lys Gln Phe Gly Asn Asn Lys Thr Ile Val Phe Asn His Ser
            355                 360                 365
Ser Gly Gly Asp Pro Glu Ile Val Met His Ser Phe Asn Cys Gly Gly
    370                 375                 380
Glu Phe Phe Tyr Cys Asn Ser Thr Lys Leu Phe Asn Ser Thr Trp Thr
385                 390                 395                 400
Trp Asn Asn Ser Thr Trp Asn Asn Thr Lys Arg Ser Asn Asp Thr Glu
                405                 410                 415
Glu His Ile Thr Leu Pro Cys Arg Ile Lys Gln Ile Ile Asn Met Trp
                420                 425                 430
Gln Glu Val Gly Lys Ala Met Tyr Ala Pro Pro Ile Arg Gly Gln Ile
            435                 440                 445
Arg Cys Ser Ser Asn Ile Thr Gly Leu Leu Leu Thr Arg Asp Gly Gly
    450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Arg Arg Val Val Gln
            500                 505                 510
Ser Glu Lys Ser Ala Val Gly Ile Gly Ala Val Phe Leu Gly Phe Leu
            515                 520                 525
Gly Ala Ala Gly Ser Thr Met Gly Ala Ala Ser Met Thr Leu Thr Val
            530                 535                 540
Gln Ala Arg Leu Leu Leu Ser Gly Ile Val Gln Gln Asn Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Ala Arg Val Leu Ala Val Glu Arg Tyr Leu
            580                 585                 590
Lys Asp Gln Gln Leu Leu Gly Ile Trp Gly Cys Ser Gly Lys Leu Ile
            595                 600                 605
```

```
Cys Thr Thr Thr Val Pro Trp Asn Ala Ser Trp Ser Asn Lys Ser Leu
            610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
            645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp Gly Tyr Ile
            675                 680                 685

Pro Glu Ala Pro Arg Asp Gly Gln Ala Tyr Val Arg Lys Asp Gly Glu
            690                 695                 700

Trp Val Leu Leu Ser Thr Phe Leu
705                 710

<210> SEQ ID NO 2
<211> LENGTH: 724
<212> TYPE: PRT
<213> ORGANISM: Artificial Sequence
<220> FEATURE:
<223> OTHER INFORMATION: Synthetic Construct (Optimized mosaic gp140
      Env1)

<400> SEQUENCE: 2

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Gly Lys
            20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
        130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
```

```
                    245                 250                 255
Arg Pro Val Val Ser Thr Gln Leu Leu Leu Asn Gly Ser Leu Ala Glu
                260                 265                 270

Glu Glu Val Val Ile Arg Ser Glu Asn Phe Thr Asn Asn Ala Lys Thr
            275                 280                 285

Ile Met Val Gln Leu Asn Val Ser Val Glu Ile Asn Cys Thr Arg Pro
        290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
        355                 360                 365

Ser Gly Gly Asp Pro Glu Ile Val Met His Ser Phe Asn Cys Gly Gly
    370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Leu Leu Thr Arg Asp Gly Gly
    450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Glu Arg Val Val Gln
            500                 505                 510

Arg Glu Glu Arg Ala Val Gly Ile Gly Ala Val Phe Leu Gly Phe Leu
        515                 520                 525

Gly Ala Ala Gly Ser Thr Met Gly Ala Ala Ser Met Thr Leu Thr Val
    530                 535                 540

Gln Ala Arg Leu Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
        595                 600                 605

Cys Thr Thr Thr Val Pro Trp Asn Ala Ser Trp Ser Asn Lys Ser Leu
    610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
            660                 665                 670
```

```
Ser Leu Trp Asn Trp Phe Asp Ile Ser Asn Trp Leu Trp Tyr Ile Lys
        675                 680                 685

Ser Arg Ile Glu Gly Arg Gly Ser Gly Gly Tyr Ile Pro Glu Ala Pro
    690                 695                 700

Arg Asp Gly Gln Ala Tyr Val Arg Lys Asp Gly Glu Trp Val Leu Leu
705                 710                 715                 720

Ser Thr Phe Leu

<210> SEQ ID NO 3
<211> LENGTH: 708
<212> TYPE: PRT
<213> ORGANISM: Artificial Sequence
<220> FEATURE:
<223> OTHER INFORMATION: Synthetic Construct (Optimized clade C gp140
      Env)

<400> SEQUENCE: 3

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Gly Asn Met Trp Val Thr Val Tyr Tyr Gly Val Pro Val
        35                  40                  45

Trp Thr Asp Ala Lys Thr Thr Leu Phe Cys Ala Ser Asp Thr Lys Ala
50                  55                  60

Tyr Asp Arg Glu Val His Asn Val Trp Ala Thr His Ala Cys Val Pro
65                  70                  75                  80

Thr Asp Pro Asn Pro Gln Glu Ile Val Leu Glu Asn Val Thr Glu Asn
                85                  90                  95

Phe Asn Met Trp Lys Asn Asp Met Val Asp Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu His Cys Thr Asn Ala Thr Phe Lys Asn Asn Val
130                 135                 140

Thr Asn Asp Met Asn Lys Glu Ile Arg Asn Cys Ser Phe Asn Thr Thr
145                 150                 155                 160

Thr Glu Ile Arg Asp Lys Lys Gln Gln Gly Tyr Ala Leu Phe Tyr Arg
                165                 170                 175

Pro Asp Ile Val Leu Leu Lys Glu Asn Arg Asn Asn Ser Asn Asn Ser
            180                 185                 190

Glu Tyr Ile Leu Ile Asn Cys Asn Ala Ser Thr Ile Thr Gln Ala Cys
        195                 200                 205

Pro Lys Val Asn Phe Asp Pro Ile Pro Ile His Tyr Cys Ala Pro Ala
210                 215                 220

Gly Tyr Ala Ile Leu Lys Cys Asn Asn Lys Thr Phe Ser Gly Lys Gly
225                 230                 235                 240

Pro Cys Asn Asn Val Ser Thr Val Gln Cys Thr His Gly Ile Lys Pro
                245                 250                 255

Val Val Ser Thr Gln Leu Leu Asn Gly Ser Leu Ala Glu Lys Glu
            260                 265                 270

Ile Ile Ile Arg Ser Glu Asn Leu Thr Asp Asn Val Lys Thr Ile Ile
        275                 280                 285

Val His Leu Asn Lys Ser Val Glu Ile Val Cys Thr Arg Pro Asn Asn
290                 295                 300
```

```
Asn Thr Arg Lys Ser Met Arg Ile Gly Pro Gly Gln Thr Phe Tyr Ala
305                 310                 315                 320

Thr Gly Asp Ile Ile Gly Asp Ile Arg Gln Ala Tyr Cys Asn Ile Ser
                325                 330                 335

Gly Ser Lys Trp Asn Glu Thr Leu Lys Arg Val Lys Glu Lys Leu Gln
            340                 345                 350

Glu Asn Tyr Asn Asn Asn Lys Thr Ile Lys Phe Ala Pro Ser Ser Gly
        355                 360                 365

Gly Asp Leu Glu Ile Thr Thr His Ser Phe Asn Cys Arg Gly Glu Phe
    370                 375                 380

Phe Tyr Cys Asn Thr Thr Arg Leu Phe Asn Asn Asn Ala Thr Glu Asp
385                 390                 395                 400

Glu Thr Ile Thr Leu Pro Cys Arg Ile Lys Gln Ile Ile Asn Met Trp
                405                 410                 415

Gln Gly Val Gly Arg Ala Met Tyr Ala Pro Pro Ile Ala Gly Asn Ile
            420                 425                 430

Thr Cys Lys Ser Asn Ile Thr Gly Leu Leu Leu Val Arg Asp Gly Gly
        435                 440                 445

Glu Asp Asn Lys Thr Glu Glu Ile Phe Arg Pro Gly Gly Gly Asn Met
    450                 455                 460

Lys Asp Asn Trp Arg Ser Glu Leu Tyr Lys Tyr Lys Val Ile Glu Leu
465                 470                 475                 480

Lys Pro Leu Gly Ile Ala Pro Thr Gly Ala Lys Glu Arg Val Val Glu
                485                 490                 495

Arg Glu Glu Arg Ala Val Gly Ile Gly Ala Val Phe Leu Gly Phe Leu
            500                 505                 510

Gly Ala Ala Gly Ser Thr Met Gly Ala Ala Ser Leu Thr Leu Thr Val
        515                 520                 525

Gln Ala Arg Gln Leu Leu Ser Ser Ile Val Gln Gln Gln Ser Asn Leu
    530                 535                 540

Leu Arg Ala Ile Glu Ala Gln Gln His Met Leu Gln Leu Thr Val Trp
545                 550                 555                 560

Gly Ile Lys Gln Leu Gln Thr Arg Val Leu Ala Ile Glu Arg Tyr Leu
                565                 570                 575

Lys Asp Gln Gln Leu Leu Gly Ile Trp Gly Cys Ser Gly Lys Leu Ile
            580                 585                 590

Cys Thr Thr Asn Val Pro Trp Asn Ser Ser Trp Ser Asn Lys Ser Gln
        595                 600                 605

Thr Asp Ile Trp Asn Asn Met Thr Trp Met Glu Trp Asp Arg Glu Ile
    610                 615                 620

Ser Asn Tyr Thr Asp Thr Ile Tyr Arg Leu Leu Glu Asp Ser Gln Thr
625                 630                 635                 640

Gln Gln Glu Lys Asn Glu Lys Asp Leu Leu Ala Leu Asp Ser Trp Lys
                645                 650                 655

Asn Leu Trp Ser Trp Phe Asp Ile Ser Asn Trp Leu Trp Tyr Ile Lys
            660                 665                 670

Ser Arg Ile Glu Gly Arg Gly Ser Gly Gly Tyr Ile Pro Glu Ala Pro
        675                 680                 685

Arg Asp Gly Gln Ala Tyr Val Arg Lys Asp Gly Glu Trp Val Leu Leu
    690                 695                 700

Ser Thr Phe Leu
705
```

<210> SEQ ID NO 4
<211> LENGTH: 684
<212> TYPE: PRT
<213> ORGANISM: Artificial Sequence
<220> FEATURE:
<223> OTHER INFORMATION: Synthetic Construct (Mosaic gp140 Env2)

<400> SEQUENCE: 4

```
Met Arg Val Arg Gly Ile Gln Arg Asn Trp Pro Gln Trp Trp Ile Trp
1               5                   10                  15

Gly Ile Leu Gly Phe Trp Met Ile Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110

Gln Ser Leu Lys Pro Cys Val Lys Leu Thr Pro Leu Cys Val Thr Leu
        115                 120                 125

Glu Cys Arg Asn Val Arg Asn Val Ser Ser Asn Gly Thr Tyr Asn Ile
    130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365
```

```
Thr Ser Ser Gly Gly Asp Leu Glu Ile Thr Thr His Ser Phe Asn
    370             375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
                420                 425                 430

Arg Ala Met Tyr Ala Pro Pro Ile Ala Gly Asn Ile Thr Cys Arg Ser
            435                 440                 445

Asn Ile Thr Gly Leu Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Ser
            500                 505                 510

Glu Lys Ser Ala Val Gly Ile Gly Ala Val Phe Leu Gly Ile Leu Gly
    515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
    595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
    675                 680

<210> SEQ ID NO 5
<211> LENGTH: 678
<212> TYPE: PRT
<213> ORGANISM: Artificial Sequence
<220> FEATURE:
<223> OTHER INFORMATION: Synthetic Construct (Mos3 gp140 Env)

<400> SEQUENCE: 5

Met Arg Val Lys Gly Ile Arg Lys Asn Tyr Gln His Leu Trp Lys Trp
1               5                   10                  15

Gly Thr Met Leu Leu Gly Met Leu Met Ile Cys Ser Ala Ala Glu Gln
                20                  25                  30

Leu Trp Val Thr Val Tyr Tyr Gly Val Pro Val Trp Arg Asp Ala Glu
            35                  40                  45
```

```
Thr Thr Leu Phe Cys Ala Ser Asp Ala Lys Ala Tyr Glu Arg Glu Val
 50                  55                  60
His Asn Ile Trp Ala Thr His Ala Cys Val Pro Thr Asp Pro Asn Pro
 65                  70                  75                  80
Gln Glu Ile Val Leu Glu Asn Val Thr Glu Glu Phe Asn Met Trp Lys
                 85                  90                  95
Asn Asp Met Val Glu Gln Met His Thr Asp Ile Ile Ser Leu Trp Asp
            100                 105                 110
Glu Ser Leu Lys Pro Cys Val Lys Leu Ala Pro Leu Cys Val Thr Leu
        115                 120                 125
Asn Cys Thr Asn Ala Asn Leu Asn Cys Thr Asn Asp Asn Cys Asn Arg
130                 135                 140
Thr Val Asp Lys Met Arg Glu Ile Lys Asn Cys Ser Phe Asn Met
145                 150                 155                 160
Thr Thr Glu Leu Arg Asp Lys Lys Gln Lys Val Tyr Ala Leu Phe Tyr
                165                 170                 175
Lys Leu Asp Ile Val Pro Ile Glu Lys Asn Ser Ser Glu Tyr Arg Leu
            180                 185                 190
Ile Asn Cys Asn Thr Ser Thr Ile Thr Gln Ala Cys Pro Lys Val Thr
        195                 200                 205
Phe Glu Pro Ile Pro Ile His Tyr Cys Thr Pro Ala Gly Phe Ala Ile
210                 215                 220
Leu Lys Cys Lys Asp Lys Lys Phe Asn Gly Thr Gly Pro Cys Lys Asn
225                 230                 235                 240
Val Ser Thr Val Gln Cys Thr His Gly Ile Lys Pro Val Ile Ser Thr
                245                 250                 255
Gln Leu Leu Leu Asn Gly Ser Leu Ala Glu Gly Glu Ile Ile Ile Arg
            260                 265                 270
Ser Glu Asn Ile Thr Asn Asn Ala Lys Thr Ile Ile Val Gln Leu Asn
        275                 280                 285
Glu Ser Val Val Ile Asn Cys Thr Arg Pro Gly Asn Asn Thr Arg Lys
290                 295                 300
Ser Val Arg Ile Gly Pro Gly Gln Ala Phe Tyr Ala Thr Gly Glu Ile
305                 310                 315                 320
Ile Gly Asp Ile Arg Gln Ala Tyr Cys Asn Ile Ser Arg Ala Lys Trp
                325                 330                 335
Asn Asn Thr Leu Lys Gln Ile Val Thr Lys Leu Lys Glu Gln Phe Lys
            340                 345                 350
Asn Lys Thr Ile Val Phe Asn Gln Ser Ser Gly Gly Asp Pro Glu Ile
        355                 360                 365
Thr Thr His Ser Phe Asn Cys Gly Gly Glu Phe Phe Tyr Cys Asn Thr
370                 375                 380
Thr Gln Leu Phe Asn Ser Thr Trp Asn Ser Asn Ser Thr Trp Asn Asp
385                 390                 395                 400
Thr Thr Gly Ser Val Thr Glu Gly Asn Asp Thr Ile Thr Leu Pro Cys
                405                 410                 415
Arg Ile Lys Gln Ile Val Asn Met Trp Gln Arg Val Gly Gln Ala Met
            420                 425                 430
Tyr Ala Pro Pro Ile Glu Gly Asn Ile Thr Cys Lys Ser Asn Ile Thr
        435                 440                 445
Gly Leu Leu Leu Val Arg Asp Gly Gly Asn Ile Asn Arg Thr Asn Glu
450                 455                 460
Thr Phe Arg Pro Gly Gly Gly Asn Met Lys Asp Asn Trp Arg Ser Glu
```

-continued

```
                465                 470                 475                 480
Leu Tyr Lys Tyr Lys Val Val Glu Ile Lys Pro Leu Gly Val Ala Pro
                    485                 490                 495

Thr Arg Ala Lys Arg Val Val Glu Ser Glu Lys Ser Ala Val Gly
                500                 505                 510

Leu Gly Ala Val Phe Leu Gly Phe Leu Gly Thr Ala Gly Ser Thr Met
                515                 520                 525

Gly Ala Ala Ser Leu Thr Leu Thr Val Gln Ala Arg Gln Val Leu Ser
            530                 535                 540

Gly Ile Val Gln Gln Gln Ser Asn Leu Leu Lys Ala Ile Glu Ala Gln
545                 550                 555                 560

Gln His Leu Leu Lys Leu Thr Val Trp Gly Ile Lys Gln Leu Gln Ala
                565                 570                 575

Arg Ile Leu Ala Val Glu Arg Tyr Leu Arg Asp Gln Gln Leu Leu Gly
                580                 585                 590

Ile Trp Gly Cys Ser Gly Lys Leu Ile Cys Thr Thr Asn Val Pro Trp
                595                 600                 605

Asn Ser Ser Trp Ser Asn Lys Ser Gln Glu Glu Ile Trp Asn Asn Met
            610                 615                 620

Thr Trp Met Gln Trp Asp Arg Glu Ile Ser Asn Tyr Thr Asp Thr Ile
625                 630                 635                 640

Tyr Arg Leu Leu Glu Asp Ser Gln Asn Gln Gln Glu Lys Asn Glu Gln
                645                 650                 655

Asp Leu Leu Ala Leu Asp Lys Trp Ala Ser Leu Trp Asn Trp Phe Ser
                660                 665                 670

Ile Thr Asn Trp Leu Trp
            675

<210> SEQ ID NO 6
<211> LENGTH: 685
<212> TYPE: PRT
<213> ORGANISM: Artificial Sequence
<220> FEATURE:
<223> OTHER INFORMATION: Synthetic Construct (Mosaic gp140 Env1)

<400> SEQUENCE: 6

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
```

-continued

```
            145                 150                 155                 160
Ser Phe Asn Ile Thr Thr Ser Ile Arg Asn Lys Val Gln Lys Gln Tyr
                    165                 170                 175
Ala Leu Phe Tyr Lys Leu Asp Val Val Pro Ile Asp Asn Asp Ser Asn
                    180                 185                 190
Asn Thr Asn Tyr Arg Leu Ile Ser Cys Asn Thr Ser Val Ile Thr Gln
                    195                 200                 205
Ala Cys Pro Lys Val Ser Phe Glu Pro Ile Pro Ile His Tyr Cys Ala
        210                 215                 220
Pro Ala Gly Phe Ala Ile Leu Lys Cys Asn Asp Lys Lys Phe Asn Gly
225                 230                 235                 240
Thr Gly Pro Cys Thr Asn Val Ser Thr Val Gln Cys Thr His Gly Ile
                    245                 250                 255
Arg Pro Val Val Ser Thr Gln Leu Leu Leu Asn Gly Ser Leu Ala Glu
                    260                 265                 270
Glu Glu Val Val Ile Arg Ser Glu Asn Phe Thr Asn Asn Ala Lys Thr
                    275                 280                 285
Ile Met Val Gln Leu Asn Val Ser Val Glu Ile Asn Cys Thr Arg Pro
        290                 295                 300
Asn Asn Asn Thr Arg Lys Ser Ile His Ile Gly Pro Gly Arg Ala Phe
305                 310                 315                 320
Tyr Thr Ala Gly Asp Ile Ile Gly Asp Ile Arg Gln Ala His Cys Asn
                    325                 330                 335
Ile Ser Arg Ala Asn Trp Asn Asn Thr Leu Arg Gln Ile Val Glu Lys
                    340                 345                 350
Leu Gly Lys Gln Phe Gly Asn Asn Lys Thr Ile Val Phe Asn His Ser
                    355                 360                 365
Ser Gly Gly Asp Pro Glu Ile Val Met His Ser Phe Asn Cys Gly Gly
        370                 375                 380
Glu Phe Phe Tyr Cys Asn Ser Thr Lys Leu Phe Asn Ser Thr Trp Thr
385                 390                 395                 400
Trp Asn Asn Ser Thr Trp Asn Asn Thr Lys Arg Ser Asn Asp Thr Glu
                    405                 410                 415
Glu His Ile Thr Leu Pro Cys Arg Ile Lys Gln Ile Ile Asn Met Trp
                    420                 425                 430
Gln Glu Val Gly Lys Ala Met Tyr Ala Pro Pro Ile Arg Gly Gln Ile
                    435                 440                 445
Arg Cys Ser Ser Asn Ile Thr Gly Leu Leu Leu Thr Arg Asp Gly Gly
        450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                    485                 490                 495
Glu Pro Leu Gly Val Ala Pro Thr Lys Ala Lys Arg Arg Val Val Gln
                    500                 505                 510
Ser Glu Lys Ser Ala Val Gly Ile Gly Ala Val Phe Leu Gly Phe Leu
                    515                 520                 525
Gly Ala Ala Gly Ser Thr Met Gly Ala Ala Ser Met Thr Leu Thr Val
        530                 535                 540
Gln Ala Arg Leu Leu Leu Ser Gly Ile Val Gln Gln Asn Asn Leu
545                 550                 555                 560
Leu Arg Ala Ile Glu Ala Gln Gln His Leu Leu Gln Leu Thr Val Trp
                    565                 570                 575
```

```
Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
            595                 600                 605

Cys Thr Thr Thr Val Pro Trp Asn Ala Ser Trp Ser Asn Lys Ser Leu
            610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
            645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp
            675                 680                 685

<210> SEQ ID NO 7
<211> LENGTH: 1350
<212> TYPE: PRT
<213> ORGANISM: Artificial Sequence
<220> FEATURE:
<223> OTHER INFORMATION: Synthetic Construct (Mosaic gagpol1 v3)

<400> SEQUENCE: 7

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Gln Asn Lys Ser Lys
            100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255
```

```
Pro Val Gly Glu Ile Tyr Lys Arg Trp Ile Leu Gly Leu Asn Lys
        260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
        290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
        515                 520                 525

Thr Glu Glu Lys Ile Lys Ala Leu Thr Ala Ile Cys Glu Glu Met Glu
    530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Ser Val
        595                 600                 605

Thr Val Leu Ala Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
            660                 665                 670
```

```
Phe Arg Ala Lys Asn Pro Glu Ile Val Ile Tyr Gln Tyr Met Ala Ala
            675                 680                 685

Leu Tyr Val Gly Ser Asp Leu Glu Ile Gly Gln His Arg Ala Lys Ile
        690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
        755                 760                 765

Ala Ser Gln Ile Tyr Pro Gly Ile Lys Val Arg Gln Leu Cys Lys Leu
        770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
        835                 840                 845

Lys Asn Leu Lys Thr Gly Lys Tyr Ala Lys Met Arg Thr Ala His Thr
        850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
            900                 905                 910

Ile Pro Glu Trp Glu Phe Val Asn Thr Pro Pro Leu Val Lys Leu Trp
        915                 920                 925

Tyr Gln Leu Glu Lys Asp Pro Ile Ala Gly Val Glu Thr Phe Tyr Val
        930                 935                 940

Ala Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Ala Leu Gln Ala Ile Tyr Leu Ala Leu Gln Asp Ser Gly
            980                 985                 990

Ser Glu Val Asn Ile Val Thr Ala Ser Gln Tyr Ala Leu Gly Ile Ile
        995                 1000                1005

Gln Ala Gln Pro Asp Lys Ser Glu Ser Glu Leu Val Asn Gln Ile
        1010                1015                1020

Ile Glu Gln Leu Ile Lys Lys Glu Arg Val Tyr Leu Ser Trp Val
        1025                1030                1035

Pro Ala His Lys Gly Ile Gly Gly Asn Glu Gln Val Asp Lys Leu
        1040                1045                1050

Val Ser Ser Gly Ile Arg Lys Val Leu Phe Leu Asp Gly Ile Asp
        1055                1060                1065

Lys Ala Gln Glu Glu His Glu Lys Tyr His Ser Asn Trp Arg Ala
        1070                1075                1080

Met Ala Ser Asp Phe Asn Leu Pro Pro Val Val Ala Lys Glu Ile
```

```
                    1085                  1090                 1095
Val Ala Ser Cys Asp Gln Cys Gln Leu Lys Gly Glu Ala Met His
       1100                 1105                 1110

Gly Gln Val Asp Cys Ser Pro Gly Ile Trp Gln Leu Ala Cys Thr
       1115                 1120                 1125

His Leu Glu Gly Lys Ile Ile Leu Val Ala Val His Val Ala Ser
       1130                 1135                 1140

Gly Tyr Ile Glu Ala Glu Val Ile Pro Ala Glu Thr Gly Gln Glu
       1145                 1150                 1155

Thr Ala Tyr Phe Ile Leu Lys Leu Ala Gly Arg Trp Pro Val Lys
       1160                 1165                 1170

Val Ile His Thr Ala Asn Gly Ser Asn Phe Thr Ser Ala Ala Val
       1175                 1180                 1185

Lys Ala Ala Cys Trp Trp Ala Gly Ile Gln Gln Glu Phe Gly Ile
       1190                 1195                 1200

Pro Tyr Asn Pro Gln Ser Gln Gly Val Val Ala Ser Met Asn Lys
       1205                 1210                 1215

Glu Leu Lys Lys Ile Ile Gly Gln Val Arg Asp Gln Ala Glu His
       1220                 1225                 1230

Leu Lys Thr Ala Val Gln Met Ala Val Phe Ile His Asn Phe Lys
       1235                 1240                 1245

Arg Lys Gly Gly Ile Gly Gly Tyr Ser Ala Gly Glu Arg Ile Ile
       1250                 1255                 1260

Asp Ile Ile Ala Thr Asp Ile Gln Thr Lys Glu Leu Gln Lys Gln
       1265                 1270                 1275

Ile Ile Lys Ile Gln Asn Phe Arg Val Tyr Tyr Arg Asp Ser Arg
       1280                 1285                 1290

Asp Pro Ile Trp Lys Gly Pro Ala Lys Leu Leu Trp Lys Gly Glu
       1295                 1300                 1305

Gly Ala Val Val Ile Gln Asp Asn Ser Asp Ile Lys Val Val Pro
       1310                 1315                 1320

Arg Arg Lys Val Lys Ile Ile Lys Asp Tyr Gly Lys Gln Met Ala
       1325                 1330                 1335

Gly Ala Asp Cys Val Ala Gly Arg Gln Asp Glu Asp
       1340                 1345                 1350

<210> SEQ ID NO 8
<211> LENGTH: 857
<212> TYPE: PRT
<213> ORGANISM: Artificial Sequence
<220> FEATURE:
<223> OTHER INFORMATION: Synthetic Construct (Mosaic gp160 Env1)

<400> SEQUENCE: 8

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
```

```
                     85                  90                  95
Asn Asn Met Val Glu Gln Met His Glu Asp Ile Ile Ser Leu Trp Asp
                100                 105                 110
Gln Ser Leu Lys Pro Cys Val Lys Leu Thr Pro Leu Cys Val Thr Leu
            115                 120                 125
Asn Cys Thr Asp Asp Val Arg Asn Val Thr Asn Asn Ala Thr Asn Thr
        130                 135                 140
Asn Ser Ser Trp Gly Glu Pro Met Glu Lys Gly Glu Ile Lys Asn Cys
145                 150                 155                 160
Ser Phe Asn Ile Thr Thr Ser Ile Arg Asn Lys Val Gln Lys Gln Tyr
                165                 170                 175
Ala Leu Phe Tyr Lys Leu Asp Val Val Pro Ile Asp Asn Asp Ser Asn
            180                 185                 190
Asn Thr Asn Tyr Arg Leu Ile Ser Cys Asn Thr Ser Val Ile Thr Gln
        195                 200                 205
Ala Cys Pro Lys Val Ser Phe Glu Pro Ile Pro Ile His Tyr Cys Ala
    210                 215                 220
Pro Ala Gly Phe Ala Ile Leu Lys Cys Asn Asp Lys Lys Phe Asn Gly
225                 230                 235                 240
Thr Gly Pro Cys Thr Asn Val Ser Thr Val Gln Cys Thr His Gly Ile
                245                 250                 255
Arg Pro Val Val Ser Thr Gln Leu Leu Leu Asn Gly Ser Leu Ala Glu
            260                 265                 270
Glu Glu Val Val Ile Arg Ser Glu Asn Phe Thr Asn Asn Ala Lys Thr
        275                 280                 285
Ile Met Val Gln Leu Asn Val Ser Val Glu Ile Asn Cys Thr Arg Pro
    290                 295                 300
Asn Asn Asn Thr Arg Lys Ser Ile His Ile Gly Pro Gly Arg Ala Phe
305                 310                 315                 320
Tyr Thr Ala Gly Asp Ile Ile Gly Asp Ile Arg Gln Ala His Cys Asn
                325                 330                 335
Ile Ser Arg Ala Asn Trp Asn Asn Thr Leu Arg Gln Ile Val Glu Lys
            340                 345                 350
Leu Gly Lys Gln Phe Gly Asn Asn Lys Thr Ile Val Phe Asn His Ser
        355                 360                 365
Ser Gly Gly Asp Pro Glu Ile Val Met His Ser Phe Asn Cys Gly Gly
    370                 375                 380
Glu Phe Phe Tyr Cys Asn Ser Thr Lys Leu Phe Asn Ser Thr Trp Thr
385                 390                 395                 400
Trp Asn Asn Ser Thr Trp Asn Asn Thr Lys Arg Ser Asn Asp Thr Glu
                405                 410                 415
Glu His Ile Thr Leu Pro Cys Arg Ile Lys Gln Ile Ile Asn Met Trp
            420                 425                 430
Gln Glu Val Gly Lys Ala Met Tyr Ala Pro Pro Ile Arg Gly Gln Ile
        435                 440                 445
Arg Cys Ser Ser Asn Ile Thr Gly Leu Leu Leu Thr Arg Asp Gly Gly
    450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Arg Arg Val Val Gln
            500                 505                 510
```

```
Arg Glu Lys Arg Ala Val Gly Ile Gly Ala Val Phe Leu Gly Phe Leu
        515                 520                 525

Gly Ala Ala Gly Ser Thr Met Gly Ala Ala Ser Met Thr Leu Thr Val
    530                 535                 540

Gln Ala Arg Leu Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
            565                 570                 575

Gly Ile Lys Gln Leu Gln Ala Arg Val Leu Ala Val Glu Arg Tyr Leu
        580                 585                 590

Lys Asp Gln Gln Leu Leu Gly Ile Trp Gly Cys Ser Gly Lys Leu Ile
    595                 600                 605

Cys Thr Thr Thr Val Pro Trp Asn Ala Ser Trp Ser Asn Lys Ser Leu
610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
            645                 650                 655

Gln Gln Glu Lys Asn Glu Gln Glu Leu Leu Glu Leu Asp Lys Trp Ala
        660                 665                 670

Ser Leu Trp Asn Trp Phe Asp Ile Ser Asn Trp Leu Trp Tyr Ile Lys
    675                 680                 685

Ile Phe Ile Met Ile Val Gly Gly Leu Val Gly Leu Arg Ile Val Phe
690                 695                 700

Ala Val Leu Ser Ile Val Asn Arg Val Arg Gln Gly Tyr Ser Pro Leu
705                 710                 715                 720

Ser Phe Gln Thr Arg Leu Pro Ala Pro Arg Gly Pro Asp Arg Pro Glu
            725                 730                 735

Gly Ile Glu Glu Glu Gly Gly Glu Arg Asp Arg Asp Arg Ser Val Arg
        740                 745                 750

Leu Val Asp Gly Phe Leu Val Leu Ile Trp Asp Asp Leu Gln Ser Leu
    755                 760                 765

Cys Leu Phe Ser Tyr His Arg Leu Arg Asp Leu Leu Leu Ile Val Glu
770                 775                 780

Leu Leu Gly Arg Arg Gly Trp Glu Ala Leu Lys Tyr Trp Trp Asn Leu
785                 790                 795                 800

Leu Gln Tyr Trp Ser Gln Glu Leu Lys Asn Ser Ala Ile Ser Leu Leu
            805                 810                 815

Asn Ala Thr Ala Val Ala Val Ala Glu Gly Thr Asp Arg Val Ile Glu
        820                 825                 830

Ala Leu Gln Arg Ala Cys Arg Ala Ile Leu His Ile Pro Arg Arg Ile
    835                 840                 845

Arg Gln Gly Leu Glu Arg Leu Leu Leu
    850                 855

<210> SEQ ID NO 9
<211> LENGTH: 867
<212> TYPE: PRT
<213> ORGANISM: Artificial Sequence
<220> FEATURE:
<223> OTHER INFORMATION: Synthetic Construct (Mosaic gp160 Env2)

<400> SEQUENCE: 9

Met Arg Val Arg Gly Ile Gln Arg Asn Trp Pro Gln Trp Trp Ile Trp
1               5                   10                  15
```

```
Gly Ile Leu Gly Phe Trp Met Ile Ile Cys Arg Val Met Gly Asn
         20                  25                  30
Leu Trp Val Thr Val Tyr Tyr Gly Val Pro Val Trp Lys Glu Ala Lys
     35                  40                  45
Thr Thr Leu Phe Cys Ala Ser Asp Ala Lys Ala Tyr Glu Lys Glu Val
 50                  55                  60
His Asn Val Trp Ala Thr His Ala Cys Val Pro Thr Asp Pro Asn Pro
 65                  70                  75                  80
Gln Glu Met Val Leu Glu Asn Val Thr Glu Asn Phe Asn Met Trp Lys
                 85                  90                  95
Asn Asp Met Val Asp Gln Met His Glu Asp Ile Ile Arg Leu Trp Asp
                100                 105                 110
Gln Ser Leu Lys Pro Cys Val Lys Leu Thr Pro Leu Cys Val Thr Leu
         115                 120                 125
Glu Cys Arg Asn Val Arg Asn Val Ser Ser Asn Gly Thr Tyr Asn Ile
130                 135                 140
Ile His Asn Glu Thr Tyr Lys Glu Met Lys Asn Cys Ser Phe Asn Ala
145                 150                 155                 160
Thr Thr Val Val Glu Asp Arg Lys Gln Lys Val His Ala Leu Phe Tyr
                165                 170                 175
Arg Leu Asp Ile Val Pro Leu Asp Glu Asn Asn Ser Ser Glu Lys Ser
            180                 185                 190
Ser Glu Asn Ser Ser Glu Tyr Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Glu Glu Ile Ile Ile Arg Ser Glu Asn Leu Thr Asn
        275                 280                 285
Asn Ala Lys Thr Ile Ile Val His Leu Asn Glu Thr Val Asn Ile Thr
    290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Asn Phe
        355                 360                 365
Thr Ser Ser Ser Gly Gly Asp Leu Glu Ile Thr Thr His Ser Phe Asn
    370                 375                 380
Cys Arg Gly Glu Phe Phe Tyr Cys Asn Thr Ser Gly Leu Phe Asn Gly
385                 390                 395                 400
Thr Tyr Met Pro Asn Gly Thr Asn Ser Asn Ser Ser Asn Ile Thr
                405                 410                 415
Leu Pro Cys Arg Ile Lys Gln Ile Ile Asn Met Trp Gln Glu Val Gly
            420                 425                 430
```

```
Arg Ala Met Tyr Ala Pro Pro Ile Ala Gly Asn Ile Thr Cys Arg Ser
            435                 440                 445

Asn Ile Thr Gly Leu Leu Thr Arg Asp Gly Ser Asn Gly
450                 455                 460

Val Pro Asn Asp Thr Glu Thr Phe Arg Pro Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Arg
                500                 505                 510

Glu Lys Arg Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
            530                 535                 540

Ala Arg Gln Leu Leu Ser Gly Ile Val Gln Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
                580                 585                 590

Asp Gln Gln Leu Leu Gly Leu Trp Gly Cys Ser Gly Lys Leu Ile Cys
            595                 600                 605

Thr Thr Ala Val Pro Trp Asn Thr Ser Trp Ser Asn Lys Ser Gln Thr
            610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
                660                 665                 670

Leu Trp Asn Trp Phe Asp Ile Thr Asn Trp Leu Trp Tyr Ile Lys Ile
            675                 680                 685

Phe Ile Met Ile Val Gly Gly Leu Ile Gly Leu Arg Ile Ile Leu Gly
            690                 695                 700

Val Leu Ser Ile Val Arg Arg Val Arg Gln Gly Tyr Ser Pro Leu Ser
705                 710                 715                 720

Phe Gln Thr Leu Thr Pro Asn Pro Arg Gly Leu Asp Arg Leu Gly Arg
                725                 730                 735

Ile Glu Glu Glu Gly Gly Glu Gln Asp Arg Asp Arg Ser Ile Arg Leu
            740                 745                 750

Val Asn Gly Phe Leu Ala Leu Ala Trp Asp Asp Leu Arg Ser Leu Cys
            755                 760                 765

Leu Phe Ser Tyr His Gln Leu Arg Asp Phe Ile Leu Ile Val Ala Arg
            770                 775                 780

Ala Val Glu Leu Leu Gly Arg Ser Ser Leu Arg Gly Leu Gln Arg Gly
785                 790                 795                 800

Trp Glu Ala Leu Lys Tyr Leu Gly Asn Leu Val Gln Tyr Trp Gly Leu
                805                 810                 815

Glu Leu Lys Lys Gly Ala Ile Ser Leu Leu Asp Thr Ile Ala Ile Ala
            820                 825                 830

Val Ala Glu Gly Thr Asp Arg Ile Ile Glu Leu Ile Gln Ser Ile Cys
835                 840                 845

Arg Ala Ile Arg Asn Ile Pro Arg Arg Ile Arg Gln Gly Phe Glu Ala
```

```
                850                 855                 860

Ser Leu Leu
865

<210> SEQ ID NO 10
<211> LENGTH: 500
<212> TYPE: PRT
<213> ORGANISM: Artificial Sequence
<220> FEATURE:
<223> OTHER INFORMATION: Synthetic Construct (Mosaic gag1)

<400> SEQUENCE: 10

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
```

```
                340             345             350
Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln
            500

<210> SEQ ID NO 11
<211> LENGTH: 491
<212> TYPE: PRT
<213> ORGANISM: Artificial Sequence
<220> FEATURE:
<223> OTHER INFORMATION: Synthetic Construct (Mosaic gag2)

<400> SEQUENCE: 11

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
                100                 105                 110

Gln Lys Thr Gln Gln Ala Lys Glu Ala Asp Gly Lys Val Ser Gln Asn
            115                 120                 125

Tyr Pro Ile Val Gln Asn Leu Gln Gly Gln Met Val His Gln Pro Ile
        130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
```

-continued

```
            195                 200                 205
Trp Asp Arg Leu His Pro Val His Ala Gly Pro Val Ala Pro Gly Gln
210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Ile Pro Val Gly
            245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln
                485                 490

<210> SEQ ID NO 12
<211> LENGTH: 999
<212> TYPE: PRT
<213> ORGANISM: Artificial Sequence
<220> FEATURE:
<223> OTHER INFORMATION: Synthetic Construct (Mosaic pol1)

<400> SEQUENCE: 12

Phe Phe Arg Glu Asn Leu Ala Phe Gln Gln Gly Glu Ala Arg Glu Phe
1               5                   10                  15

Pro Ser Glu Gln Thr Arg Ala Asn Ser Pro Thr Ser Arg Glu Leu Gln
                20                  25                  30

Val Arg Gly Asp Asn Pro His Ser Glu Ala Gly Ala Glu Arg Gln Gly
            35                  40                  45

Thr Leu Asn Phe Pro Gln Ile Thr Leu Trp Gln Arg Pro Leu Val Ser
        50                  55                  60

Ile Lys Val Gly Gly Gln Ile Arg Glu Ala Leu Leu Asp Thr Gly Ala
```

```
                65                  70                  75                  80
Asp Asp Thr Val Leu Glu Asp Ile Asn Leu Pro Gly Lys Trp Lys Pro
                        85                  90                  95
Lys Met Ile Gly Gly Ile Gly Gly Phe Ile Lys Val Arg Gln Tyr Asp
                        100                 105                 110
Gln Ile Leu Ile Glu Ile Cys Gly Lys Lys Ala Ile Gly Thr Val Leu
                        115                 120                 125
Val Gly Pro Thr Pro Val Asn Ile Ile Gly Arg Asn Met Leu Thr Gln
                        130                 135                 140
Leu Gly Cys Thr Leu Asn Phe Pro Ile Ser Pro Ile Glu Thr Val Pro
145                     150                 155                 160
Val Lys Leu Lys Pro Gly Met Asp Gly Pro Arg Val Lys Gln Trp Pro
                        165                 170                 175
Leu Thr Glu Glu Lys Ile Lys Ala Leu Thr Ala Ile Cys Glu Glu Met
                        180                 185                 190
Glu Lys Glu Gly Lys Ile Thr Lys Ile Gly Pro Glu Asn Pro Tyr Asn
                        195                 200                 205
Thr Pro Val Phe Ala Ile Lys Lys Lys Asp Ser Thr Lys Trp Arg Lys
                        210                 215                 220
Leu Val Asp Phe Arg Glu Leu Asn Lys Arg Thr Gln Asp Phe Trp Glu
225                     230                 235                 240
Val Gln Leu Gly Ile Pro His Pro Ala Gly Leu Lys Lys Lys Lys Ser
                        245                 250                 255
Val Thr Val Leu Asp Val Gly Asp Ala Tyr Phe Ser Val Pro Leu Asp
                        260                 265                 270
Glu Gly Phe Arg Lys Tyr Thr Ala Phe Thr Ile Pro Ser Thr Asn Asn
                        275                 280                 285
Glu Thr Pro Gly Ile Arg Tyr Gln Tyr Asn Val Leu Pro Gln Gly Trp
                        290                 295                 300
Lys Gly Ser Pro Ala Ile Phe Gln Cys Ser Met Thr Arg Ile Leu Glu
305                     310                 315                 320
Pro Phe Arg Ala Lys Asn Pro Glu Ile Val Ile Tyr Gln Tyr Met Asp
                        325                 330                 335
Asp Leu Tyr Val Gly Ser Asp Leu Glu Ile Gly Gln His Arg Ala Lys
                        340                 345                 350
Ile Glu Glu Leu Arg Glu His Leu Leu Lys Trp Gly Phe Thr Thr Pro
                        355                 360                 365
Asp Lys Lys His Gln Lys Glu Pro Pro Phe Leu Trp Met Gly Tyr Glu
                        370                 375                 380
Leu His Pro Asp Lys Trp Thr Val Gln Pro Ile Gln Leu Pro Glu Lys
385                     390                 395                 400
Asp Ser Trp Thr Val Asn Asp Ile Gln Lys Leu Val Gly Lys Leu Asn
                        405                 410                 415
Trp Ala Ser Gln Ile Tyr Pro Gly Ile Lys Val Arg Gln Leu Cys Lys
                        420                 425                 430
Leu Leu Arg Gly Ala Lys Ala Leu Thr Asp Ile Val Pro Leu Thr Glu
                        435                 440                 445
Glu Ala Glu Leu Glu Leu Ala Glu Asn Arg Glu Ile Leu Lys Glu Pro
                        450                 455                 460
Val His Gly Val Tyr Tyr Asp Pro Ser Lys Asp Leu Ile Ala Glu Ile
465                     470                 475                 480
Gln Lys Gln Gly His Asp Gln Trp Thr Tyr Gln Ile Tyr Gln Glu Pro
                        485                 490                 495
```

```
Phe Lys Asn Leu Lys Thr Gly Lys Tyr Ala Lys Met Arg Thr Ala His
            500                 505                 510

Thr Asn Asp Val Lys Gln Leu Thr Glu Ala Val Gln Lys Ile Ala Met
            515                 520                 525

Glu Ser Ile Val Ile Trp Gly Lys Thr Pro Lys Phe Arg Leu Pro Ile
530                 535                 540

Gln Lys Glu Thr Trp Glu Thr Trp Trp Thr Asp Tyr Trp Gln Ala Thr
545                 550                 555                 560

Trp Ile Pro Glu Trp Glu Phe Val Asn Thr Pro Pro Leu Val Lys Leu
                565                 570                 575

Trp Tyr Gln Leu Glu Lys Asp Pro Ile Ala Gly Val Glu Thr Phe Tyr
            580                 585                 590

Val Asp Gly Ala Ala Asn Arg Glu Thr Lys Leu Gly Lys Ala Gly Tyr
            595                 600                 605

Val Thr Asp Arg Gly Arg Gln Lys Ile Val Ser Leu Thr Glu Thr Thr
            610                 615                 620

Asn Gln Lys Thr Glu Leu Gln Ala Ile Tyr Leu Ala Leu Gln Asp Ser
625                 630                 635                 640

Gly Ser Glu Val Asn Ile Val Thr Asp Ser Gln Tyr Ala Leu Gly Ile
                645                 650                 655

Ile Gln Ala Gln Pro Asp Lys Ser Glu Ser Glu Leu Val Asn Gln Ile
            660                 665                 670

Ile Glu Gln Leu Ile Lys Lys Glu Arg Val Tyr Leu Ser Trp Val Pro
            675                 680                 685

Ala His Lys Gly Ile Gly Gly Asn Glu Gln Val Asp Lys Leu Val Ser
            690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Asp
                725                 730                 735

Phe Asn Leu Pro Pro Val Val Ala Lys Glu Ile Val Ala Ser Cys Asp
            740                 745                 750

Gln Cys Gln Leu Lys Gly Glu Ala Met His Gly Gln Val Asp Cys Ser
            755                 760                 765

Pro Gly Ile Trp Gln Leu Asp Cys Thr His Leu Glu Gly Lys Ile Ile
            770                 775                 780

Leu Val Ala Val His Val Ala Ser Gly Tyr Ile Glu Ala Glu Val Ile
785                 790                 795                 800

Pro Ala Glu Thr Gly Gln Glu Thr Ala Tyr Phe Ile Leu Lys Leu Ala
                805                 810                 815

Gly Arg Trp Pro Val Lys Val Ile His Thr Asp Asn Gly Ser Asn Phe
            820                 825                 830

Thr Ser Ala Ala Val Lys Ala Ala Cys Trp Trp Ala Gly Ile Gln Gln
            835                 840                 845

Glu Phe Gly Ile Pro Tyr Asn Pro Gln Ser Gln Gly Val Val Glu Ser
            850                 855                 860

Met Asn Lys Glu Leu Lys Lys Ile Ile Gly Gln Val Arg Asp Gln Ala
865                 870                 875                 880

Glu His Leu Lys Thr Ala Val Gln Met Ala Val Phe Ile His Asn Phe
                885                 890                 895

Lys Arg Lys Gly Gly Ile Gly Gly Tyr Ser Ala Gly Glu Arg Ile Ile
            900                 905                 910
```

```
Asp Ile Ile Ala Thr Asp Ile Gln Thr Lys Glu Leu Gln Lys Gln Ile
            915                 920                 925

Ile Lys Ile Gln Asn Phe Arg Val Tyr Tyr Arg Asp Ser Arg Asp Pro
        930                 935                 940

Ile Trp Lys Gly Pro Ala Lys Leu Leu Trp Lys Gly Glu Gly Ala Val
945                 950                 955                 960

Val Ile Gln Asp Asn Ser Asp Ile Lys Val Val Pro Arg Arg Lys Val
                965                 970                 975

Lys Ile Ile Lys Asp Tyr Gly Lys Gln Met Ala Gly Ala Asp Cys Val
            980                 985                 990

Ala Gly Arg Gln Asp Glu Asp
            995

<210> SEQ ID NO 13
<211> LENGTH: 1003
<212> TYPE: PRT
<213> ORGANISM: Artificial Sequence
<220> FEATURE:
<223> OTHER INFORMATION: Synthetic Construct (Mosaic pol2)

<400> SEQUENCE: 13

Phe Phe Arg Glu Asn Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Pro Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Ile Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270
```

```
Val Pro Leu Asp Glu Asp Phe Arg Lys Tyr Thr Ala Phe Thr Ile Pro
            275                 280                 285

Ser Ile Asn Asn Glu Thr Pro Gly Ile Arg Tyr Gln Tyr Asn Val Leu
        290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Lys
            420                 425                 430

Gln Leu Cys Lys Leu Leu Arg Gly Thr Lys Ala Leu Thr Glu Val Val
        435                 440                 445

Pro Leu Thr Glu Glu Ala Glu Leu Glu Leu Ala Glu Asn Arg Glu Ile
450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Arg Gly Ala His Thr Asn Asp Val Lys Gln Leu Thr Glu Ala Val Gln
        515                 520                 525

Lys Ile Ala Thr Glu Ser Ile Val Ile Trp Gly Lys Thr Pro Lys Phe
530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asp Arg Gly Arg Gln Lys Val Val Ser Leu
610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
```

```
                    690                 695                 700

Lys Leu Val Ser Arg Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                    725                 730                 735

Met Ala Ser Glu Phe Asn Leu Pro Pro Ile Val Ala Lys Glu Ile Val
                740                 745                 750

Ala Ser Cys Asp Lys Cys Gln Leu Lys Gly Glu Ala Ile His Gly Gln
            755                 760                 765

Val Asp Cys Ser Pro Gly Ile Trp Gln Leu Asp Cys Thr His Leu Glu
770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                    805                 810                 815

Leu Lys Leu Ala Gly Arg Trp Pro Val Lys Thr Ile His Thr Asp Asn
                820                 825                 830

Gly Ser Asn Phe Thr Ser Ala Thr Val Lys Ala Ala Cys Trp Trp Ala
            835                 840                 845

Gly Ile Lys Gln Glu Phe Gly Ile Pro Tyr Asn Pro Gln Ser Gln Gly
        850                 855                 860

Val Val Glu Ser Ile Asn Lys Glu Leu Lys Lys Ile Ile Gly Gln Val
865                 870                 875                 880

Arg Asp Gln Ala Glu His Leu Lys Thr Ala Val Gln Met Ala Val Phe
                    885                 890                 895

Ile His Asn Phe Lys Arg Lys Gly Gly Ile Gly Glu Tyr Ser Ala Gly
                900                 905                 910

Glu Arg Ile Val Asp Ile Ile Ala Ser Asp Ile Gln Thr Lys Glu Leu
            915                 920                 925

Gln Lys Gln Ile Thr Lys Ile Gln Asn Phe Arg Val Tyr Tyr Arg Asp
        930                 935                 940

Ser Arg Asp Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                    965                 970                 975

Arg Arg Lys Ala Lys Ile Ile Arg Asp Tyr Gly Lys Gln Met Ala Gly
                980                 985                 990

Asp Asp Cys Val Ala Ser Arg Gln Asp Glu Asp
            995                 1000
```

<210> SEQ ID NO 14
<211> LENGTH: 206
<212> TYPE: PRT
<213> ORGANISM: Artificial Sequence
<220> FEATURE:
<223> OTHER INFORMATION: Synthetic Construct (Mosaic nef1)

<400> SEQUENCE: 14

```
Met Gly Gly Lys Trp Ser Lys Ser Ser Val Val Gly Trp Pro Ala Ile
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Asp Cys Ala Trp Leu Glu Ala Gln Glu Glu Glu
```

```
            50                  55                  60
Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
            100                 105                 110

Trp Val Tyr His Thr Gln Gly Tyr Phe Pro Asp Trp Gln Asn Tyr Thr
            115                 120                 125

Pro Gly Pro Gly Ile Arg Tyr Pro Leu Thr Phe Gly Trp Cys Phe Lys
            130                 135                 140

Leu Val Pro Val Glu Pro Glu Lys Ile Glu Glu Ala Asn Glu Gly Glu
145                 150                 155                 160

Asn Asn Ser Leu Leu His Pro Met Ser Gln His Gly Met Asp Asp Pro
                165                 170                 175

Glu Lys Glu Val Leu Met Trp Lys Phe Asp Ser Arg Leu Ala Phe His
                180                 185                 190

His Met Ala Arg Glu Leu His Pro Glu Tyr Tyr Lys Asp Cys
                195                 200                 205

<210> SEQ ID NO 15
<211> LENGTH: 206
<212> TYPE: PRT
<213> ORGANISM: Artificial Sequence
<220> FEATURE:
<223> OTHER INFORMATION: Synthetic Construct (Mosaic nef2)

<400> SEQUENCE: 15

Met Gly Gly Lys Trp Ser Lys Ser Ser Ile Val Gly Trp Pro Ala Val
1               5                   10                  15

Arg Glu Arg Ile Arg Arg Ala Glu Pro Ala Ala Glu Gly Val Gly Ala
                20                  25                  30

Ala Ser Gln Asp Leu Asp Lys Tyr Gly Ala Leu Thr Ser Ser Asn Thr
            35                  40                  45

Ala Ala Thr Asn Ala Asp Cys Ala Trp Leu Glu Ala Gln Glu Asp Glu
        50                  55                  60

Glu Val Gly Phe Pro Val Lys Pro Gln Val Pro Leu Arg Pro Met Thr
65                  70                  75                  80

Tyr Lys Ala Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
            100                 105                 110

Trp Val Tyr Asn Thr Gln Gly Phe Phe Pro Asp Trp Gln Asn Tyr Thr
            115                 120                 125

Pro Gly Pro Gly Val Arg Tyr Pro Leu Thr Phe Gly Trp Cys Phe Lys
            130                 135                 140

Leu Val Pro Val Asp Pro Arg Glu Val Glu Glu Ala Asn Lys Gly Glu
145                 150                 155                 160

Asn Asn Cys Leu Leu His Pro Met Asn Leu His Gly Met Asp Asp Pro
                165                 170                 175

Glu Arg Glu Val Leu Val Trp Arg Phe Asp Ser Arg Leu Ala Phe His
                180                 185                 190

His Met Ala Arg Glu Lys His Pro Glu Tyr Tyr Lys Asn Cys
                195                 200                 205
```

<210> SEQ ID NO 16
<211> LENGTH: 850
<212> TYPE: PRT
<213> ORGANISM: Artificial Sequence
<220> FEATURE:
<223> OTHER INFORMATION: Synthetic Construct (Mosaic pol1)

<400> SEQUENCE: 16

```
Met Ala Pro Ile Ser Pro Ile Glu Thr Val Pro Val Lys Leu Lys Pro
1               5                   10                  15

Gly Met Asp Gly Pro Arg Val Lys Gln Trp Pro Leu Thr Glu Glu Lys
            20                  25                  30

Ile Lys Ala Leu Thr Ala Ile Cys Glu Glu Met Glu Lys Glu Gly Lys
        35                  40                  45

Ile Thr Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Lys Ser Val Thr Val Leu Ala
            100                 105                 110

Val Gly Asp Ala Tyr Phe Ser Val Pro Leu Asp Glu Gly Phe Arg Lys
        115                 120                 125

Tyr Thr Ala Phe Thr Ile Pro Ser Thr Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Arg Ile Leu Glu Pro Phe Arg Ala Lys
                165                 170                 175

Asn Pro Glu Ile Val Ile Tyr Gln Tyr Met Ala Ala Leu Tyr Val Gly
            180                 185                 190

Ser Asp Leu Glu Ile Gly Gln His Arg Ala Lys Ile Glu Glu Leu Arg
        195                 200                 205

Glu His Leu Leu Lys Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Ala
        275                 280                 285

Lys Ala Leu Thr Asp Ile Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly His
                325                 330                 335

Asp Gln Trp Thr Tyr Gln Ile Tyr Gln Glu Pro Phe Lys Asn Leu Lys
            340                 345                 350

Thr Gly Lys Tyr Ala Lys Met Arg Thr Ala His Thr Asn Asp Val Lys
        355                 360                 365

Gln Leu Thr Glu Ala Val Gln Lys Ile Ala Met Glu Ser Ile Val Ile
```

```
              370                 375                 380
Trp Gly Lys Thr Pro Lys Phe Arg Leu Pro Ile Gln Lys Glu Thr Trp
385                 390                 395                 400

Glu Thr Trp Trp Thr Asp Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Asp Pro Ile Ala Gly Val Glu Thr Phe Tyr Val Ala Gly Ala Ala
            435                 440                 445

Asn Arg Glu Thr Lys Leu Gly Lys Ala Gly Tyr Val Thr Asp Arg Gly
            450                 455                 460

Arg Gln Lys Ile Val Ser Leu Thr Glu Thr Thr Asn Gln Lys Thr Ala
465                 470                 475                 480

Leu Gln Ala Ile Tyr Leu Ala Leu Gln Asp Ser Gly Ser Glu Val Asn
                485                 490                 495

Ile Val Thr Ala Ser Gln Tyr Ala Leu Gly Ile Ile Gln Ala Gln Pro
            500                 505                 510

Asp Lys Ser Glu Ser Glu Leu Val Asn Gln Ile Ile Glu Gln Leu Ile
            515                 520                 525

Lys Lys Glu Arg Val Tyr Leu Ser Trp Val Pro Ala His Lys Gly Ile
            530                 535                 540

Gly Gly Asn Glu Gln Val Asp Lys Leu Val Ser Ser Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Asp Phe Asn Leu Pro Pro
                580                 585                 590

Val Val Ala Lys Glu Ile Val Ala Ser Cys Asp Gln Cys Gln Leu Lys
            595                 600                 605

Gly Glu Ala Met His Gly Gln Val Asp Cys Ser Pro Gly Ile Trp Gln
            610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Ile Leu Lys Leu Ala Gly Arg Trp Pro Val
            660                 665                 670

Lys Val Ile His Thr Ala Asn Gly Ser Asn Phe Thr Ser Ala Ala Val
            675                 680                 685

Lys Ala Ala Cys Trp Trp Ala Gly Ile Gln Gln Glu Phe Gly Ile Pro
            690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
                740                 745                 750

Ile Gly Gly Tyr Ser Ala Gly Glu Arg Ile Ile Asp Ile Ile Ala Thr
            755                 760                 765

Asp Ile Gln Thr Lys Glu Leu Gln Lys Gln Ile Ile Lys Ile Gln Asn
            770                 775                 780

Phe Arg Val Tyr Tyr Arg Asp Ser Arg Asp Pro Ile Trp Lys Gly Pro
785                 790                 795                 800
```

```
Ala Lys Leu Leu Trp Lys Gly Glu Gly Ala Val Val Ile Gln Asp Asn
            805                 810                 815

Ser Asp Ile Lys Val Val Pro Arg Arg Lys Val Lys Ile Ile Lys Asp
            820                 825                 830

Tyr Gly Lys Gln Met Ala Gly Ala Asp Cys Val Ala Gly Arg Gln Asp
            835                 840                 845

Glu Asp
    850

<210> SEQ ID NO 17
<211> LENGTH: 850
<212> TYPE: PRT
<213> ORGANISM: Artificial Sequence
<220> FEATURE:
<223> OTHER INFORMATION: Synthetic Construct (Mosaic pol1)

<400> SEQUENCE: 17

Met Ala Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Ile Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Ala
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Ala Ala Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Ala Gly Ile Lys Val Lys Gln Leu Cys Lys Leu Leu Arg Gly Thr
        275                 280                 285

Lys Ala Leu Thr Glu Val Val Pro Leu Thr Glu Glu Ala Glu Leu Glu
    290                 295                 300
```

-continued

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
            325                 330                 335

Gly Gln Trp Thr Tyr Gln Ile Tyr Gln Glu Pro Phe Lys Asn Leu Lys
        340                 345                 350

Thr Gly Lys Tyr Ala Arg Met Arg Gly Ala His Thr Asn Asp Val Lys
    355                 360                 365

Gln Leu Thr Glu Ala Val Gln Lys Ile Ala Thr Glu Ser Ile Val Ile
370                 375                 380

Trp Gly Lys Thr Pro Lys Phe Lys Leu Pro Ile Gln Lys Glu Thr Trp
385                 390                 395                 400

Glu Ala Trp Trp Thr Glu Tyr Trp Gln Ala Thr Trp Ile Pro Glu Trp
            405                 410                 415

Glu Phe Val Asn Thr Pro Pro Leu Val Lys Leu Trp Tyr Gln Leu Glu
        420                 425                 430

Lys Glu Pro Ile Val Gly Ala Glu Thr Phe Tyr Val Ala Gly Ala Ala
    435                 440                 445

Asn Arg Glu Thr Lys Leu Gly Lys Ala Gly Tyr Val Thr Asp Arg Gly
450                 455                 460

Arg Gln Lys Val Val Ser Leu Thr Asp Thr Thr Asn Gln Lys Thr Ala
465                 470                 475                 480

Leu Gln Ala Ile His Leu Ala Leu Gln Asp Ser Gly Leu Glu Val Asn
            485                 490                 495

Ile Val Thr Ala Ser Gln Tyr Ala Leu Gly Ile Ile Gln Ala Gln Pro
        500                 505                 510

Asp Lys Ser Glu Ser Glu Leu Val Ser Gln Ile Ile Glu Gln Leu Ile
    515                 520                 525

Lys Lys Glu Lys Val Tyr Leu Ala Trp Val Pro Ala His Lys Gly Ile
530                 535                 540

Gly Gly Asn Glu Gln Val Asp Lys Leu Val Ser Arg Gly Ile Arg Lys
545                 550                 555                 560

Val Leu Phe Leu Asp Gly Ile Asp Lys Ala Gln Glu Glu His Glu Lys
            565                 570                 575

Tyr His Ser Asn Trp Arg Ala Met Ala Ser Glu Phe Asn Leu Pro Pro
        580                 585                 590

Ile Val Ala Lys Glu Ile Val Ala Ser Cys Asp Lys Cys Gln Leu Lys
    595                 600                 605

Gly Glu Ala Ile His Gly Gln Val Asp Cys Ser Pro Gly Ile Trp Gln
610                 615                 620

Leu Ala Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
            645                 650                 655

Gln Glu Thr Ala Tyr Phe Leu Leu Lys Leu Ala Gly Arg Trp Pro Val
        660                 665                 670

Lys Thr Ile His Thr Ala Asn Gly Ser Asn Phe Thr Ser Ala Thr Val
    675                 680                 685

Lys Ala Ala Cys Trp Trp Ala Gly Ile Lys Gln Glu Phe Gly Ile Pro
690                 695                 700

Tyr Asn Pro Gln Ser Gln Gly Val Val Ala Ser Ile Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Glu Tyr Ser Ala Gly Glu Arg Ile Val Asp Ile Ile Ala Ser
        755                 760                 765

Asp Ile Gln Thr Lys Glu Leu Gln Lys Gln Ile Thr Lys Ile Gln Asn
    770                 775                 780

Phe Arg Val Tyr Tyr Arg Asp Ser Arg Asp Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
        835                 840                 845

Glu Asp
    850

<210> SEQ ID NO 18
<211> LENGTH: 851
<212> TYPE: PRT
<213> ORGANISM: Artificial Sequence
<220> FEATURE:
<223> OTHER INFORMATION: Synthetic Construct (Mos3 pol v3)

<400> SEQUENCE: 18

Met Ala Pro Ile Ser Pro Ile Asp Thr Val Pro Val Thr Leu Lys Pro
1               5                   10                  15

Gly Met Asp Gly Pro Lys Ile Lys Gln Trp Pro Leu Thr Glu Glu Lys
            20                  25                  30

Ile Lys Ala Leu Thr Glu Ile Cys Thr Glu Met Glu Lys Glu Gly Lys
        35                  40                  45

Ile Ser Arg Ile Gly Pro Glu Asn Pro Tyr Asn Thr Pro Val Phe Ala
    50                  55                  60

Ile Lys Lys Lys Asn Ser Thr Arg Trp Arg Lys Leu Val Asp Phe Arg
65                  70                  75                  80

Glu Leu Asn Lys Lys Thr Gln Asp Phe Trp Glu Val Gln Leu Gly Ile
                85                  90                  95

Pro His Pro Ala Gly Leu Lys Lys Lys Arg Ser Val Thr Val Leu Ala
            100                 105                 110

Val Gly Asp Ala Tyr Phe Ser Val Pro Leu Asp Lys Asp Phe Arg Lys
        115                 120                 125

Tyr Thr Ala Phe Thr Ile Pro Ser Val Asn Asn Glu Thr Pro Gly Val
    130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Lys Ile Leu Glu Pro Phe Arg Ala Gln
                165                 170                 175

Asn Pro Glu Ile Val Ile Tyr Gln Tyr Val Ala Ala Leu Tyr Val Gly
            180                 185                 190

Ser Asp Leu Glu Ile Glu Gln His Arg Thr Lys Ile Glu Glu Leu Arg
        195                 200                 205

Ala His Leu Leu Ser Trp Gly Phe Thr Thr Pro Asp Lys Lys His Gln
    210                 215                 220

-continued

Arg Glu Pro Pro Phe Leu Trp Met Gly Tyr Glu Leu His Pro Asp Arg
225                 230                 235                 240

Trp Thr Val Gln Pro Ile Glu Leu Pro Glu Lys Glu Ser Trp Thr Val
            245                 250                 255

Asn Asp Ile Gln Lys Leu Val Gly Lys Leu Asn Trp Ala Ser Gln Ile
            260                 265                 270

Tyr Pro Gly Ile Lys Val Lys Gln Leu Cys Arg Leu Leu Arg Gly Ala
            275                 280                 285

Lys Ala Leu Thr Glu Val Ile Pro Leu Thr Lys Glu Ala Glu Leu Glu
        290                 295                 300

Leu Ala Glu Asn Arg Glu Ile Leu Arg Glu Pro Val His Gly Val Tyr
305                 310                 315                 320

Tyr Asp Pro Ser Lys Asp Leu Val Ala Glu Ile Gln Lys Gln Gly Gln
            325                 330                 335

Asp Gln Trp Thr Tyr Gln Ile Tyr Gln Glu Pro Tyr Lys Asn Leu Lys
            340                 345                 350

Thr Gly Lys Tyr Ala Arg Lys Arg Ser Ala His Thr Asn Asp Val Arg
            355                 360                 365

Gln Leu Thr Glu Ala Val Gln Lys Ile Ala Leu Glu Ser Ile Val Ile
        370                 375                 380

Trp Gly Lys Ile Pro Lys Phe Arg Leu Pro Ile Gln Arg Glu Thr Trp
385                 390                 395                 400

Glu Thr Trp Trp Thr Glu Tyr Trp Gln Ala Thr Trp Ile Pro Asp Trp
                405                 410                 415

Glu Phe Val Asn Thr Pro Pro Leu Val Lys Leu Trp Tyr Gln Leu Glu
            420                 425                 430

Lys Glu Pro Ile Ala Gly Ala Glu Thr Phe Tyr Val Ala Gly Ala Ser
            435                 440                 445

Asn Arg Glu Thr Lys Ile Gly Lys Ala Gly Tyr Val Thr Asp Lys Gly
            450                 455                 460

Arg Gln Lys Val Val Ser Leu Thr Glu Thr Thr Asn Gln Lys Ala Ala
465                 470                 475                 480

Leu Gln Ala Ile Gln Leu Ala Leu Gln Asp Ser Gly Pro Glu Val Asn
            485                 490                 495

Ile Val Thr Ala Ser Gln Tyr Val Leu Gly Ile Ile Gln Ala Gln Pro
            500                 505                 510

Asp Arg Ser Glu Ser Glu Leu Val Asn Gln Ile Ile Glu Glu Leu Ile
            515                 520                 525

Lys Lys Glu Lys Val Tyr Leu Ser Trp Val Pro Ala His Lys Gly Ile
530                 535                 540

Gly Gly Asn Glu Gln Val Asp Lys Leu Val Ser Ala Gly Ile Arg Lys
545                 550                 555                 560

Ile Leu Phe Leu Asp Gly Ile Asp Lys Ala Gln Glu Glu His Glu Arg
            565                 570                 575

Tyr His Ser Asn Trp Arg Thr Met Ala Ser Asp Phe Asn Leu Pro Pro
            580                 585                 590

Ile Val Ala Lys Glu Ile Val Ala Asn Cys Asp Lys Cys Gln Leu Lys
            595                 600                 605

Gly Glu Ala Met His Gly Gln Val Asp Cys Ser Pro Gly Met Trp Gln
            610                 615                 620

Leu Ala Cys Thr His Leu Glu Gly Lys Ile Ile Ile Val Ala Val His
625                 630                 635                 640

Val Ala Ser Gly Tyr Met Glu Ala Glu Val Ile Pro Ala Glu Thr Gly

```
            645                 650                 655
Gln Glu Thr Ala Tyr Tyr Ile Leu Lys Leu Ala Gly Arg Trp Pro Val
            660                 665                 670
Lys Val Val His Thr Ala Asn Gly Ser Asn Phe Thr Ser Thr Thr Val
            675                 680                 685
Lys Ala Ala Cys Trp Trp Ala Asn Val Thr Gln Glu Phe Gly Ile Pro
            690                 695                 700
Tyr Asn Pro Gln Ser Gln Gly Val Ile Ala Ser Met Asn Lys Glu Leu
705                 710                 715                 720
Lys Lys Ile Ile Gly Gln Val Arg Glu Gln Ala Glu His Leu Lys Thr
            725                 730                 735
Ala Val Gln Met Ala Val Leu Ile His Asn Phe Lys Arg Arg Gly Gly
            740                 745                 750
Ile Gly Gly Tyr Ser Ala Gly Glu Arg Ile Val Asp Ile Ile Ala Thr
            755                 760                 765
Asp Ile Gln Thr Arg Glu Leu Gln Lys Gln Ile Lys Ile Gln Asn
            770                 775                 780
Phe Arg Val Tyr Phe Arg Asp Ser Arg Asp Pro Val Trp Lys Gly Pro
785                 790                 795                 800
Ala Lys Leu Leu Trp Lys Gly Glu Gly Ala Val Val Ile Gln Asp Asn
            805                 810                 815
Ser Glu Ile Lys Val Val Pro Arg Arg Lys Val Lys Ile Ile Arg Asp
            820                 825                 830
Tyr Gly Lys Gln Met Ala Gly Asp Asp Cys Val Ala Gly Arg Gln Asp
            835                 840                 845
Glu Asp Gln
    850

<210> SEQ ID NO 19
<211> LENGTH: 508
<212> TYPE: PRT
<213> ORGANISM: Artificial Sequence
<220> FEATURE:
<223> OTHER INFORMATION: Synthetic Construct (Mos3 gag)

<400> SEQUENCE: 19

Met Gly Ala Arg Ala Ser Val Leu Ser Gly Gly Lys Leu Asp Ala Trp
1               5                   10                  15
Glu Lys Ile Arg Leu Arg Pro Gly Gly Lys Lys Lys Tyr Lys Leu Lys
            20                  25                  30
His Ile Val Trp Ala Ser Arg Glu Leu Asp Arg Phe Ala Leu Asn Pro
        35                  40                  45
Gly Leu Leu Glu Thr Ala Glu Gly Cys Gln Gln Ile Ile Glu Gln Leu
    50                  55                  60
Gln Pro Ala Leu Gln Thr Gly Ser Glu Glu Leu Lys Ser Leu Tyr Asn
65                  70                  75                  80
Thr Val Ala Val Leu Tyr Cys Val His Gln Arg Ile Asp Val Lys Asp
                85                  90                  95
Thr Lys Glu Ala Leu Asp Lys Ile Glu Glu Ile Gln Asn Lys Ser Lys
            100                 105                 110
Gln Lys Thr Gln Gln Ala Ala Ala Asp Thr Gly Ser Ser Ser Lys Val
        115                 120                 125
Ser Gln Asn Tyr Pro Ile Val Gln Asn Ala Gln Gly Gln Met Val His
    130                 135                 140
Gln Ala Leu Ser Pro Arg Thr Leu Asn Ala Trp Val Lys Val Val Glu
```

```
            145                 150                 155                 160
        Glu Lys Gly Phe Asn Pro Glu Val Ile Pro Met Phe Ser Ala Leu Ala
                        165                 170                 175

Glu Gly Ala Thr Pro Gln Asp Leu Asn Met Met Leu Asn Ile Val Gly
                    180                 185                 190

Gly His Gln Ala Ala Met Gln Ile Leu Lys Asp Thr Ile Asn Glu Glu
                195                 200                 205

Ala Ala Asp Trp Asp Arg Leu His Pro Val His Ala Gly Pro Ile Pro
            210                 215                 220

Pro Gly Gln Met Arg Glu Pro Arg Gly Ser Asp Ile Ala Gly Thr Thr
        225                 230                 235                 240

Ser Thr Pro Gln Glu Gln Ile Gly Trp Met Thr Ser Asn Pro Pro Val
                        245                 250                 255

Pro Val Gly Glu Ile Tyr Lys Arg Trp Ile Ile Met Gly Leu Asn Lys
                    260                 265                 270

Ile Val Arg Met Tyr Ser Pro Val Ser Ile Leu Asp Ile Lys Gln Gly
                275                 280                 285

Pro Lys Glu Ser Phe Arg Asp Tyr Val Asp Arg Phe Phe Lys Val Leu
            290                 295                 300

Arg Ala Glu Gln Ala Thr Gln Glu Val Lys Asn Trp Met Thr Glu Thr
        305                 310                 315                 320

Leu Leu Ile Gln Asn Ala Asn Pro Asp Cys Lys Ser Ile Leu Arg Ala
                        325                 330                 335

Leu Gly Pro Gly Ala Ser Leu Glu Glu Met Met Thr Ala Cys Gln Gly
                    340                 345                 350

Val Gly Gly Pro Ser His Lys Ala Arg Ile Leu Ala Glu Ala Met Ser
                355                 360                 365

Gln Ala Asn Asn Thr Asn Ile Met Met Gln Arg Gly Asn Phe Lys Gly
            370                 375                 380

Gln Lys Arg Ile Lys Cys Phe Asn Cys Gly Lys Glu Gly His Leu Ala
        385                 390                 395                 400

Arg Asn Cys Arg Ala Pro Arg Lys Arg Gly Cys Trp Lys Cys Gly Arg
                        405                 410                 415

Glu Gly His Gln Met Lys Asp Cys Asn Glu Arg Gln Ala Asn Phe Leu
                    420                 425                 430

Gly Lys Ile Trp Pro Ser Ser Lys Gly Arg Pro Gly Asn Phe Pro Gln
                435                 440                 445

Ser Arg Pro Glu Pro Thr Ala Pro Leu Glu Pro Thr Ala Pro Pro Ala
        450                 455                 460

Glu Pro Thr Ala Pro Pro Ala Glu Ser Phe Gly Phe Gly Glu Glu Ile
        465                 470                 475                 480

Thr Pro Ser Pro Lys Gln Glu Gln Lys Asp Arg Glu Pro Leu Thr Ser
                        485                 490                 495

Leu Lys Ser Leu Phe Gly Ser Asp Pro Leu Leu Gln
                    500                 505

<210> SEQ ID NO 20
<211> LENGTH: 206
<212> TYPE: PRT
<213> ORGANISM: Artificial Sequence
<220> FEATURE:
<223> OTHER INFORMATION: Synthetic Construct ((Mos1 nef) (G to A to
      delete myristylation site))

<400> SEQUENCE: 20
```

Met Ala Gly Lys Trp Ser Lys Ser Ser Val Gly Trp Pro Ala Ile
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Asn Asn Ala Asp Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
                100                 105                 110

Trp Val Tyr His Thr Gln Gly Tyr Phe Pro Asp Trp Gln Asn Tyr Thr
                115                 120                 125

Pro Gly Pro Gly Ile Arg Tyr Pro Leu Thr Phe Gly Trp Cys Phe Lys
            130                 135                 140

Leu Val Pro Val Glu Pro Glu Lys Ile Glu Glu Ala Asn Glu Gly Glu
145                 150                 155                 160

Asn Asn Ser Leu Leu His Pro Met Ser Gln His Gly Met Asp Asp Pro
                165                 170                 175

Glu Lys Glu Val Leu Met Trp Lys Phe Asp Ser Arg Leu Ala Phe His
            180                 185                 190

His Met Ala Arg Glu Leu His Pro Glu Tyr Tyr Lys Asp Cys
        195                 200                 205

<210> SEQ ID NO 21
<211> LENGTH: 206
<212> TYPE: PRT
<213> ORGANISM: Artificial Sequence
<220> FEATURE:
<223> OTHER INFORMATION: Synthetic Construct ((Mos2 nef) (G to A to
      delete myristylation))

<400> SEQUENCE: 21

Met Ala Gly Lys Trp Ser Lys Ser Ser Ile Val Gly Trp Pro Ala Val
1               5                   10                  15

Arg Glu Arg Ile Arg Arg Ala Glu Pro Ala Ala Glu Gly Val Gly Ala
            20                  25                  30

Ala Ser Gln Asp Leu Asp Lys Tyr Gly Ala Leu Thr Ser Ser Asn Thr
        35                  40                  45

Ala Ala Thr Asn Ala Asp Cys Ala Trp Leu Glu Ala Gln Glu Asp Glu
    50                  55                  60

Glu Val Gly Phe Pro Val Lys Pro Gln Val Pro Leu Arg Pro Met Thr
65                  70                  75                  80

Tyr Lys Ala Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
                100                 105                 110

Trp Val Tyr Asn Thr Gln Gly Phe Phe Pro Asp Trp Gln Asn Tyr Thr
                115                 120                 125

Pro Gly Pro Gly Val Arg Tyr Pro Leu Thr Phe Gly Trp Cys Phe Lys
            130                 135                 140

Leu Val Pro Val Asp Pro Arg Glu Val Glu Glu Ala Asn Lys Gly Glu
145                 150                 155                 160

Asn Asn Cys Leu Leu His Pro Met Asn Leu His Gly Met Asp Asp Pro
            165                 170                 175

Glu Arg Glu Val Leu Val Trp Arg Phe Asp Ser Arg Leu Ala Phe His
        180                 185                 190

His Met Ala Arg Glu Lys His Pro Glu Tyr Tyr Lys Asn Cys
        195                 200                 205

<210> SEQ ID NO 22
<211> LENGTH: 208
<212> TYPE: PRT
<213> ORGANISM: Artificial Sequence
<220> FEATURE:
<223> OTHER INFORMATION: Synthetic Construct (Mos3 nef)

<400> SEQUENCE: 22

Met Ala Gly Lys Trp Ser Lys Arg Ser Val Val Gly Trp Pro Ala Val
1               5                   10                  15

Arg Glu Arg Met Arg Arg Thr Glu Pro Ala Ala Glu Gly Val Gly Ala
            20                  25                  30

Val Ser Gln Asp Leu Asp Lys His Gly Ala Leu Thr Ser Ser Asn Thr
        35                  40                  45

Ala His Asn Asn Ala Asp Cys Ala Trp Leu Gln Ala Gln Glu Glu Glu
    50                  55                  60

Glu Glu Val Gly Phe Pro Val Arg Pro Gln Val Pro Val Arg Pro Met
65                  70                  75                  80

Thr Tyr Lys Ala Ala Val Asp Leu Ser His Phe Leu Lys Glu Lys Gly
                85                  90                  95

Gly Leu Glu Gly Leu Ile His Ser Gln Lys Arg Gln Glu Ile Leu Asp
            100                 105                 110

Leu Trp Val Tyr His Thr Gln Gly Phe Phe Pro Asp Trp His Asn Tyr
        115                 120                 125

Thr Pro Gly Pro Gly Thr Arg Phe Pro Leu Thr Phe Gly Trp Cys Tyr
    130                 135                 140

Lys Leu Val Pro Val Asp Pro Lys Glu Val Glu Glu Ala Asn Glu Gly
145                 150                 155                 160

Glu Asn Asn Cys Leu Leu His Pro Met Ser Gln His Gly Met Glu Asp
                165                 170                 175

Glu Asp Arg Glu Val Leu Lys Trp Lys Phe Asp Ser Ser Leu Ala Arg
            180                 185                 190

Arg His Met Ala Arg Glu Leu His Pro Glu Phe Tyr Lys Asp Cys Leu
        195                 200                 205

<210> SEQ ID NO 23
<211> LENGTH: 705
<212> TYPE: PRT
<213> ORGANISM: Artificial Sequence
<220> FEATURE:
<223> OTHER INFORMATION: Synthetic Construct (Mosaic gagnef1)

<400> SEQUENCE: 23

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu

```
                50                  55                  60
Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Glu Lys Ile Glu Glu Gln Asn Lys Ser Lys
                100                 105                 110

Lys Lys Ala Gln Gln Ala Ala Ala Asp Thr Gly Asn Ser Ser Gln Val
                115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Val Ser Ile Leu Asp Ile Arg Gln Gly
                275                 280                 285

Pro Lys Glu Pro Phe Arg Asp Tyr Val Asp Arg Phe Tyr Lys Thr Leu
        290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
        370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Glu Glu Ser Phe Arg
        450                 455                 460

Phe Gly Glu Glu Thr Thr Thr Pro Ser Gln Lys Gln Glu Pro Ile Asp
465                 470                 475                 480
```

-continued

```
Lys Glu Met Tyr Pro Leu Ala Ser Leu Lys Ser Leu Phe Gly Asn Asp
            485                 490                 495

Pro Ser Ser Gln Ala Gly Lys Trp Ser Lys Ser Ser Val Val Gly Trp
        500                 505                 510

Pro Ala Ile Arg Glu Arg Met Arg Arg Ala Glu Pro Ala Ala Asp Gly
        515                 520                 525

Val Gly Ala Val Ser Arg Asp Leu Glu Lys His Gly Ala Ile Thr Ser
    530                 535                 540

Ser Asn Thr Ala Ala Asn Ala Asp Cys Ala Trp Leu Glu Ala Gln
545                 550                 555                 560

Glu Glu Glu Glu Val Gly Phe Pro Val Arg Pro Gln Val Pro Leu Arg
                565                 570                 575

Pro Met Thr Tyr Lys Gly Ala Leu Asp Leu Ser His Phe Leu Lys Glu
            580                 585                 590

Lys Gly Gly Leu Glu Gly Leu Ile Tyr Ser Gln Lys Arg Gln Asp Ile
        595                 600                 605

Leu Asp Leu Trp Val Tyr His Thr Gln Gly Tyr Phe Pro Asp Trp Gln
    610                 615                 620

Asn Tyr Thr Pro Gly Pro Gly Ile Arg Tyr Pro Leu Thr Phe Gly Trp
625                 630                 635                 640

Cys Phe Lys Leu Val Pro Val Glu Pro Glu Lys Ile Glu Glu Ala Asn
                645                 650                 655

Glu Gly Glu Asn Asn Ser Leu Leu His Pro Met Ser Gln His Gly Met
            660                 665                 670

Asp Asp Pro Glu Lys Glu Val Leu Met Trp Lys Phe Asp Ser Arg Leu
        675                 680                 685

Ala Phe His His Met Ala Arg Glu Leu His Pro Glu Tyr Tyr Lys Asp
    690                 695                 700

Cys
705

<210> SEQ ID NO 24
<211> LENGTH: 696
<212> TYPE: PRT
<213> ORGANISM: Artificial Sequence
<220> FEATURE:
<223> OTHER INFORMATION: Synthetic Construct (Mosaic gagnef2)

<400> SEQUENCE: 24

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125
```

```
Tyr Pro Ile Val Gln Asn Leu Gln Gly Gln Met Val His Gln Pro Ile
    130                 135                 140
Ser Pro Arg Thr Leu Asn Ala Trp Val Lys Val Ile Glu Glu Lys Ala
145                 150                 155                 160
Phe Ser Pro Glu Val Ile Pro Met Phe Thr Ala Leu Ser Glu Gly Ala
                165                 170                 175
Thr Pro Gln Asp Leu Asn Thr Met Leu Asn Thr Val Gly Gly His Gln
            180                 185                 190
Ala Ala Met Gln Met Leu Lys Asp Thr Ile Asn Glu Glu Ala Ala Glu
        195                 200                 205
Trp Asp Arg Leu His Pro Val His Ala Gly Pro Val Ala Pro Gly Gln
210                 215                 220
Met Arg Glu Pro Arg Gly Ser Asp Ile Ala Gly Thr Thr Ser Asn Leu
225                 230                 235                 240
Gln Glu Gln Ile Ala Trp Met Thr Ser Asn Pro Pro Ile Pro Val Gly
                245                 250                 255
Asp Ile Tyr Lys Arg Trp Ile Ile Leu Gly Leu Asn Lys Ile Val Arg
            260                 265                 270
Met Tyr Ser Pro Thr Ser Ile Leu Asp Ile Lys Gln Gly Pro Lys Glu
        275                 280                 285
Pro Phe Arg Asp Tyr Val Asp Arg Phe Phe Lys Thr Leu Arg Ala Glu
290                 295                 300
Gln Ala Thr Gln Asp Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
Gly Ala Thr Leu Glu Glu Met Met Thr Ala Cys Gln Gly Val Gly Gly
            340                 345                 350
Pro Ser His Lys Ala Arg Val Leu Ala Glu Ala Met Ser Gln Thr Asn
        355                 360                 365
Ser Thr Ile Leu Met Gln Arg Ser Asn Phe Lys Gly Ser Lys Arg Ile
370                 375                 380
Val Lys Cys Phe Asn Cys Gly Lys Glu Gly His Ile Ala Arg Asn Cys
385                 390                 395                 400
Arg Ala Pro Arg Lys Lys Gly Cys Trp Lys Cys Gly Lys Glu Gly His
                405                 410                 415
Gln Met Lys Asp Cys Thr Glu Arg Gln Ala Asn Phe Leu Gly Lys Ile
            420                 425                 430
Trp Pro Ser His Lys Gly Arg Pro Gly Asn Phe Leu Gln Ser Arg Pro
        435                 440                 445
Glu Pro Thr Ala Pro Ala Glu Ser Phe Arg Phe Glu Glu Thr Thr
450                 455                 460
Pro Ala Pro Lys Gln Glu Pro Lys Asp Arg Glu Pro Leu Thr Ser Leu
465                 470                 475                 480
Arg Ser Leu Phe Gly Ser Asp Pro Leu Ser Gln Ala Gly Lys Trp Ser
                485                 490                 495
Lys Ser Ser Ile Val Gly Trp Pro Ala Val Arg Glu Arg Ile Arg Arg
            500                 505                 510
Ala Glu Pro Ala Ala Glu Gly Val Gly Ala Ala Ser Gln Asp Leu Asp
        515                 520                 525
Lys Tyr Gly Ala Leu Thr Ser Ser Asn Thr Ala Ala Thr Asn Ala Asp
530                 535                 540
```

```
Cys Ala Trp Leu Glu Ala Gln Glu Asp Glu Glu Val Gly Phe Pro Val
545                 550                 555                 560

Lys Pro Gln Val Pro Leu Arg Pro Met Thr Tyr Lys Ala Ala Phe Asp
            565                 570                 575

Leu Ser Phe Phe Leu Lys Glu Lys Gly Gly Leu Asp Gly Leu Ile Tyr
        580                 585                 590

Ser Lys Lys Arg Gln Glu Ile Leu Asp Leu Trp Val Tyr Asn Thr Gln
    595                 600                 605

Gly Phe Phe Pro Asp Trp Gln Asn Tyr Thr Pro Gly Pro Gly Val Arg
610                 615                 620

Tyr Pro Leu Thr Phe Gly Trp Cys Phe Lys Leu Val Pro Val Asp Pro
625                 630                 635                 640

Arg Glu Val Glu Glu Ala Asn Lys Gly Glu Asn Asn Cys Leu Leu His
            645                 650                 655

Pro Met Asn Leu His Gly Met Asp Asp Pro Glu Arg Glu Val Leu Val
        660                 665                 670

Trp Arg Phe Asp Ser Arg Leu Ala Phe His His Met Ala Arg Glu Lys
    675                 680                 685

His Pro Glu Tyr Tyr Lys Asn Cys
690                 695

<210> SEQ ID NO 25
<211> LENGTH: 1341
<212> TYPE: PRT
<213> ORGANISM: Artificial Sequence
<220> FEATURE:
<223> OTHER INFORMATION: Synthetic Construct (Mosaic gag pol2 v3)

<400> SEQUENCE: 25

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205
```

```
Trp Asp Arg Leu His Pro Val His Ala Gly Pro Val Ala Pro Gly Gln
210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
            245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
            485                 490                 495

Pro Ile Glu Thr Val Pro Val Lys Leu Lys Pro Gly Met Asp Gly Pro
            500                 505                 510

Lys Val Lys Gln Trp Pro Leu Thr Glu Glu Lys Ile Lys Ala Leu Val
        515                 520                 525

Glu Ile Cys Thr Glu Met Glu Lys Glu Gly Lys Ile Ser Lys Ile Gly
530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
            580                 585                 590

Leu Lys Lys Lys Lys Ser Val Thr Val Leu Ala Val Gly Asp Ala Tyr
        595                 600                 605

Phe Ser Val Pro Leu Asp Glu Asp Phe Arg Lys Tyr Thr Ala Phe Thr
610                 615                 620

Ile Pro Ser Ile Asn Asn Glu Thr Pro Gly Ile Arg Tyr Gln Tyr Asn
```

-continued

```
            625                 630                 635                 640
Val Leu Pro Gln Gly Trp Lys Gly Ser Pro Ala Ile Phe Gln Ser Ser
                        645                 650                 655

Met Thr Lys Ile Leu Glu Pro Phe Arg Lys Gln Asn Pro Asp Ile Val
                660                 665                 670

Ile Tyr Gln Tyr Met Ala Ala Leu Tyr Val Gly Ser Asp Leu Glu Ile
                675                 680                 685

Gly Gln His Arg Thr Lys Ile Glu Glu Leu Arg Gln His Leu Leu Arg
        690                 695                 700

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
                    725                 730                 735

Ile Val Leu Pro Glu Lys Asp Ser Trp Thr Val Asn Asp Ile Gln Lys
                740                 745                 750

Leu Val Gly Lys Leu Asn Trp Ala Ser Gln Ile Tyr Ala Gly Ile Lys
                755                 760                 765

Val Lys Gln Leu Cys Lys Leu Leu Arg Gly Thr Lys Ala Leu Thr Glu
        770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
                    805                 810                 815

Asp Leu Ile Ala Glu Ile Gln Lys Gln Gly Gln Gly Gln Trp Thr Tyr
                820                 825                 830

Gln Ile Tyr Gln Glu Pro Phe Lys Asn Leu Lys Thr Gly Lys Tyr Ala
                835                 840                 845

Arg Met Arg Gly Ala His Thr Asn Asp Val Lys Gln Leu Thr Glu Ala
        850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                    885                 890                 895

Glu Tyr Trp Gln Ala Thr Trp Ile Pro Glu Trp Glu Phe Val Asn Thr
                900                 905                 910

Pro Pro Leu Val Lys Leu Trp Tyr Gln Leu Glu Lys Glu Pro Ile Val
                915                 920                 925

Gly Ala Glu Thr Phe Tyr Val Ala Gly Ala Ala Asn Arg Glu Thr Lys
        930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                    965                 970                 975

Leu Ala Leu Gln Asp Ser Gly Leu Glu Val Asn Ile Val Thr Ala Ser
                980                 985                 990

Gln Tyr Ala Leu Gly Ile Ile Gln Ala Gln Pro Asp Lys Ser Glu Ser
                995                 1000                1005

Glu Leu Val Ser Gln Ile Ile Glu Gln Leu Ile Lys Lys Glu Lys
        1010                1015                1020

Val Tyr Leu Ala Trp Val Pro Ala His Lys Gly Ile Gly Gly Asn
        1025                1030                1035

Glu Gln Val Asp Lys Leu Val Ser Arg Gly Ile Arg Lys Val Leu
        1040                1045                1050
```

```
Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
    1190                1195                1200

Val Ala Ser Ile Asn Lys Glu Leu Lys Lys Ile Ile Gly Gln Val
    1205                1210                1215

Arg Asp Gln Ala Glu His Leu Lys Thr Ala Val Gln Met Ala Val
    1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
    1250                1255                1260

Lys Glu Leu Gln Lys Gln Ile Thr Lys Ile Gln Asn Phe Arg Val
    1265                1270                1275

Tyr Tyr Arg Asp Ser Arg Asp Pro Leu Trp Lys Gly Pro Ala Lys
    1280                1285                1290

Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
    1310                1315                1320

Tyr Gly Lys Gln Met Ala Gly Asp Asp Cys Val Ala Ser Arg Gln
    1325                1330                1335

Asp Glu Asp
    1340

<210> SEQ ID NO 26
<211> LENGTH: 1359
<212> TYPE: PRT
<213> ORGANISM: Artificial Sequence
<220> FEATURE:
<223> OTHER INFORMATION: Synthetic Construct (Mos3 gag-pol v3)

<400> SEQUENCE: 26

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Asp Arg Phe Ala Leu Asn Pro
            35                  40                  45
```

```
Gly Leu Leu Glu Thr Ala Gly Cys Gln Gln Ile Ile Glu Gln Leu
     50                  55                  60

Gln Pro Ala Leu Gln Thr Gly Ser Glu Glu Leu Lys Ser Leu Tyr Asn
 65                  70                  75                  80

Thr Val Ala Val Leu Tyr Cys Val His Gln Arg Ile Asp Val Lys Asp
                 85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Ser Ser Ser Lys Val
        115                 120                 125

Ser Gln Asn Tyr Pro Ile Val Gln Asn Ala Gln Gly Gln Met Val His
130                 135                 140

Gln Ala Leu Ser Pro Arg Thr Leu Asn Ala Trp Val Lys Val Val Glu
145                 150                 155                 160

Glu Lys Gly Phe Asn Pro Glu Val Ile Pro Met Phe Ser Ala Leu Ala
                165                 170                 175

Glu Gly Ala Thr Pro Gln Asp Leu Asn Met Met Leu Asn Ile Val Gly
            180                 185                 190

Gly His Gln Ala Ala Met Gln Ile Leu Lys Asp Thr Ile Asn Glu Glu
        195                 200                 205

Ala Ala Asp Trp Asp Arg Leu His Pro Val His Ala Gly Pro Ile Pro
    210                 215                 220

Pro Gly Gln Met Arg Glu Pro Arg Gly Ser Asp Ile Ala Gly Thr Thr
225                 230                 235                 240

Ser Thr Pro Gln Glu Gln Ile Gly Trp Met Thr Ser Asn Pro Pro Val
                245                 250                 255

Pro Val Gly Glu Ile Tyr Lys Arg Trp Ile Ile Met Gly Leu Asn Lys
            260                 265                 270

Ile Val Arg Met Tyr Ser Pro Val Ser Ile Leu Asp Ile Lys Gln Gly
        275                 280                 285

Pro Lys Glu Ser Phe Arg Asp Tyr Val Asp Arg Phe Phe Lys Val Leu
    290                 295                 300

Arg Ala Glu Gln Ala Thr Gln Glu Val Lys Asn Trp Met Thr Glu Thr
305                 310                 315                 320

Leu Leu Ile Gln Asn Ala Asn Pro Asp Cys Lys Ser Ile Leu Arg Ala
                325                 330                 335

Leu Gly Pro Gly Ala Ser Leu Glu Glu Met Met Thr Ala Cys Gln Gly
            340                 345                 350

Val Gly Gly Pro Ser His Lys Ala Arg Ile Leu Ala Glu Ala Met Ser
        355                 360                 365

Gln Ala Asn Asn Thr Asn Ile Met Met Gln Arg Gly Asn Phe Lys Gly
    370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Arg Gly Cys Trp Lys Cys Gly Arg
                405                 410                 415

Glu Gly His Gln Met Lys Asp Cys Asn Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Leu Glu Pro Thr Ala Pro Pro Ala
450                 455                 460
```

```
Glu Pro Thr Ala Pro Ala Glu Ser Phe Gly Phe Gly Glu Ile
465                 470                 475                 480

Thr Pro Ser Pro Lys Gln Glu Gln Lys Asp Arg Glu Pro Leu Thr Ser
            485                 490                 495

Leu Lys Ser Leu Phe Gly Ser Asp Pro Leu Leu Gln Met Ala Pro Ile
            500                 505                 510

Ser Pro Ile Asp Thr Val Pro Val Thr Leu Lys Pro Gly Met Asp Gly
            515                 520                 525

Pro Lys Ile Lys Gln Trp Pro Leu Thr Glu Glu Lys Ile Lys Ala Leu
            530                 535                 540

Thr Glu Ile Cys Thr Glu Met Glu Lys Glu Gly Lys Ile Ser Arg Ile
545                 550                 555                 560

Gly Pro Glu Asn Pro Tyr Asn Thr Pro Val Phe Ala Ile Lys Lys Lys
            565                 570                 575

Asn Ser Thr Arg Trp Arg Lys Leu Val Asp Phe Arg Glu Leu Asn Lys
            580                 585                 590

Lys Thr Gln Asp Phe Trp Glu Val Gln Leu Gly Ile Pro His Pro Ala
            595                 600                 605

Gly Leu Lys Lys Lys Arg Ser Val Thr Val Leu Ala Val Gly Asp Ala
            610                 615                 620

Tyr Phe Ser Val Pro Leu Asp Lys Asp Phe Arg Lys Tyr Thr Ala Phe
625                 630                 635                 640

Thr Ile Pro Ser Val Asn Asn Glu Thr Pro Gly Val Arg Tyr Gln Tyr
            645                 650                 655

Asn Val Leu Pro Gln Gly Trp Lys Gly Ser Pro Ala Ile Phe Gln Cys
            660                 665                 670

Ser Met Thr Lys Ile Leu Glu Pro Phe Arg Ala Gln Asn Pro Glu Ile
            675                 680                 685

Val Ile Tyr Gln Tyr Val Ala Ala Leu Tyr Val Gly Ser Asp Leu Glu
            690                 695                 700

Ile Glu Gln His Arg Thr Lys Ile Glu Glu Leu Arg Ala His Leu Leu
705                 710                 715                 720

Ser Trp Gly Phe Thr Thr Pro Asp Lys Lys His Gln Arg Glu Pro Pro
            725                 730                 735

Phe Leu Trp Met Gly Tyr Glu Leu His Pro Asp Arg Trp Thr Val Gln
            740                 745                 750

Pro Ile Glu Leu Pro Glu Lys Glu Ser Trp Thr Val Asn Asp Ile Gln
            755                 760                 765

Lys Leu Val Gly Lys Leu Asn Trp Ala Ser Gln Ile Tyr Pro Gly Ile
            770                 775                 780

Lys Val Lys Gln Leu Cys Arg Leu Leu Arg Gly Ala Lys Ala Leu Thr
785                 790                 795                 800

Glu Val Ile Pro Leu Thr Lys Glu Ala Glu Leu Glu Leu Ala Glu Asn
            805                 810                 815

Arg Glu Ile Leu Arg Glu Pro Val His Gly Val Tyr Tyr Asp Pro Ser
            820                 825                 830

Lys Asp Leu Val Ala Glu Ile Gln Lys Gln Gly Gln Asp Gln Trp Thr
            835                 840                 845

Tyr Gln Ile Tyr Gln Glu Pro Tyr Lys Asn Leu Lys Thr Gly Lys Tyr
            850                 855                 860

Ala Arg Lys Arg Ser Ala His Thr Asn Asp Val Arg Gln Leu Thr Glu
865                 870                 875                 880

Ala Val Gln Lys Ile Ala Leu Glu Ser Ile Val Ile Trp Gly Lys Ile
```

```
                885                 890                 895
Pro Lys Phe Arg Leu Pro Ile Gln Arg Glu Thr Trp Glu Thr Trp Trp
                    900                 905                 910

Thr Glu Tyr Trp Gln Ala Thr Trp Ile Pro Asp Trp Glu Phe Val Asn
            915                 920                 925

Thr Pro Pro Leu Val Lys Leu Trp Tyr Gln Leu Glu Lys Glu Pro Ile
            930                 935                 940

Ala Gly Ala Glu Thr Phe Tyr Val Ala Gly Ala Ser Asn Arg Glu Thr
945                 950                 955                 960

Lys Ile Gly Lys Ala Gly Tyr Val Thr Asp Lys Gly Arg Gln Lys Val
                965                 970                 975

Val Ser Leu Thr Glu Thr Thr Asn Gln Lys Ala Ala Leu Gln Ala Ile
                980                 985                 990

Gln Leu Ala Leu Gln Asp Ser Gly Pro Glu Val Asn Ile Val Thr Ala
                995                1000                1005

Ser Gln Tyr Val Leu Gly Ile Ile Gln Ala Gln Pro Asp Arg Ser
    1010                1015                1020

Glu Ser Glu Leu Val Asn Gln Ile Ile Glu Glu Leu Ile Lys Lys
    1025                1030                1035

Glu Lys Val Tyr Leu Ser Trp Val Pro Ala His Lys Gly Ile Gly
    1040                1045                1050

Gly Asn Glu Gln Val Asp Lys Leu Val Ser Ala Gly Ile Arg Lys
    1055                1060                1065

Ile Leu Phe Leu Asp Gly Ile Asp Lys Ala Gln Glu Glu His Glu
    1070                1075                1080

Arg Tyr His Ser Asn Trp Arg Thr Met Ala Ser Asp Phe Asn Leu
    1085                1090                1095

Pro Pro Ile Val Ala Lys Glu Ile Val Ala Asn Cys Asp Lys Cys
    1100                1105                1110

Gln Leu Lys Gly Glu Ala Met His Gly Gln Val Asp Cys Ser Pro
    1115                1120                1125

Gly Met Trp Gln Leu Ala Cys Thr His Leu Glu Gly Lys Ile Ile
    1130                1135                1140

Ile Val Ala Val His Val Ala Ser Gly Tyr Met Glu Ala Glu Val
    1145                1150                1155

Ile Pro Ala Glu Thr Gly Gln Glu Thr Ala Tyr Tyr Ile Leu Lys
    1160                1165                1170

Leu Ala Gly Arg Trp Pro Val Lys Val Val His Thr Ala Asn Gly
    1175                1180                1185

Ser Asn Phe Thr Ser Thr Thr Val Lys Ala Ala Cys Trp Trp Ala
    1190                1195                1200

Asn Val Thr Gln Glu Phe Gly Ile Pro Tyr Asn Pro Gln Ser Gln
    1205                1210                1215

Gly Val Ile Ala Ser Met Asn Lys Glu Leu Lys Lys Ile Ile Gly
    1220                1225                1230

Gln Val Arg Glu Gln Ala Glu His Leu Lys Thr Ala Val Gln Met
    1235                1240                1245

Ala Val Leu Ile His Asn Phe Lys Arg Arg Gly Gly Ile Gly Gly
    1250                1255                1260

Tyr Ser Ala Gly Glu Arg Ile Val Asp Ile Ile Ala Thr Asp Ile
    1265                1270                1275

Gln Thr Arg Glu Leu Gln Lys Gln Ile Ile Lys Ile Gln Asn Phe
    1280                1285                1290
```

```
Arg Val Tyr Phe Arg Asp Ser Arg Asp Pro Val Trp Lys Gly Pro
    1295                1300                1305

Ala Lys Leu Leu Trp Lys Gly Glu Gly Ala Val Ile Gln Asp
    1310                1315                1320

Asn Ser Glu Ile Lys Val Val Pro Arg Arg Lys Val Lys Ile Ile
1325                1330                1335

Arg Asp Tyr Gly Lys Gln Met Ala Gly Asp Asp Cys Val Ala Gly
    1340                1345                1350

Arg Gln Asp Glu Asp Gln
    1355

<210> SEQ ID NO 27
<211> LENGTH: 1497
<212> TYPE: PRT
<213> ORGANISM: Artificial Sequence
<220> FEATURE:
<223> OTHER INFORMATION: Synthetic Construct (Mosaic gagpol1 v4)

<400> SEQUENCE: 27

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285
```

```
Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Arg Glu Asn Leu Ala Phe Gln Gln Gly Glu Ala Arg
            500                 505                 510

Glu Phe Pro Ser Glu Gln Thr Arg Ala Asn Ser Pro Thr Ser Arg Glu
    515                 520                 525

Leu Gln Val Arg Gly Asp Asn Pro His Ser Glu Ala Gly Ala Glu Arg
530                 535                 540

Gln Gly Thr Leu Asn Phe Pro Gln Ile Thr Leu Trp Gln Arg Pro Leu
545                 550                 555                 560

Val Ser Ile Lys Val Gly Gly Gln Ile Arg Glu Ala Leu Leu Ala Thr
                565                 570                 575

Gly Ala Asp Asp Thr Val Leu Glu Asp Ile Asn Leu Pro Gly Lys Trp
            580                 585                 590

Lys Pro Lys Met Ile Gly Gly Ile Gly Gly Phe Ile Lys Val Gly Gln
    595                 600                 605

Tyr Asp Gln Ile Leu Ile Glu Ile Cys Gly Lys Lys Ala Ile Gly Thr
610                 615                 620

Val Leu Val Gly Pro Thr Pro Val Asn Ile Ile Gly Arg Asn Met Leu
625                 630                 635                 640

Thr Gln Leu Gly Cys Thr Leu Asn Phe Pro Ile Ser Pro Ile Glu Thr
                645                 650                 655

Val Pro Val Lys Leu Lys Pro Gly Met Asp Gly Pro Arg Val Lys Gln
            660                 665                 670

Trp Pro Leu Thr Glu Glu Lys Ile Lys Ala Leu Thr Ala Ile Cys Glu
    675                 680                 685

Glu Met Glu Lys Glu Gly Lys Ile Thr Lys Ile Gly Pro Glu Asn Pro
690                 695                 700
```

```
Tyr Asn Thr Pro Val Phe Ala Ile Lys Lys Lys Asp Ser Thr Lys Trp
705                 710                 715                 720

Arg Lys Leu Val Asp Phe Arg Glu Leu Asn Lys Arg Thr Gln Asp Phe
            725                 730                 735

Trp Glu Val Gln Leu Gly Ile Pro His Pro Ala Gly Leu Lys Lys Lys
        740                 745                 750

Lys Ser Val Thr Val Leu Asp Val Gly Asp Ala Tyr Phe Ser Val Pro
    755                 760                 765

Leu Asp Glu Gly Phe Arg Lys Tyr Thr Ala Phe Thr Ile Pro Ser Thr
770                 775                 780

Asn Asn Glu Thr Pro Gly Ile Arg Tyr Gln Tyr Asn Val Leu Pro Gln
785                 790                 795                 800

Gly Trp Lys Gly Ser Pro Ala Ile Phe Gln Cys Ser Met Thr Arg Ile
            805                 810                 815

Leu Glu Pro Phe Arg Ala Lys Asn Pro Glu Ile Val Ile Tyr Gln Tyr
        820                 825                 830

Met Asp His Leu Tyr Val Gly Ser Asp Leu Glu Ile Gly Gln His Arg
    835                 840                 845

Ala Lys Ile Glu Glu Leu Arg Glu His Leu Leu Lys Trp Gly Phe Thr
850                 855                 860

Thr Pro Asp Lys Lys His Gln Lys Glu Pro Pro Phe Leu Trp Met Gly
865                 870                 875                 880

Tyr Glu Leu His Pro Asp Lys Trp Thr Val Gln Pro Ile Gln Leu Pro
            885                 890                 895

Glu Lys Asp Ser Trp Thr Val Asn Asp Ile Gln Lys Leu Val Gly Lys
        900                 905                 910

Leu Asn Trp Ala Ser Gln Ile Tyr Pro Gly Ile Lys Val Arg Gln Leu
    915                 920                 925

Cys Lys Leu Leu Arg Gly Ala Lys Ala Leu Thr Asp Ile Val Pro Leu
930                 935                 940

Thr Glu Glu Ala Glu Leu Glu Leu Ala Glu Asn Arg Glu Ile Leu Lys
945                 950                 955                 960

Glu Pro Val His Gly Val Tyr Tyr Asp Pro Ser Lys Asp Leu Ile Ala
            965                 970                 975

Glu Ile Gln Lys Gln Gly His Asp Gln Trp Thr Tyr Gln Ile Tyr Gln
        980                 985                 990

Glu Pro Phe Lys Asn Leu Lys Thr Gly Lys Tyr Ala Lys Met Arg Thr
    995                 1000                1005

Ala His Thr Asn Asp Val Lys Gln Leu Thr Glu Ala Val Gln Lys
1010                1015                1020

Ile Ala Met Glu Ser Ile Val Ile Trp Gly Lys Thr Pro Lys Phe
1025                1030                1035

Arg Leu Pro Ile Gln Lys Glu Thr Trp Glu Thr Trp Trp Thr Asp
1040                1045                1050

Tyr Trp Gln Ala Thr Trp Ile Pro Glu Trp Glu Phe Val Asn Thr
1055                1060                1065

Pro Pro Leu Val Lys Leu Trp Tyr Gln Leu Glu Lys Asp Pro Ile
1070                1075                1080

Ala Gly Val Glu Thr Phe Tyr Val Asp Gly Ala Ala Asn Arg Glu
1085                1090                1095

Thr Lys Leu Gly Lys Ala Gly Tyr Val Thr Asp Arg Gly Arg Gln
1100                1105                1110

Lys Ile Val Ser Leu Thr Glu Thr Thr Asn Gln Lys Thr Glu Leu
```

```
            1115                1120                1125

Gln Ala Ile Tyr Leu Ala Leu Gln Asp Ser Gly Ser Glu Val Asn
        1130                1135                1140

Ile Val Thr Asp Ser Gln Tyr Ala Leu Gly Ile Ile Gln Ala Gln
        1145                1150                1155

Pro Asp Lys Ser Glu Ser Glu Leu Val Asn Gln Ile Ile Glu Gln
        1160                1165                1170

Leu Ile Lys Lys Glu Arg Val Tyr Leu Ser Trp Val Pro Ala His
        1175                1180                1185

Lys Gly Ile Gly Gly Asn Glu Gln Val Asp Lys Leu Val Ser Ser
        1190                1195                1200

Gly Ile Arg Lys Val Leu Phe Leu Asp Gly Ile Asp Lys Ala Gln
        1205                1210                1215

Glu Glu His Glu Lys Tyr His Ser Asn Trp Arg Ala Met Ala Ser
        1220                1225                1230

Asp Phe Asn Leu Pro Pro Val Val Ala Lys Glu Ile Val Ala Ser
        1235                1240                1245

Cys Asp Gln Cys Gln Leu Lys Gly Glu Ala Met His Gly Gln Val
        1250                1255                1260

Asp Cys Ser Pro Gly Ile Trp Gln Leu Ala Cys Thr His Leu Glu
        1265                1270                1275

Gly Lys Ile Ile Leu Val Ala Val His Val Ala Ser Gly Tyr Ile
        1280                1285                1290

Glu Ala Glu Val Ile Pro Ala Glu Thr Gly Gln Glu Thr Ala Tyr
        1295                1300                1305

Phe Ile Leu Lys Leu Ala Gly Arg Trp Pro Val Lys Val Ile His
        1310                1315                1320

Thr Asp Asn Gly Ser Asn Phe Thr Ser Ala Ala Val Lys Ala Ala
        1325                1330                1335

Cys Trp Trp Ala Gly Ile Gln Gln Glu Phe Gly Ile Pro Tyr Asn
        1340                1345                1350

Pro Gln Ser Gln Gly Val Val Glu Ser Met Asn Lys Glu Leu Lys
        1355                1360                1365

Lys Ile Ile Gly Gln Val Arg Asp Gln Ala Glu His Leu Lys Thr
        1370                1375                1380

Ala Val Gln Met Ala Val Phe Ile His Asn Phe Lys Arg Lys Gly
        1385                1390                1395

Gly Ile Gly Gly Tyr Ser Ala Gly Glu Arg Ile Ile Asp Ile Ile
        1400                1405                1410

Ala Thr Asp Ile Gln Thr Lys Glu Leu Gln Lys Gln Ile Ile Lys
        1415                1420                1425

Ile Gln Asn Phe Arg Val Tyr Tyr Arg Asp Ser Arg Asp Pro Ile
        1430                1435                1440

Trp Lys Gly Pro Ala Lys Leu Leu Trp Lys Gly Glu Gly Ala Val
        1445                1450                1455

Val Ile Gln Asp Asn Ser Asp Ile Lys Val Val Pro Arg Arg Lys
        1460                1465                1470

Val Lys Ile Ile Lys Asp Tyr Gly Lys Gln Met Ala Gly Ala Asp
        1475                1480                1485

Cys Val Ala Gly Arg Gln Asp Glu Asp
        1490                1495

<210> SEQ ID NO 28
```

<211> LENGTH: 1492
<212> TYPE: PRT
<213> ORGANISM: Artificial Sequence
<220> FEATURE:
<223> OTHER INFORMATION: Synthetic Construct (Mosaic gagpol2 v4)

<400> SEQUENCE: 28

```
Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
    370                 375                 380
```

```
Val Lys Cys Phe Asn Cys Gly Lys Glu Gly His Ile Ala Arg Asn Cys
385                 390                 395                 400

Arg Ala Pro Arg Lys Gly Cys Trp Lys Cys Gly Lys Glu Gly His
            405                 410                 415

Gln Met Lys Asp Cys Thr Glu Arg Gln Ala Asn Phe Leu Gly Lys Ile
        420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Arg Glu Asn Leu Ala
                485                 490                 495

Phe Pro Gln Gly Lys Ala Arg Glu Phe Ser Ser Glu Gln Thr Arg Ala
            500                 505                 510

Asn Ser Pro Thr Arg Arg Glu Leu Gln Val Trp Gly Arg Asp Asn Asn
        515                 520                 525

Ser Leu Ser Glu Ala Gly Ala Asp Arg Gln Gly Thr Val Ser Phe Ser
530                 535                 540

Phe Pro Gln Ile Thr Leu Trp Gln Arg Pro Leu Val Thr Ile Lys Ile
545                 550                 555                 560

Gly Gly Gln Leu Lys Glu Ala Leu Leu Ala Thr Gly Ala Asp Asp Thr
                565                 570                 575

Val Leu Glu Glu Met Asn Leu Pro Gly Arg Trp Lys Pro Lys Met Ile
            580                 585                 590

Gly Gly Ile Gly Gly Phe Ile Lys Val Gly Gln Tyr Asp Gln Ile Pro
        595                 600                 605

Ile Glu Ile Cys Gly His Lys Ala Ile Gly Thr Val Leu Val Gly Pro
    610                 615                 620

Thr Pro Val Asn Ile Ile Gly Arg Asn Leu Leu Thr Gln Ile Gly Cys
625                 630                 635                 640

Thr Leu Asn Phe Pro Ile Ser Pro Ile Glu Thr Val Pro Val Lys Leu
                645                 650                 655

Lys Pro Gly Met Asp Gly Pro Lys Val Lys Gln Trp Pro Leu Thr Glu
            660                 665                 670

Glu Lys Ile Lys Ala Leu Val Glu Ile Cys Thr Glu Met Glu Lys Glu
        675                 680                 685

Gly Lys Ile Ser Lys Ile Gly Pro Glu Asn Pro Tyr Asn Thr Pro Ile
        690                 695                 700

Phe Ala Ile Lys Lys Lys Asp Ser Thr Lys Trp Arg Lys Leu Val Asp
705                 710                 715                 720

Phe Arg Glu Leu Asn Lys Arg Thr Gln Asp Phe Trp Glu Val Gln Leu
            725                 730                 735

Gly Ile Pro His Pro Ala Gly Leu Lys Lys Lys Ser Val Thr Val
                740                 745                 750

Leu Asp Val Gly Asp Ala Tyr Phe Ser Val Pro Leu Asp Glu Asp Phe
            755                 760                 765

Arg Lys Tyr Thr Ala Phe Thr Ile Pro Ser Ile Asn Asn Glu Thr Pro
    770                 775                 780

Gly Ile Arg Tyr Gln Tyr Asn Val Leu Pro Gln Gly Trp Lys Gly Ser
785                 790                 795                 800
```

```
Pro Ala Ile Phe Gln Ser Ser Met Thr Lys Ile Leu Glu Pro Phe Arg
                805                 810                 815

Lys Gln Asn Pro Asp Ile Val Ile Tyr Gln Tyr Met Asp His Leu Tyr
            820                 825                 830

Val Gly Ser Asp Leu Glu Ile Gly Gln His Arg Thr Lys Ile Glu Glu
        835                 840                 845

Leu Arg Gln His Leu Leu Arg Trp Gly Phe Thr Thr Pro Asp Lys Lys
    850                 855                 860

His Gln Lys Glu Pro Pro Phe Leu Trp Met Gly Tyr Glu Leu His Pro
865                 870                 875                 880

Asp Lys Trp Thr Val Gln Pro Ile Val Leu Pro Glu Lys Asp Ser Trp
                885                 890                 895

Thr Val Asn Asp Ile Gln Lys Leu Val Gly Lys Leu Asn Trp Ala Ser
            900                 905                 910

Gln Ile Tyr Ala Gly Ile Lys Val Lys Gln Leu Cys Lys Leu Leu Arg
        915                 920                 925

Gly Thr Lys Ala Leu Thr Glu Val Val Pro Leu Thr Glu Glu Ala Glu
    930                 935                 940

Leu Glu Leu Ala Glu Asn Arg Glu Ile Leu Lys Glu Pro Val His Gly
945                 950                 955                 960

Val Tyr Tyr Asp Pro Ser Lys Asp Leu Ile Ala Glu Ile Gln Lys Gln
                965                 970                 975

Gly Gln Gly Gln Trp Thr Tyr Gln Ile Tyr Gln Glu Pro Phe Lys Asn
            980                 985                 990

Leu Lys Thr Gly Lys Tyr Ala Arg Met Arg Gly Ala His Thr Asn Asp
        995                 1000                1005

Val Lys Gln Leu Thr Glu Ala Val Gln Lys Ile Ala Thr Glu Ser
    1010                1015                1020

Ile Val Ile Trp Gly Lys Thr Pro Lys Phe Lys Leu Pro Ile Gln
    1025                1030                1035

Lys Glu Thr Trp Glu Ala Trp Trp Thr Glu Tyr Trp Gln Ala Thr
    1040                1045                1050

Trp Ile Pro Glu Trp Glu Phe Val Asn Thr Pro Pro Leu Val Lys
    1055                1060                1065

Leu Trp Tyr Gln Leu Glu Lys Glu Pro Ile Val Gly Ala Glu Thr
    1070                1075                1080

Phe Tyr Val Asp Gly Ala Ala Asn Arg Glu Thr Lys Leu Gly Lys
    1085                1090                1095

Ala Gly Tyr Val Thr Asp Arg Gly Arg Gln Lys Val Val Ser Leu
    1100                1105                1110

Thr Asp Thr Thr Asn Gln Lys Thr Glu Leu Gln Ala Ile His Leu
    1115                1120                1125

Ala Leu Gln Asp Ser Gly Leu Glu Val Asn Ile Val Thr Asp Ser
    1130                1135                1140

Gln Tyr Ala Leu Gly Ile Ile Gln Ala Gln Pro Asp Lys Ser Glu
    1145                1150                1155

Ser Glu Leu Val Ser Gln Ile Ile Glu Gln Leu Ile Lys Lys Glu
    1160                1165                1170

Lys Val Tyr Leu Ala Trp Val Pro Ala His Lys Gly Ile Gly Gly
    1175                1180                1185

Asn Glu Gln Val Asp Lys Leu Val Ser Arg Gly Ile Arg Lys Val
    1190                1195                1200

Leu Phe Leu Asp Gly Ile Asp Lys Ala Gln Glu Glu His Glu Lys
```

-continued

```
                1205                1210                1215

Tyr His Ser Asn Trp Arg Ala Met Ala Ser Glu Phe Asn Leu Pro
        1220                1225                1230

Pro Ile Val Ala Lys Glu Ile Val Ala Ser Cys Asp Lys Cys Gln
    1235                1240                1245

Leu Lys Gly Glu Ala Ile His Gly Gln Val Asp Cys Ser Pro Gly
    1250                1255                1260

Ile Trp Gln Leu Ala Cys Thr His Leu Glu Gly Lys Val Ile Leu
    1265                1270                1275

Val Ala Val His Val Ala Ser Gly Tyr Ile Glu Ala Glu Val Ile
    1280                1285                1290

Pro Ala Glu Thr Gly Gln Glu Thr Ala Tyr Phe Leu Leu Lys Leu
    1295                1300                1305

Ala Gly Arg Trp Pro Val Lys Thr Ile His Thr Asp Asn Gly Ser
    1310                1315                1320

Asn Phe Thr Ser Ala Thr Val Lys Ala Ala Cys Trp Trp Ala Gly
    1325                1330                1335

Ile Lys Gln Glu Phe Gly Ile Pro Tyr Asn Pro Gln Ser Gln Gly
    1340                1345                1350

Val Val Glu Ser Ile Asn Lys Glu Leu Lys Lys Ile Ile Gly Gln
    1355                1360                1365

Val Arg Asp Gln Ala Glu His Leu Lys Thr Ala Val Gln Met Ala
    1370                1375                1380

Val Phe Ile His Asn Phe Lys Arg Lys Gly Gly Ile Gly Glu Tyr
    1385                1390                1395

Ser Ala Gly Glu Arg Ile Val Asp Ile Ile Ala Ser Asp Ile Gln
    1400                1405                1410

Thr Lys Glu Leu Gln Lys Gln Ile Thr Lys Ile Gln Asn Phe Arg
    1415                1420                1425

Val Tyr Tyr Arg Asp Ser Arg Asp Pro Leu Trp Lys Gly Pro Ala
    1430                1435                1440

Lys Leu Leu Trp Lys Gly Glu Gly Ala Val Val Ile Gln Asp Asn
    1445                1450                1455

Ser Asp Ile Lys Val Val Pro Arg Arg Lys Ala Lys Ile Ile Arg
    1460                1465                1470

Asp Tyr Gly Lys Gln Met Ala Gly Asp Asp Cys Val Ala Ser Arg
    1475                1480                1485

Gln Asp Glu Asp
    1490

<210> SEQ ID NO 29
<211> LENGTH: 1350
<212> TYPE: PRT
<213> ORGANISM: Artificial Sequence
<220> FEATURE:
<223> OTHER INFORMATION: Synthetic Construct (Mosaic gagpoll v5)

<400> SEQUENCE: 29

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
```

```
            50                  55                  60
Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Glu Lys Ile Glu Glu Gln Asn Lys Ser Lys
                100                 105                 110

Lys Lys Ala Gln Gln Ala Ala Ala Asp Thr Gly Asn Ser Ser Gln Val
                115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
                195                 200                 205

Ala Ala Glu Trp Asp Arg Val His Pro Val His Ala Gly Pro Ile Ala
        210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Val Ser Ile Leu Asp Ile Arg Gln Gly
                275                 280                 285

Pro Lys Glu Pro Phe Arg Asp Tyr Val Asp Arg Phe Tyr Lys Thr Leu
        290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Ser Ala Thr Ile Met Met Gln Arg Gly Asn Phe Arg
        370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Asn Lys Gly Arg Pro Gly Asn Phe
                435                 440                 445

Leu Gln Asn Arg Pro Glu Pro Thr Ala Pro Glu Glu Ser Phe Arg
        450                 455                 460

Phe Gly Glu Glu Thr Thr Thr Pro Ser Gln Lys Gln Glu Pro Ile Asp
465                 470                 475                 480
```

```
Lys Glu Met Tyr Pro Leu Ala Ser Leu Lys Ser Leu Phe Gly Asn Asp
            485                 490                 495
Pro Ser Ser Gln Met Ala Pro Ile Ser Pro Ile Glu Thr Val Pro Val
        500                 505                 510
Lys Leu Lys Pro Gly Met Asp Gly Pro Arg Val Lys Gln Trp Pro Leu
    515                 520                 525
Thr Glu Glu Lys Ile Lys Ala Leu Thr Ala Ile Cys Glu Glu Met Glu
530                 535                 540
Lys Glu Gly Lys Ile Thr Lys Ile Gly Pro Glu Asn Pro Tyr Asn Thr
545                 550                 555                 560
Pro Val Phe Ala Ile Lys Lys Lys Asp Ser Thr Lys Trp Arg Lys Leu
                565                 570                 575
Val Asp Phe Arg Glu Leu Asn Lys Arg Thr Gln Asp Phe Trp Glu Val
            580                 585                 590
Gln Leu Gly Ile Pro His Pro Ala Gly Leu Lys Lys Lys Lys Ser Val
        595                 600                 605
Thr Val Leu Asp Val Gly Asp Ala Tyr Phe Ser Val Pro Leu Asp Glu
    610                 615                 620
Gly Phe Arg Lys Tyr Thr Ala Phe Thr Ile Pro Ser Thr Asn Asn Glu
625                 630                 635                 640
Thr Pro Gly Ile Arg Tyr Gln Tyr Asn Val Leu Pro Gln Gly Trp Lys
                645                 650                 655
Gly Ser Pro Ala Ile Phe Gln Cys Ser Met Thr Arg Ile Leu Glu Pro
            660                 665                 670
Phe Arg Ala Lys Asn Pro Glu Ile Val Ile Tyr Gln Tyr Met Asp His
        675                 680                 685
Leu Tyr Val Gly Ser Asp Leu Glu Ile Gly Gln His Arg Ala Lys Ile
    690                 695                 700
Glu Glu Leu Arg Glu His Leu Leu Lys Trp Gly Phe Thr Thr Pro Asp
705                 710                 715                 720
Lys Lys His Gln Lys Glu Pro Pro Phe Leu Trp Met Gly Tyr Glu Leu
                725                 730                 735
His Pro Asp Lys Trp Thr Val Gln Pro Ile Gln Leu Pro Glu Lys Asp
            740                 745                 750
Ser Trp Thr Val Asn Asp Ile Gln Lys Leu Val Gly Lys Leu Asn Trp
        755                 760                 765
Ala Ser Gln Ile Tyr Pro Gly Ile Lys Val Arg Gln Leu Cys Lys Leu
    770                 775                 780
Leu Arg Gly Ala Lys Ala Leu Thr Asp Ile Val Pro Leu Thr Glu Glu
785                 790                 795                 800
Ala Glu Leu Glu Leu Ala Glu Asn Arg Glu Ile Leu Lys Glu Pro Val
                805                 810                 815
His Gly Val Tyr Tyr Asp Pro Ser Lys Asp Leu Ile Ala Glu Ile Gln
            820                 825                 830
Lys Gln Gly His Asp Gln Trp Thr Tyr Gln Ile Tyr Gln Glu Pro Phe
        835                 840                 845
Lys Asn Leu Lys Thr Gly Lys Tyr Ala Lys Met Arg Thr Ala His Thr
    850                 855                 860
Asn Asp Val Lys Gln Leu Thr Glu Ala Val Gln Lys Ile Ala Met Glu
865                 870                 875                 880
Ser Ile Val Ile Trp Gly Lys Thr Pro Lys Phe Arg Leu Pro Ile Gln
                885                 890                 895
```

-continued

Lys Glu Thr Trp Glu Thr Trp Trp Thr Asp Tyr Trp Gln Ala Thr Trp
              900                 905                 910

Ile Pro Glu Trp Glu Phe Val Asn Thr Pro Pro Leu Val Lys Leu Trp
              915                 920                 925

Tyr Gln Leu Glu Lys Asp Pro Ile Ala Gly Val Glu Thr Phe Tyr Val
              930                 935                 940

Asp Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
              965                 970                 975

Gln Lys Thr Glu Leu Gln Ala Ile Tyr Leu Ala Leu Gln Asp Ser Gly
              980                 985                 990

Ser Glu Val Asn Ile Val Thr Asp Ser Gln Tyr Ala Leu Gly Ile Ile
              995                 1000                1005

Gln Ala Gln Pro Asp Lys Ser Glu Ser Glu Leu Val Asn Gln Ile
      1010                1015                1020

Ile Glu Gln Leu Ile Lys Lys Glu Arg Val Tyr Leu Ser Trp Val
      1025                1030                1035

Pro Ala His Lys Gly Ile Gly Gly Asn Glu Gln Val Asp Lys Leu
      1040                1045                1050

Val Ser Ser Gly Ile Arg Lys Val Leu Phe Leu Asp Gly Ile Asp
      1055                1060                1065

Lys Ala Gln Glu Glu His Glu Lys Tyr His Ser Asn Trp Arg Ala
      1070                1075                1080

Met Ala Ser Asp Phe Asn Leu Pro Pro Val Val Ala Lys Glu Ile
      1085                1090                1095

Val Ala Ser Cys Asp Gln Cys Gln Leu Lys Gly Glu Ala Met His
      1100                1105                1110

Gly Gln Val Asp Cys Ser Pro Gly Ile Trp Gln Leu Ala Cys Thr
      1115                1120                1125

His Leu Glu Gly Lys Ile Ile Leu Val Ala Val His Val Ala Ser
      1130                1135                1140

Gly Tyr Ile Glu Ala Glu Val Ile Pro Ala Glu Thr Gly Gln Glu
      1145                1150                1155

Thr Ala Tyr Phe Ile Leu Lys Leu Ala Gly Arg Trp Pro Val Lys
      1160                1165                1170

Val Ile His Thr Asp Asn Gly Ser Asn Phe Thr Ser Ala Ala Val
      1175                1180                1185

Lys Ala Ala Cys Trp Trp Ala Gly Ile Gln Gln Glu Phe Gly Ile
      1190                1195                1200

Pro Tyr Asn Pro Gln Ser Gln Gly Val Val Glu Ser Met Asn Lys
      1205                1210                1215

Glu Leu Lys Lys Ile Ile Gly Gln Val Arg Asp Gln Ala Glu His
      1220                1225                1230

Leu Lys Thr Ala Val Gln Met Ala Val Phe Ile His Asn Phe Lys
      1235                1240                1245

Arg Lys Gly Gly Ile Gly Gly Tyr Ser Ala Gly Glu Arg Ile Ile
      1250                1255                1260

Asp Ile Ile Ala Thr Asp Ile Gln Thr Lys Glu Leu Gln Lys Gln
      1265                1270                1275

Ile Ile Lys Ile Gln Asn Phe Arg Val Tyr Tyr Arg Asp Ser Arg
      1280                1285                1290

Asp Pro Ile Trp Lys Gly Pro Ala Lys Leu Leu Trp Lys Gly Glu

```
          1295                1300                1305

Gly Ala Val Val Ile Gln Asp Asn Ser Asp Ile Lys Val Val Pro
         1310                1315                1320

Arg Arg Lys Val Lys Ile Ile Lys Asp Tyr Gly Lys Gln Met Ala
        1325                1330                1335

Gly Ala Asp Cys Val Ala Gly Arg Gln Asp Glu Asp
        1340                1345                1350

<210> SEQ ID NO 30
<211> LENGTH: 1341
<212> TYPE: PRT
<213> ORGANISM: Artificial Sequence
<220> FEATURE:
<223> OTHER INFORMATION: Synthetic Construct (Mosaic gagpol2 v5)

<400> SEQUENCE: 30

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
```

```
            305                 310                 315                 320
        Gln Asn Ala Asn Pro Asp Cys Lys Thr Ile Leu Arg Ala Leu Gly Pro
                        325                 330                 335
        Gly Ala Thr Leu Glu Glu Met Met Thr Ala Cys Gln Gly Val Gly Gly
                        340                 345                 350
        Pro Ser His Lys Ala Arg Val Leu Ala Glu Ala Met Ser Gln Thr Asn
                        355                 360                 365
        Ser Thr Ile Leu Met Gln Arg Ser Asn Phe Lys Gly Ser Lys Arg Ile
                        370                 375                 380
        Val Lys Cys Phe Asn Cys Gly Lys Glu Gly His Ile Ala Arg Asn Cys
        385                 390                 395                 400
        Arg Ala Pro Arg Lys Lys Gly Cys Trp Lys Cys Gly Lys Glu Gly His
                        405                 410                 415
        Gln Met Lys Asp Cys Thr Glu Arg Gln Ala Asn Phe Leu Gly Lys Ile
                        420                 425                 430
        Trp Pro Ser His Lys Gly Arg Pro Gly Asn Phe Leu Gln Ser Arg Pro
                        435                 440                 445
        Glu Pro Thr Ala Pro Pro Ala Glu Ser Phe Arg Phe Glu Glu Thr Thr
                        450                 455                 460
        Pro Ala Pro Lys Gln Glu Pro Lys Asp Arg Glu Pro Leu Thr Ser Leu
        465                 470                 475                 480
        Arg Ser Leu Phe Gly Ser Asp Pro Leu Ser Gln Met Ala Pro Ile Ser
                        485                 490                 495
        Pro Ile Glu Thr Val Pro Val Lys Leu Lys Pro Gly Met Asp Gly Pro
                        500                 505                 510
        Lys Val Lys Gln Trp Pro Leu Thr Glu Glu Lys Ile Lys Ala Leu Val
                        515                 520                 525
        Glu Ile Cys Thr Glu Met Glu Lys Glu Gly Lys Ile Ser Lys Ile Gly
                        530                 535                 540
        Pro Glu Asn Pro Tyr Asn Thr Pro Ile Phe Ala Ile Lys Lys Lys Asp
        545                 550                 555                 560
        Ser Thr Lys Trp Arg Lys Leu Val Asp Phe Arg Glu Leu Asn Lys Arg
                        565                 570                 575
        Thr Gln Asp Phe Trp Glu Val Gln Leu Gly Ile Pro His Pro Ala Gly
                        580                 585                 590
        Leu Lys Lys Lys Lys Ser Val Thr Val Leu Asp Val Gly Asp Ala Tyr
                        595                 600                 605
        Phe Ser Val Pro Leu Asp Glu Asp Phe Arg Lys Tyr Thr Ala Phe Thr
                        610                 615                 620
        Ile Pro Ser Ile Asn Asn Glu Thr Pro Gly Ile Arg Tyr Gln Tyr Asn
        625                 630                 635                 640
        Val Leu Pro Gln Gly Trp Lys Gly Ser Pro Ala Ile Phe Gln Ser Ser
                        645                 650                 655
        Met Thr Lys Ile Leu Glu Pro Phe Arg Lys Gln Asn Pro Asp Ile Val
                        660                 665                 670
        Ile Tyr Gln Tyr Met Asp His Leu Tyr Val Gly Ser Asp Leu Glu Ile
                        675                 680                 685
        Gly Gln His Arg Thr Lys Ile Glu Glu Leu Arg Gln His Leu Leu Arg
                        690                 695                 700
        Trp Gly Phe Thr Thr Pro Asp Lys Lys His Gln Lys Glu Pro Pro Phe
        705                 710                 715                 720
        Leu Trp Met Gly Tyr Glu Leu His Pro Asp Lys Trp Thr Val Gln Pro
                        725                 730                 735
```

```
Ile Val Leu Pro Glu Lys Asp Ser Trp Thr Val Asn Asp Ile Gln Lys
            740                 745                 750

Leu Val Gly Lys Leu Asn Trp Ala Ser Gln Ile Tyr Ala Gly Ile Lys
            755                 760                 765

Val Lys Gln Leu Cys Lys Leu Leu Arg Gly Thr Lys Ala Leu Thr Glu
            770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
            805                 810                 815

Asp Leu Ile Ala Glu Ile Gln Lys Gln Gly Gln Gly Gln Trp Thr Tyr
            820                 825                 830

Gln Ile Tyr Gln Glu Pro Phe Lys Asn Leu Lys Thr Gly Lys Tyr Ala
            835                 840                 845

Arg Met Arg Gly Ala His Thr Asn Asp Val Lys Gln Leu Thr Glu Ala
850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
            885                 890                 895

Glu Tyr Trp Gln Ala Thr Trp Ile Pro Glu Trp Glu Phe Val Asn Thr
            900                 905                 910

Pro Pro Leu Val Lys Leu Trp Tyr Gln Leu Glu Lys Glu Pro Ile Val
            915                 920                 925

Gly Ala Glu Thr Phe Tyr Val Asp Gly Ala Ala Asn Arg Glu Thr Lys
            930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Glu Leu Gln Ala Ile His
            965                 970                 975

Leu Ala Leu Gln Asp Ser Gly Leu Glu Val Asn Ile Val Thr Asp Ser
            980                 985                 990

Gln Tyr Ala Leu Gly Ile Ile Gln Ala Gln Pro Asp Lys Ser Glu Ser
            995                 1000                1005

Glu Leu Val Ser Gln Ile Ile Glu Gln Leu Ile Lys Lys Glu Lys
            1010                1015                1020

Val Tyr Leu Ala Trp Val Pro Ala His Lys Gly Ile Gly Gly Asn
            1025                1030                1035

Glu Gln Val Asp Lys Leu Val Ser Arg Gly Ile Arg Lys Val Leu
            1040                1045                1050

Phe Leu Asp Gly Ile Asp Lys Ala Gln Glu Glu His Glu Lys Tyr
            1055                1060                1065

His Ser Asn Trp Arg Ala Met Ala Ser Glu Phe Asn Leu Pro Pro
            1070                1075                1080

Ile Val Ala Lys Glu Ile Val Ala Ser Cys Asp Lys Cys Gln Leu
            1085                1090                1095

Lys Gly Glu Ala Ile His Gly Gln Val Asp Cys Ser Pro Gly Ile
            1100                1105                1110

Trp Gln Leu Ala Cys Thr His Leu Glu Gly Lys Val Ile Leu Val
            1115                1120                1125

Ala Val His Val Ala Ser Gly Tyr Ile Glu Ala Glu Val Ile Pro
            1130                1135                1140
```

Ala Glu Thr Gly Gln Glu Thr Ala Tyr Phe Leu Leu Lys Leu Ala
1145                1150                1155

Gly Arg Trp Pro Val Lys Thr Ile His Thr Asp Asn Gly Ser Asn
1160                1165                1170

Phe Thr Ser Ala Thr Val Lys Ala Ala Cys Trp Trp Ala Gly Ile
1175                1180                1185

Lys Gln Glu Phe Gly Ile Pro Tyr Asn Pro Gln Ser Gln Gly Val
1190                1195                1200

Val Glu Ser Ile Asn Lys Glu Leu Lys Lys Ile Ile Gly Gln Val
1205                1210                1215

Arg Asp Gln Ala Glu His Leu Lys Thr Ala Val Gln Met Ala Val
1220                1225                1230

Phe Ile His Asn Phe Lys Arg Lys Gly Gly Ile Gly Glu Tyr Ser
1235                1240                1245

Ala Gly Glu Arg Ile Val Asp Ile Ile Ala Ser Asp Ile Gln Thr
1250                1255                1260

Lys Glu Leu Gln Lys Gln Ile Thr Lys Ile Gln Asn Phe Arg Val
1265                1270                1275

Tyr Tyr Arg Asp Ser Arg Asp Pro Leu Trp Lys Gly Pro Ala Lys
1280                1285                1290

Leu Leu Trp Lys Gly Glu Gly Ala Val Val Ile Gln Asp Asn Ser
1295                1300                1305

Asp Ile Lys Val Val Pro Arg Arg Lys Ala Lys Ile Ile Arg Asp
1310                1315                1320

Tyr Gly Lys Gln Met Ala Gly Asp Asp Cys Val Ala Ser Arg Gln
1325                1330                1335

Asp Glu Asp
1340

<210> SEQ ID NO 31
<211> LENGTH: 1556
<212> TYPE: PRT
<213> ORGANISM: Artificial Sequence
<220> FEATURE:
<223> OTHER INFORMATION: Synthetic Construct (Mosaic gagpolnef1)

<400> SEQUENCE: 31

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Ile Gln Gly Gln Met Val His
    130                 135                 140

-continued

```
Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
                195                 200                 205

Ala Ala Glu Trp Asp Arg Val His Pro Val His Ala Gly Pro Ile Ala
        210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Val Ser Ile Leu Asp Ile Arg Gln Gly
                275                 280                 285

Pro Lys Glu Pro Phe Arg Asp Tyr Val Asp Arg Phe Tyr Lys Thr Leu
        290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Ser Ala Thr Ile Met Met Gln Arg Gly Asn Phe Arg
                370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Asn Lys Gly Arg Pro Gly Asn Phe
                435                 440                 445

Leu Gln Asn Arg Pro Glu Pro Thr Ala Pro Pro Glu Glu Ser Phe Arg
        450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
                500                 505                 510

Lys Leu Lys Pro Gly Met Asp Gly Pro Arg Val Lys Gln Trp Pro Leu
                515                 520                 525

Thr Glu Glu Lys Ile Lys Ala Leu Thr Ala Ile Cys Glu Glu Met Glu
                530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
```

```
                    565                 570                 575
        Val Asp Phe Arg Glu Leu Asn Lys Arg Thr Gln Asp Phe Trp Glu Val
                        580                 585                 590

Gln Leu Gly Ile Pro His Pro Ala Gly Leu Lys Lys Lys Lys Ser Val
                        595                 600                 605

Thr Val Leu Ala Val Gly Asp Ala Tyr Phe Ser Val Pro Leu Asp Glu
                        610                 615                 620

Gly Phe Arg Lys Tyr Thr Ala Phe Thr Ile Pro Ser Thr Asn Asn Glu
        625                 630                 635                 640

Thr Pro Gly Ile Arg Tyr Gln Tyr Asn Val Leu Pro Gln Gly Trp Lys
                        645                 650                 655

Gly Ser Pro Ala Ile Phe Gln Cys Ser Met Thr Arg Ile Leu Glu Pro
                        660                 665                 670

Phe Arg Ala Lys Asn Pro Glu Ile Val Ile Tyr Gln Tyr Met Ala Ala
                        675                 680                 685

Leu Tyr Val Gly Ser Asp Leu Glu Ile Gly Gln His Arg Ala Lys Ile
                        690                 695                 700

Glu Glu Leu Arg Glu His Leu Leu Lys Trp Gly Phe Thr Thr Pro Asp
        705                 710                 715                 720

Lys Lys His Gln Lys Glu Pro Pro Phe Leu Trp Met Gly Tyr Glu Leu
                        725                 730                 735

His Pro Asp Lys Trp Thr Val Gln Pro Ile Gln Leu Pro Glu Lys Asp
                        740                 745                 750

Ser Trp Thr Val Asn Asp Ile Gln Lys Leu Val Gly Lys Leu Asn Trp
                        755                 760                 765

Ala Ser Gln Ile Tyr Pro Gly Ile Lys Val Arg Gln Leu Cys Lys Leu
                        770                 775                 780

Leu Arg Gly Ala Lys Ala Leu Thr Asp Ile Val Pro Leu Thr Glu Glu
        785                 790                 795                 800

Ala Glu Leu Glu Leu Ala Glu Asn Arg Glu Ile Leu Lys Glu Pro Val
                        805                 810                 815

His Gly Val Tyr Tyr Asp Pro Ser Lys Asp Leu Ile Ala Glu Ile Gln
                        820                 825                 830

Lys Gln Gly His Asp Gln Trp Thr Tyr Gln Ile Tyr Gln Glu Pro Phe
                        835                 840                 845

Lys Asn Leu Lys Thr Gly Lys Tyr Ala Lys Met Arg Thr Ala His Thr
                        850                 855                 860

Asn Asp Val Lys Gln Leu Thr Glu Ala Val Gln Lys Ile Ala Met Glu
        865                 870                 875                 880

Ser Ile Val Ile Trp Gly Lys Thr Pro Lys Phe Arg Leu Pro Ile Gln
                        885                 890                 895

Lys Glu Thr Trp Glu Thr Trp Trp Thr Asp Tyr Trp Gln Ala Thr Trp
                        900                 905                 910

Ile Pro Glu Trp Glu Phe Val Asn Thr Pro Pro Leu Val Lys Leu Trp
                        915                 920                 925

Tyr Gln Leu Glu Lys Asp Pro Ile Ala Gly Val Glu Thr Phe Tyr Val
                        930                 935                 940

Ala Gly Ala Ala Asn Arg Glu Thr Lys Leu Gly Lys Ala Gly Tyr Val
        945                 950                 955                 960

Thr Asp Arg Gly Arg Gln Lys Ile Val Ser Leu Thr Glu Thr Thr Asn
                        965                 970                 975

Gln Lys Thr Ala Leu Gln Ala Ile Tyr Leu Ala Leu Gln Asp Ser Gly
                        980                 985                 990
```

```
Ser Glu Val Asn Ile Val Thr Ala  Ser Gln Tyr Ala Leu  Gly Ile Ile
         995                 1000                1005

Gln Ala  Gln Pro Asp Lys Ser  Glu Ser Glu Leu Val  Asn Gln Ile
    1010                 1015               1020

Ile Glu  Gln Leu Ile Lys Lys  Glu Arg Val Tyr Leu  Ser Trp Val
    1025                 1030                1035

Pro Ala  His Lys Gly Ile Gly  Gly Asn Glu Gln Val  Asp Lys Leu
    1040                 1045                1050

Val Ser  Ser Gly Ile Arg Lys  Val Leu Phe Leu Asp  Gly Ile Asp
    1055                 1060                1065

Lys Ala  Gln Glu Glu His Glu  Lys Tyr His Ser Asn  Trp Arg Ala
    1070                 1075                1080

Met Ala  Ser Asp Phe Asn Leu  Pro Pro Val Val Ala  Lys Glu Ile
    1085                 1090                1095

Val Ala  Ser Cys Asp Gln Cys  Gln Leu Lys Gly Glu  Ala Met His
    1100                 1105                1110

Gly Gln  Val Asp Cys Ser Pro  Gly Ile Trp Gln Leu  Ala Cys Thr
    1115                 1120                1125

His Leu  Glu Gly Lys Ile Ile  Leu Val Ala Val His  Val Ala Ser
    1130                 1135                1140

Gly Tyr  Ile Glu Ala Glu Val  Ile Pro Ala Glu Thr  Gly Gln Glu
    1145                 1150                1155

Thr Ala  Tyr Phe Ile Leu Lys  Leu Ala Gly Arg Trp  Pro Val Lys
    1160                 1165                1170

Val Ile  His Thr Ala Asn Gly  Ser Asn Phe Thr Ser  Ala Ala Val
    1175                 1180                1185

Lys Ala  Ala Cys Trp Trp Ala  Gly Ile Gln Gln Glu  Phe Gly Ile
    1190                 1195                1200

Pro Tyr  Asn Pro Gln Ser Gln  Gly Val Val Ala Ser  Met Asn Lys
    1205                 1210                1215

Glu Leu  Lys Lys Ile Ile Gly  Gln Val Arg Asp Gln  Ala Glu His
    1220                 1225                1230

Leu Lys  Thr Ala Val Gln Met  Ala Val Phe Ile His  Asn Phe Lys
    1235                 1240                1245

Arg Lys  Gly Gly Ile Gly Gly  Tyr Ser Ala Gly Glu  Arg Ile Ile
    1250                 1255                1260

Asp Ile  Ile Ala Thr Asp Ile  Gln Thr Lys Glu Leu  Gln Lys Gln
    1265                 1270                1275

Ile Ile  Lys Ile Gln Asn Phe  Arg Val Tyr Tyr Arg  Asp Ser Arg
    1280                 1285                1290

Asp Pro  Ile Trp Lys Gly Pro  Ala Lys Leu Leu Trp  Lys Gly Glu
    1295                 1300                1305

Gly Ala  Val Val Ile Gln Asp  Asn Ser Asp Ile Lys  Val Val Pro
    1310                 1315                1320

Arg Arg  Lys Val Lys Ile Ile  Lys Asp Tyr Gly Lys  Gln Met Ala
    1325                 1330                1335

Gly Ala  Asp Cys Val Ala Gly  Arg Gln Asp Glu Asp  Met Ala Gly
    1340                 1345                1350

Lys Trp  Ser Lys Ser Ser Val  Val Gly Trp Pro Ala  Ile Arg Glu
    1355                 1360                1365

Arg Met  Arg Arg Ala Glu Pro  Ala Ala Asp Gly Val  Gly Ala Val
    1370                 1375                1380
```

```
Ser Arg Asp Leu Glu Lys His Gly Ala Ile Thr Ser Ser Asn Thr
    1385                1390                1395

Ala Ala Asn Asn Ala Asp Cys Ala Trp Leu Glu Ala Gln Glu Glu
    1400                1405                1410

Glu Glu Val Gly Phe Pro Val Arg Pro Gln Val Pro Leu Arg Pro
    1415                1420                1425

Met Thr Tyr Lys Gly Ala Leu Asp Leu Ser His Phe Leu Lys Glu
    1430                1435                1440

Lys Gly Gly Leu Glu Gly Leu Ile Tyr Ser Gln Lys Arg Gln Asp
    1445                1450                1455

Ile Leu Asp Leu Trp Val Tyr His Thr Gln Gly Tyr Phe Pro Asp
    1460                1465                1470

Trp Gln Asn Tyr Thr Pro Gly Pro Gly Ile Arg Tyr Pro Leu Thr
    1475                1480                1485

Phe Gly Trp Cys Phe Lys Leu Val Pro Val Glu Pro Glu Lys Ile
    1490                1495                1500

Glu Glu Ala Asn Glu Gly Glu Asn Asn Ser Leu Leu His Pro Met
    1505                1510                1515

Ser Gln His Gly Met Asp Asp Pro Glu Lys Glu Val Leu Met Trp
    1520                1525                1530

Lys Phe Asp Ser Arg Leu Ala Phe His His Met Ala Arg Glu Leu
    1535                1540                1545

His Pro Glu Tyr Tyr Lys Asp Cys
    1550                1555

<210> SEQ ID NO 32
<211> LENGTH: 1547
<212> TYPE: PRT
<213> ORGANISM: Artificial Sequence
<220> FEATURE:
<223> OTHER INFORMATION: Synthetic Construct (Mosaic gagpolnef2)

<400> SEQUENCE: 32

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
                100                 105                 110

Gln Lys Thr Gln Gln Ala Lys Glu Ala Asp Gly Lys Val Ser Gln Asn
            115                 120                 125

Tyr Pro Ile Val Gln Asn Leu Gln Gly Gln Met Val His Gln Pro Ile
        130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175
```

```
Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
            210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
            500                 505                 510

Lys Val Lys Gln Trp Pro Leu Thr Glu Glu Lys Ile Lys Ala Leu Val
        515                 520                 525

Glu Ile Cys Thr Glu Met Glu Lys Glu Gly Lys Ile Ser Lys Ile Gly
    530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
            580                 585                 590

Leu Lys Lys Lys Lys Ser Val Thr Val Leu Ala Val Gly Asp Ala Tyr
```

```
                 595                 600                 605

Phe Ser Val Pro Leu Asp Glu Asp Phe Arg Lys Tyr Thr Ala Phe Thr
610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
                645                 650                 655

Met Thr Lys Ile Leu Glu Pro Phe Arg Lys Gln Asn Pro Asp Ile Val
                660                 665                 670

Ile Tyr Gln Tyr Met Ala Ala Leu Tyr Val Gly Ser Asp Leu Glu Ile
                675                 680                 685

Gly Gln His Arg Thr Lys Ile Glu Glu Leu Arg Gln His Leu Leu Arg
690                 695                 700

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
                725                 730                 735

Ile Val Leu Pro Glu Lys Asp Ser Trp Thr Val Asn Asp Ile Gln Lys
                740                 745                 750

Leu Val Gly Lys Leu Asn Trp Ala Ser Gln Ile Tyr Ala Gly Ile Lys
                755                 760                 765

Val Lys Gln Leu Cys Lys Leu Leu Arg Gly Thr Lys Ala Leu Thr Glu
770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
                805                 810                 815

Asp Leu Ile Ala Glu Ile Gln Lys Gln Gly Gln Gly Gln Trp Thr Tyr
                820                 825                 830

Gln Ile Tyr Gln Glu Pro Phe Lys Asn Leu Lys Thr Gly Lys Tyr Ala
                835                 840                 845

Arg Met Arg Gly Ala His Thr Asn Asp Val Lys Gln Leu Thr Glu Ala
850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
                900                 905                 910

Pro Pro Leu Val Lys Leu Trp Tyr Gln Leu Glu Lys Glu Pro Ile Val
                915                 920                 925

Gly Ala Glu Thr Phe Tyr Val Ala Gly Ala Ala Asn Arg Glu Thr Lys
                930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
                980                 985                 990

Gln Tyr Ala Leu Gly Ile Ile Gln  Ala Gln Pro Asp Lys  Ser Glu Ser
                995                 1000                1005

Glu Leu Val Ser Gln Ile Ile  Glu Gln Leu Ile Lys  Lys Glu Lys
1010                1015                1020
```

```
Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
    1190                1195                1200

Val Ala Ser Ile Asn Lys Glu Leu Lys Lys Ile Ile Gly Gln Val
    1205                1210                1215

Arg Asp Gln Ala Glu His Leu Lys Thr Ala Val Gln Met Ala Val
    1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
    1250                1255                1260

Lys Glu Leu Gln Lys Gln Ile Thr Lys Ile Gln Asn Phe Arg Val
    1265                1270                1275

Tyr Tyr Arg Asp Ser Arg Asp Pro Leu Trp Lys Gly Pro Ala Lys
    1280                1285                1290

Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
    1310                1315                1320

Tyr Gly Lys Gln Met Ala Gly Asp Asp Cys Val Ala Ser Arg Gln
    1325                1330                1335

Asp Glu Asp Met Ala Gly Lys Trp Ser Lys Ser Ser Ile Val Gly
    1340                1345                1350

Trp Pro Ala Val Arg Glu Arg Ile Arg Arg Ala Glu Pro Ala Ala
    1355                1360                1365

Glu Gly Val Gly Ala Ala Ser Gln Asp Leu Asp Lys Tyr Gly Ala
    1370                1375                1380

Leu Thr Ser Ser Asn Thr Ala Ala Thr Asn Ala Asp Cys Ala Trp
    1385                1390                1395

Leu Glu Ala Gln Glu Asp Glu Glu Val Gly Phe Pro Val Lys Pro
    1400                1405                1410
```

```
Gln Val Pro Leu Arg Pro Met Thr Tyr Lys Ala Ala Phe Asp Leu
    1415                1420                1425

Ser Phe Phe Leu Lys Glu Lys Gly Gly Leu Asp Gly Leu Ile Tyr
    1430                1435                1440

Ser Lys Lys Arg Gln Glu Ile Leu Asp Leu Trp Val Tyr Asn Thr
    1445                1450                1455

Gln Gly Phe Phe Pro Asp Trp Gln Asn Tyr Thr Pro Gly Pro Gly
    1460                1465                1470

Val Arg Tyr Pro Leu Thr Phe Gly Trp Cys Phe Lys Leu Val Pro
    1475                1480                1485

Val Asp Pro Arg Glu Val Glu Glu Ala Asn Lys Gly Glu Asn Asn
    1490                1495                1500

Cys Leu Leu His Pro Met Asn Leu His Gly Met Asp Asp Pro Glu
    1505                1510                1515

Arg Glu Val Leu Val Trp Arg Phe Asp Ser Arg Leu Ala Phe His
    1520                1525                1530

His Met Ala Arg Glu Lys His Pro Glu Tyr Tyr Lys Asn Cys
    1535                1540                1545

<210> SEQ ID NO 33
<211> LENGTH: 6
<212> TYPE: PRT
<213> ORGANISM: Artificial Sequence
<220> FEATURE:
<223> OTHER INFORMATION: Factor Xa cleavage site

<400> SEQUENCE: 33

Ser Arg Ile Glu Gly Arg
1               5

<210> SEQ ID NO 34
<211> LENGTH: 22
<212> TYPE: DNA
<213> ORGANISM: Artificial Sequence
<220> FEATURE:
<223> OTHER INFORMATION: Synthetic Construct (dinucleotide CpG DNA)

<400> SEQUENCE: 34
tcgtcgttgt cgttttgtcg tt                                          22
```

STABILIZED HUMAN IMMUNODEFICIENCY VIRUS (HIV) ENVELOPE (ENV) TRIMER VACCINES AND METHODS OF USING SAME

STATEMENT AS TO FEDERALLY FUNDED RESEARCH

This invention was made with government support under Grant Nos. AI096040 and AI084794, awarded by the National Institutes of Health (NIA/National Institute of Allergy and Infectious Diseases (NIAID). The government has certain rights in the invention.

BACKGROUND OF THE INVENTION

Vaccines that elicit cellular immune responses against viruses seek to reflect global viral diversity in order to effectively treat or prevent viral infection. For HIV vaccines, the initiation of robust and diverse human immunodeficiency virus (HIV)-specific T cell responses is desirable for an effective HIV vaccine. The highly variable Envelope protein (Env) is the primary target for neutralizing antibodies against HIV, and vaccine antigens may be tailored accordingly to elicit these antibody responses. To this end, immunogens mimicking the trimeric structure of Env on the native HIV virion are actively being pursued as antibody-based HIV vaccines. However, it has proven difficult to produce biochemically stable trimeric Env immunogens that elicit diverse neutralizing antibody responses.

Thus, there is an unmet need in the field for the development of vaccines that include novel, optimized trimeric Env immunogens, which can elicit broadly neutralizing antibody responses in order to allow for more successful HIV vaccination outcomes.

SUMMARY OF THE INVENTION

In a first aspect, the invention features a stabilized trimer having three gp140 polypeptides in which at least one (e.g., two or each) of the gp140 polypeptides includes an amino acid sequence having at least 90% identity (e.g., at least 91%, 92%, 93%, 94%, 95%, 96%, 97%, 98%, or 99% identity) to, or the sequence of, SEQ ID NO: 2 (mEnv+).

In a related second aspect, the invention features a stabilized trimer having three gp140 polypeptides in which at least one (e.g., two or each) of the gp140 polypeptides includes an amino acid sequence having substantially the sequence of (e.g., 99% or more identity), or the sequence of, SEQ ID NO: 1 (mEnv) or SEQ ID NO: 3 (cEnv).

In some embodiments, the stabilized trimers are heterotrimers. The stabilized polypeptide heterotrimers may include two mosaic Env1 gp140 polypeptides (e.g., mEnv and/or mEnv+) each including an amino acid sequence having at least 90% identity (e.g., at least 91%, 92%, 93%, 94%, 95%, 96%, 97%, 98%, or 99% identity) to, or the sequence of, SEQ ID NO: 1 or 2, and one clade C Env gp140 polypeptide (e.g., "cEnv" having SEQ ID NO: 3) including an amino acid sequence having at least 90% identity (e.g., at least 91%, 92%, 93%, 94%, 95%, 96%, 97%, 98%, or 99% identity) to, or the sequence of, SEQ ID NO: 3 (cEnv) (e.g., two mEnv and one cEnv; two mEnv+ and one cEnv; or one mEnv, one mEnv+, and one cEnv). In other embodiments, the stabilized heterotrimers may include one mosaic Env1 gp140 polypeptide (e.g., mEnv and/or mEnv+) including an amino acid sequence having at least 90% identity (e.g., at least 91%, 92%, 93%, 94%, 95%, 96%, 97%, 98%, or 99% identity) to, or the sequence of, SEQ ID NO: 1 or 2, and two clade C Env gp140 polypeptides (e.g., cEnv) each including an amino acid sequence having at least 90% (e.g., at least 91%, 92%, 93%, 94%, 95%, 96%, 97%, 98%, or 99% identity) to, or the sequence of, SEQ ID NO: 3 (e.g., one mEnv and two cEnv; one mEnv+ and two cEnv). In some embodiments, the stabilized heterotrimer includes a combination of two different mosaic Env1 sequences (e.g., one mEnv and two mEnv+; two mEnv and one mEnv+; or one mEnv, one mEnv+, and cEnv). In some embodiments, the stabilized heterotrimer includes cEnv and two of the same Env1 polypeptides (e.g., two mEnv and one cEnv; two mEnv+ and one cEnv). In other embodiments, the stabilized heterotrimer includes one cEnv and two different mosaic Env1 polypeptides (e.g., one cEnv, one mEnv, and one mEnv+). In yet other embodiments, the stabilized heterotrimer includes two cEnv polypeptides and one mosaic Env1 polypeptide (e.g., two cEnv and one mEnv; or two cEnv and one mEnv+).

Alternatively, stabilized gp140 Env trimers can be prepared in which one or two of the gp140 Env polypeptides in the trimer has a sequence of SEQ ID NO: 4 (mosaic gp140 Env2, "mEnv2") or SEQ ID NO: 5 (mosaic gp140 Env3, "mEnv3"). In another embodiment said stabilized trimers have three gp140 polypeptides in which at least one (e.g., two or each) of the gp140 polypeptides includes an amino acid sequence having at least 90% identity (e.g., at least 91%, 92%, 93%, 94%, 95%, 96%, 97%, 98%, or 99% identity) to, or the sequence of, SEQ ID NO:4 or 5. Preferably, mEnv2 or mEnv3 is modified in a similar manner to that of mEnv, mEnv+, or cEnv, which each possess a trimerization domain, as discussed herein below. Therefore, in some embodiments of the invention, stabilized gp140 Env trimers can be prepared which have the following constituent polypeptides: one mEnv and two mEnv2; two mEnv and one mEnv2; one mEnv+ and two mEnv2; two mEnv+ and one mEnv2; one cEnv and two mEnv2; two cEnv and one mEnv2; one mEnv, one mEnv+, and one mEnv2; one mEnv, one cEnv, and mEnv2; one mEnv+, one cEnv, and one mEnv2; one mEnv and two mEnv3; two mEnv and one mEnv3; one mEnv+ and two mEnv3; two mEnv+ and one mEnv3; one cEnv and two mEnv3; two cEnv and one mEnv3; one mEnv, one mEnv+, and one mEnv3; one mEnv, one cEnv, and mEnv3; one mEnv+, one cEnv, and one mEnv3; one mEnv, one mEnv2, and one mEnv3; one mEnv+, one mEnv2, and one mEnv3; or one cEnv, one mEnv2, and one mEnv3.

In a third aspect, the invention features a composition including a stabilized trimer of the first or second aspect. In an embodiment, the composition of the third aspect includes one or more different stabilized trimer(s). In other embodiments, the different stabilized trimer(s) has three gp140 polypeptides in which at least one (e.g., two or each) of the gp140 polypeptides comprises an amino acid sequence having at least 90% identity (e.g., at least 91%, 92%, 93%, 94%, 95%, 96%, 97%, 98%, or 99% identity) to, or the sequence of, SEQ ID NOs: 1, 2, or 3. In other embodiments, the different stabilized trimer(s) may be a homotrimer or a heterotrimer. In some embodiments, the compositions of the third aspect further include a pharmaceutically acceptable carrier, excipient, or diluent, and/or an adjuvant.

In a fourth aspect, the invention features a vaccine including any one of the compositions of the third aspect. In some embodiments, the vaccine is used for treating or reducing the risk of a human immunodeficiency virus (HIV) infection in a subject in need thereof. In some embodiments, the vaccine elicits production of neutralizing anti-HIV antisera (e.g., neutralizing anti-HIV-1 antisera) after administration to the subject. The anti-HIV antisera can neutralize HIV (e.g., HIV-1), for example, selected from any one or more of clade A, clade B, and clade C.

In a fifth aspect, the invention features a nucleic acid molecule having a nucleotide sequence that encodes at least one (e.g., two, or three or more) gp140 polypeptide, wherein the at least one gp140 polypeptide includes: (a) an amino acid sequence having at least 95% identity (e.g., at least 96%, 97%, 98%, or 99% identity) to, or the sequence of, SEQ ID NO: 1; (b) an amino acid sequence having at least 95% identity (e.g., at least 96%, 97%, 98%, or 99% identity) to, or the sequence of, SEQ ID NO: 2; or (c) an amino acid sequence having the sequence of SEQ ID NO: 3; (d) an amino acid sequence having the sequence of SEQ ID NO:4; (e) an amino acid sequence having the sequence of SEQ ID NO:5 or combinations thereof. In some embodiments, the nucleic acid molecule further includes a nucleotide sequence that encodes one or more different (e.g., a second, third, or fourth) gp140 polypeptides (e.g., gp140 polypeptides having at least 95% identity (e.g., at least 96%, 97%, 98%, or 99% identity) to, or the sequence of, SEQ ID NO: 1, 2, and/or 3). In some embodiments, the nucleic acid molecule includes one or more internal ribosome entry site (IRES) sequences to allow for the expression of multiple peptide or polypeptide chains from the single nucleic acid molecule transcript.

In a sixth aspect, the invention features a vector including one or more nucleic acid molecules of the fifth aspect. In some embodiments, the vector is an adenovirus vector or a poxvirus vector. The adenovirus vector may be derived, for example, from a recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48)). The poxvirus vector may be derived, for example, from modified vaccinia virus Ankara (MVA).

In a seventh aspect, the invention provides a method of treating or reducing the risk of an HIV infection in a subject in need thereof by administering a therapeutically effective amount of a composition of the invention (e.g., any one of the stabilized trimers of the first or second aspect, the compositions of the third aspect, the vaccines of the fourth aspect, the nucleic acid molecules of the fifth aspect, and/or the vectors of the sixth aspect) to the subject, such as a mammal, for example, a human. Treating, according to this seventh aspect of the invention, can be therapeutic or prophylactic.

In an eighth aspect, the invention provides a method of reducing an HIV-mediated activity in a subject infected with HIV by administering a therapeutically effective amount of a composition of the invention (e.g., any one of the stabilized trimers of the first or second aspect, the compositions of the third aspect, the vaccines of the fourth aspect, the nucleic acid molecules of the fifth aspect, and/or the vectors of the sixth aspect) to the subject. In some embodiments, the HIV-mediated activity is viral spread, infection, or cell fusion. Cell fusion may be, for example, target cell entry or syncytial formation. In some embodiments, the HIV titer in the subject infected with HIV is decreased (e.g., by at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more compared to HIV titer of the subject prior to treatment or a control subject infected with HIV but not treated with the composition(s) of the invention) after administration of the vaccine to the subject, such as a mammal, for example, a human.

In some embodiments, the composition (e.g., a vaccine) is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. In some embodiments, the subject is administered at least one dose (e.g., 1, 2, 3, 4, 5, 6, 7, 8, 9, 10, or more doses) of the composition or is administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. In other embodiments, the subject is administered at least two doses (e.g., 2, 3, 4, 5, 6, 7, 8, 9, 10, or more doses) of the composition. In yet another embodiment, the composition is administered to said subject as a prime or a boost composition or in a prime-boost regimen. In a preferred embodiment, one or more composition(s) (e.g., a vaccine) of the invention is administered as a boost.

In another preferred embodiment, the invention features a method of treating or reducing the risk of an HIV infection in a subject by administering, as the prime composition in a prime-boost vaccination regimen, a vaccine that includes a first polypeptide having at least 85% amino acid sequence identity (e.g., 86%, 87%, 88%, 89%, 90%, 91%, 92%, 93%, 94%, 95%, 96%, 97%, 98%, or 99% identity) to, or the sequence of, SEQ ID NO: 6, or at least a first vector (e.g., an adenoviral or poxvirus vector) that includes a first nucleic acid molecule that encodes this first polypeptide. Optionally, a second polypeptide having at least 85% identity (e.g., 86%, 87%, 88%, 89%, 90%, 91%, 92%, 93%, 94%, 95%, 96%, 97%, 98%, or 99% identity) to, or the sequence of, SEQ ID NO: 7 may also be administered in combination with the first polypeptide, or, if a first vector encoding the first polypeptide is administered, a second vector (e.g., an adenoviral or poxvirus vector) including a second nucleic acid molecule that encodes the second polypeptide may be administered in combination with the first vector. The boost composition in this prime-boost regimen may include one or more of the composition(s) of the invention (e.g., any one of the stabilized trimers of the first or second aspect, the compositions of the third aspect, the vaccines of the fourth aspect, the nucleic acid molecules of the fifth aspect, and/or the vectors of the sixth aspect). In still other embodiments, the prime composition in this prime-boost regimen may include polypeptide(s) having the sequence(s) of any one of SEQ ID NOs: 8-32, or one or more vectors including nucleic acid molecules that encode any one of SEQ ID NOs: 8-32, followed by a boost including one or more of the composition(s) of the invention (e.g., any one of the stabilized trimers of the first or second aspect, the compositions of the third aspect, the vaccines of the fourth aspect, the nucleic acid molecules of the fifth aspect, and/or the vectors of the sixth aspect).

In still other embodiments, one or more composition(s) of the invention (e.g., a vaccine) is administered as the prime composition in a prime-boost regimen and the boost composition is a different vaccine composition, e.g., a vaccine that includes one or more polypeptides having at least 85% amino acid sequence identity (e.g., 86%, 87%, 88%, 89%, 90%, 91%, 92%, 93%, 94%, 95%, 96%, 97%, 98%, or 99% identity) to, or the sequence of, any one or more of SEQ ID NOs: 6-32 (preferably the polypeptide of SEQ ID NO: 6 and/or 7), or one or more vectors (e.g., adenoviral or poxvirus vectors) each of which includes a nucleic acid molecule that encodes one or more polypeptides having at least 85% identity (e.g., 86%, 87%, 88%, 89%, 90%, 91%, 92%, 93%, 94%, 95%, 96%, 97%, 98%, or 99% identity) to, or the sequence of, one or more of SEQ ID NOs: 8-32 (preferably the vector encodes the polypeptide of SEQ ID NO: 6 and/or 7).

In some embodiments, the subject may, for example, be administered polypeptide compositions of the invention (e.g., stabilized gp140 Env trimers of the invention) in a non-vectored composition. The polypeptide composition administered may include between approximately 1 µg and 1 mg of stabilized Env trimers, and more preferably between 50 µg and 300 µg of stabilized Env trimers of the invention.

In other embodiments wherein the delivery vector is a virus, the subject can be administered at least about $1 \times 10^3$ viral particles (vp)/dose or between $1 \times 10^1$ and $1 \times 10^{14}$ vp/dose, preferably between $1 \times 10^3$ and $1 \times 10^{12}$ vp/dose, and more preferably between $1 \times 10^5$ and $1 \times 10^{11}$ vp/dose. The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, 20 years or longer post-diagnosis or post-exposure or to HIV. The subject is administered one or more doses of the composition once daily, weekly, monthly, or yearly. When treating an HIV infection, the composition(s) of the invention (e.g., any one of the stabilized trimers of the first, second, or third aspect, the compositions of the fourth or fifth aspect, the vaccines of the sixth aspect, the nucleic acid molecules of the seventh aspect, and/or the vectors of the eighth aspect) may be administered to the subject either before the occurrence of symptoms of an HIV infection or disease/syndrome (e.g., acquired immune deficiency syndrome (AIDS)) or a definitive diagnosis, or after diagnosis or symptoms become evident. The composition(s) may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

In a ninth aspect, the invention provides methods of manufacturing a vaccine for treating or reducing the risk of an HIV infection in a subject in need thereof. The method includes the steps of: (a) contacting a nucleic acid of the second aspect of the invention (e.g., a nucleic acid that further includes a vector of the eighth aspect) with a cell; and (b) expressing the nucleic acid in the cell to form a stabilized trimer. In some embodiments, the method is performed in vitro or ex vivo. In some embodiments, the cell is a bacterial, plant, or mammalian cell (e.g., a human or non-human mammalian cell). In a preferred embodiment, the mammalian cell is a 293T cell.

In a final aspect, the invention features a kit including: (a) a composition of the invention (e.g., any one of the stabilized trimers of the first, second, or third aspect, the compositions of the fourth or fifth aspect, the vaccines of the sixth aspect, the nucleic acid molecules of the seventh aspect, and/or the vectors of the eighth aspect, e.g., a vaccine including mEnv and/or mEnv+trimers and cEnv trimers); (b) a pharmaceutically acceptable carrier, excipient, or diluent; and (c) instructions for use thereof. The kit may optionally include an adjuvant.

In preferred embodiments of all aspects of the invention, the subject is a mammal, preferably a primate, such as a human.

Definitions

As used herein, the term "about" means+/−10% of the recited value. By "adenovirus" is meant a medium-sized (90-100 nm), non-enveloped icosahedral virus that includes a capsid and a double-stranded linear DNA genome. The adenovirus can be a naturally occurring, but isolated, adenovirus (e.g., sAd4287, sAd4310A, or sAd4312) or a recombinant adenovirus (e.g., replication-defective or replication competent sAd4287, sAd4310A, or sAd4312, or a chimeric variant thereof).

As used herein, "administering" is meant a method of giving a dosage of a pharmaceutical composition (e.g., a composition of the invention, such as any one of the vaccines of the first or fourth aspects, the compositions of the third aspect, the nucleic acid molecules of the fifth aspect, and/or the vectors of the sixth aspect) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. The preferred method of administration can vary depending on various factors (e.g., the components of the composition being administered and the severity of the condition being treated).

As used herein, the term "clade" refers to related human immunodeficiency viruses (HIVs) classified according to their degree of genetic similarity. There are currently three groups of HIV-1 isolates: M, N and O. Group M (major strains) consists of at least ten clades, A through J. Group O (outer strains) may consist of a similar number of clades. Group N is a new HIV-1 isolate that has not been categorized in either group M or O. In certain exemplary embodiments, a composition of the invention (e.g., any one of the vaccines of the first or fourth aspects, the compositions of the third aspect, the nucleic acid molecules of the fifth aspect, and/or the vectors of the sixth aspect) as described herein will recognize and raise an immune response (e.g., neutralizing anti-HIV antisera) against two, three, four, five, six, seven, eight, nine, ten or more clades and/or two or more groups of HIV.

Throughout this specification and claims, the word "comprise," or variations such as "comprises" or "comprising," will be understood to imply the inclusion of a stated integer or group of integers but not the exclusion of any other integer or group of integers.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into the gp120 and gp41 Envelope (Env) proteins. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

By "gene product" is meant to include mRNAs transcribed from a gene as well as polypeptides translated from those mRNAs.

By "heterologous nucleic acid molecule" or "heterologous gene" is meant any exogenous nucleic acid molecule (e.g., a nucleic acid molecule encoding an optimized gp140 Env polypeptide of the invention) that can be inserted into the a vector of the invention (e.g., an adenovirus or poxvirus vector) for transfer into a cell, tissue, or organism, for subsequent expression of a gene product of interest or fragment thereof encoded by the heterologous nucleic acid molecule or gene. In a preferred embodiment, the heterologous nucleic acid molecule, which can be administered to a cell or subject as part of the present invention, can include, but is not limited to, a nucleic acid molecule encoding at least one optimized mosaic Env polypeptide (e.g., a mosaic Env1 polypeptide, such as mEnv and mEnv+) and/or a Glade C Env polypeptide (e.g., a clade C Env1 polypeptide, such as cEnv).

By "human immunodeficiency virus" or "HIV" is meant a virus of the genus *Lentivirinae*, part of the family of Retroviridae, and includes, but is not limited to, HIV type 1 (HIV-1) and HIV type 2 (HIV-2), two species of HIV that infect humans.

By "immune response" is meant any response to an antigen or antigenic determinant by the immune system of a subject (e.g., a human). Exemplary immune responses include humoral immune responses (e.g., production of antigen-specific antibodies, e.g., neutralizing antibodies (NAbs)) and cell-mediated immune responses (e.g., lymphocyte proliferation).

As used herein, the term "reducing" with respect to HIV refers to a reduction or decrease of an HIV-mediated activity (e.g., infection, fusion (e.g., target cell entry and/or syncytia formation), viral spread, etc.) and/or a decrease in viral titer. HIV-mediated activity and/or HIV titer may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control subject (e.g., an untreated subject or a subject treated with a placebo).

By "neutralizing antibody" or "NAb" is meant an antibody which either is purified from, or is present in, serum and which recognizes a specific antigen (e.g., HIV Env glycoprotein, such as a gp140 polypeptide or a gp120 polypeptide) and inhibits the effect(s) of the antigen in the host (e.g., a human). As used herein, the antibody can be a single antibody or a plurality of antibodies.

"Nucleic acid" or "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, intemucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

By "optimized" is meant an immunogenic polypeptide that is not a naturally-occurring peptide, polypeptide, or protein, such as a non-naturally occurring viral polypeptide (e.g., a gp140 polypeptide of the invention). Optimized viral polypeptide sequences are initially generated by modifying the amino acid sequence of one or more naturally-occurring viral gene products (e.g., peptides, polypeptides, and proteins, e.g., a viral Env polypeptide, e.g., a viral Env1, Env2, and/or Env3 polypeptide) to increase the breadth, intensity, depth, or longevity of the antiviral immune response (e.g., cellular or humoral immune responses) generated upon immunization (e.g., when incorporated into a composition of the invention, e.g., vaccine of the invention) of a subject (e.g., a human). Thus, the optimized viral polypeptide may correspond to a "parent" viral gene sequence; alternatively, the optimized viral polypeptide may not correspond to a specific "parent" viral gene sequence but may correspond to analogous sequences from various strains or quasi-species of a virus. Modifications to the viral gene sequence that can be included in an optimized viral polypeptide include amino acid additions, substitutions, and deletions. In one embodiment of the invention, the optimized polypeptide is a mosaic envelope protein, such as mosaic Env1 gp140 (see, e.g., U.S. Patent Publication No. 2012/0076812, herein incorporated by reference), or an optimized version thereof, which has been further altered to include a leader/signal sequence for maximal protein expression, cleavage site mutation(s), a factor Xa site, and/or a foldon trimerization domain (see, e.g., SEQ ID NO: 2). Methods of generating an optimized viral polypeptide are described in, e.g., Fisher et al. "Polyvalent Vaccine for Optimal Coverage of Potential T-Cell Epitopes in Global HIV-1 Variants," Nat. Med. 13(1):100-106 (2007) and International Patent Application Publication WO 2007/024941, herein incorporated by reference. Once the optimized viral polypeptide sequence is generated, the corresponding polypeptide can be produced or administered by standard techniques (e.g., recombinant viral vectors, such as the adenoviral vectors disclosed in International Patent Application Publications WO 2006/040330 and WO 2007/104792, herein incorporated by reference) and optionally assembled in conjunction with one or more other viral polypeptides of the invention to form a stabilized polypeptide trimer.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812).

By "recombinant," with respect to a composition (e.g., a vector of the invention, such as an adenovirus or poxvirus vector), is meant a composition that has been manipulated in vitro (e.g., using standard cloning techniques) to introduce changes (e.g., changes to the composition, e.g., adenovirus or poxvirus genome of an adenovirus or poxvirus vector, respectively) that enable binding to or containment of a therapeutic agent and/or that promote the introduction of a therapeutic agent into a subject (e.g., a human) or a host cell. The recombinant composition of the invention may therefore be an adenoviral or poxviral transport vector (e.g., a replication-defective adenoviral or poxviral vector) for delivery of one or more of the stabilized Env polypeptide trimers of the invention.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

As used herein, the term "stabilized polypeptide trimer" refers, but is not limited to, an oligomer that includes a protein and/or polypeptide sequence that increases the stability (e.g., via the presence of one or more oligomerization domains) of the trimeric structure (e.g., reduces dissociation of a trimer into monomeric units). In particular, the stabilized polypeptide trimer is composed of three mosaic Env proteins (e.g., Env1, Env2, and/or Env3), three clade C Env proteins, or a combination of one or more mosaic Env proteins and one or more clade C Env proteins, in which at least one Env protein includes an oligomerization domain. An "oligomerization domain" refers, but is not limited to, a polypeptide sequence that can be used to increase the stability of an oligomeric envelope protein such as, e.g., to increase the stability of a HIV gp140 trimer. Oligomerization domains can be used to increase the stability of homooligomeric polypeptides as well as heterooligomeric polypeptides. Oligomerization domains are well known in the art, and include "trimerization domains." A trimerization domain refers to an oligomerization domain that stabilizes trimeric polypeptides (e.g., trimers consisting of one or more of the gp140 polypeptides of the invention). Examples of trimerization domains include, but are not limited to, the T4-fibritin "foldon" trimerization domain; the coiled-coil trimerization domain derived from GCN4 (Yang et al. (2002) J. Virol. 76:4634); and the catalytic subunit of $E.$ $coli$ aspartate transcarbamoylase as a trimer tag (Chen et al. (2004) J. Virol. 78:4508).

A "subject" is a vertebrate, such as a mammal (e.g., a human). Mammals also include, but are not limited to, farm animals (such as cows), sport animals (e.g., horses), pets (such as cats and dogs), mice, and rats. A subject to be treated according to the methods described herein (e.g., a subject having an HIV infection or a subject at risk of an HIV infection) may be one who has been diagnosed by a medical practitioner as having such a condition. Diagnosis may be performed by any suitable means. A subject in whom the risk of an HIV infection is to be reduced or prevented may or may not have received such a diagnosis. One skilled in the art will understand that a subject to be treated according to the present invention may have been subjected to standard tests or may have been identified, without examination, as one at high risk due to the presence of one or more risk factors (e.g., a needle stick or known exposure to HIV or an HIV infected individual).

By "having substantially the sequence of" with respect to constructs of the invention is meant having at least 99% sequence identity to a recited reference sequence (e.g., having no more than 7 amino acid residue differences, e.g., 1, 2, 3, 4, 5, or 6 amino acid residue differences (e.g., additions, deletions, or conservative amino acid substitutions), relative to a recited reference sequence).

By "therapeutically effective amount" is meant an amount of a therapeutic agent that alone, or together with one or more additional (optional) therapeutic agents, produces beneficial or desired results upon administration to a mammal. The therapeutically effective amount depends upon the context in which the therapeutic agent is applied. For example, in the context of administering a vaccine composition including a therapeutic agent such as a stabilized gp140 timer of the invention, the therapeutically effective amount of the vaccine composition is an amount sufficient to achieve a reduction in the level of HIV (e.g., as measured by a stabilization or decrease in HIV titer compared to a non-treated control), and/or an increase in the level of neutralizing anti-HIV antisera (e.g., as measured by an increase in serum neutralizing antibody levels relative to a non-treated control in a luciferase-based virus neutralization assay) as compared to a response obtained without administration of a composition of the invention (e.g., a vaccine composition), and/or to prevent the propagation of an infectious virus (e.g., HIV) in a subject (e.g., a human) having an increased risk of viral infection. Ideally, a therapeutically effective amount provides a therapeutic effect without causing a substantial cytotoxic effect in the subject. In general, a therapeutically effective amount of a composition administered to a subject (e.g., a human) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "vaccine," as used herein, is defined as material used to provoke an immune response (e.g., the production of neutralizing anti-HIV antisera). Administration of the vaccine to a subject may confer at least partial immunity against HIV infection.

As used herein, the term "vector" is meant to include, but is not limited to, a virus (e.g., adenovirus or poxvirus), naked DNA, oligonucleotide, cationic lipid (e.g., liposome), cationic polymer (e.g., polysome), virosome, nanoparticle, or dentrimer. By "adenovirus vector" is meant a composition that includes one or more genes (non-structural or structural), or fragments thereof, from an adenoviral species (e.g., adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48))) that may be used to transmit one or more heterologous genes (e.g., one or more of the optimized gp140 polypeptides of the invention) from a viral or non-viral source to a subject or a host. The nucleic acid material of the viral vector may be encapsulated, e.g., in a lipid membrane or by structural proteins (e.g., capsid proteins), that may include one or more viral polypeptides (e.g., an envelope glycoprotein). The viral vector can be used to infect cells of a subject, which, in turn, promotes the translation of the heterologous gene(s) of the viral vector into a protein product (e.g., one or more of the gp140 Env polypeptides described herein, such that a stabilized trimer of the invention is formed).

The term "virus," as used herein, is defined as an infectious agent that is unable to grow or reproduce outside a host cell and that infects mammals (e.g., humans) or birds.

Other features and advantages of the invention will be apparent from the following Detailed Description, the drawings, and the claims.

BRIEF DESCRIPTION OF THE DRAWINGS

FIG. 1A shows the amino acid sequence of a mosaic human immunodeficiency virus (HIV) gp140 Envelope (Env) polypeptide (mEnv; SEQ ID NO: 1) of the invention. The boxed region identifies the signal/leader sequence; the underlined region identifies gp120; the plain text region identifies the gp41 ectodomain; and the double-underscored region identifies the T4-fibritin "foldon" trimerization/oligomerization domain.

FIG. 1B shows the amino acid sequence of a mosaic HIV gp140 Env polypeptide (mEnv+; SEQ ID NO: 2) of the invention. This polypeptide sequence has been further optimized and includes a different signal/leader sequence to maximize protein expression (boxed region); the addition of cleavage site-inactivating mutations (E/E substitution mutations) (circled residues); and the addition of a Factor Xa site (zig-zag underlined region). Other regions are noted as in FIG. 1A.

FIG. 1C shows the amino acid sequence of an optimized clade C Env polypeptide (cEnv; SEQ ID NO: 3) of the invention. All regions are noted as in FIG. 1B.

DETAILED DESCRIPTION OF THE INVENTION

Figure 2:
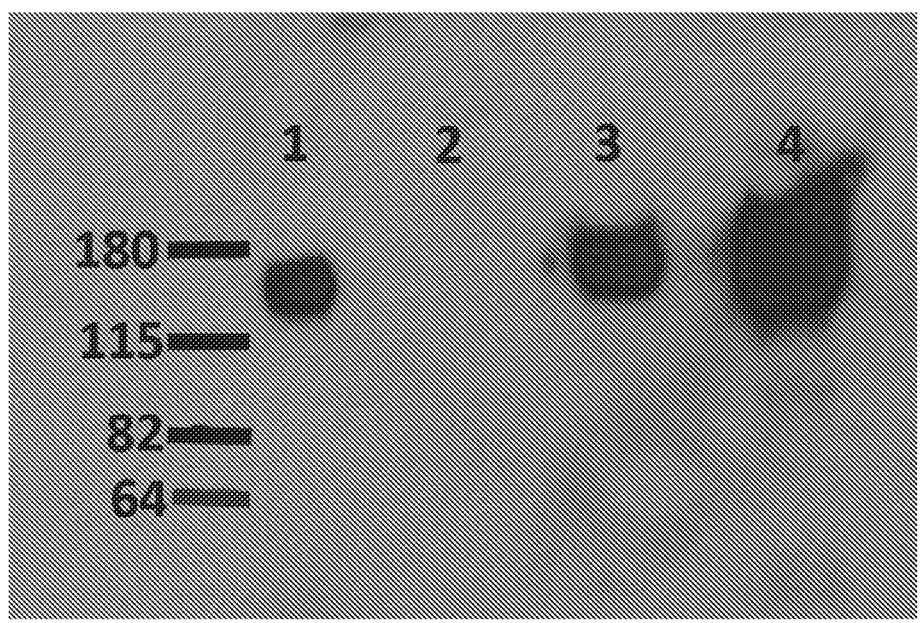
FIG. 2 is a Western blot showing the expression levels of mEnv and mEnv+ in lanes 3 and 4, respectively, compared to cEnv and an expression vector control (pVRC8400) in lanes 1 and 2, respectively.

Most antibodies induced by human immunodeficiency virus (HIV) (e.g., HIV type 1 (HIV-1)) are ineffective at preventing initiation or spread of infection, as they are either non-neutralizing or narrowly isolate-specific. One of the biggest challenges in HIV vaccine development is to design a HIV envelope immunogen that can induce protective, neutralizing antibodies effective against the diverse HIV strains that characterize the global pandemic. Indeed, the generation of "broadly neutralizing" antibodies that recognize relatively conserved regions on the envelope glycoprotein are rare. The present invention is based in part on the discovery of stabilized trimeric HIV envelope (Env) proteins and combinations thereof that elicit a surprisingly broad neutralizing antibody response in vivo.

Stabilized Gp140 Env Trimers of the Invention

The invention features novel stabilized HIV gp140 Env polypeptide trimers. Stabilized trimers of the invention feature optimized gp140 Env polypeptides. These polypeptides may have, or may be modified to include, one or more of the following domains and/or mutations. The gp140 Env polypeptide constituents may include a T4-fibritin "foldon" trimerization domain sequence to support stable trimer formation (see, e.g., FIGS. 1A, 1B, and 1C, depicting the amino acid sequences of mEnv (SEQ ID NO: 1), mEnv+(SEQ ID NO: 2), and cEnv (SEQ ID NO: 3), respectively, which each include a C-terminal trimerization domain). The optimized gp140 Env polypeptides may also include cleavage site mutations to enhance stability, for example, by eliminating cleavage by a peptidase (see, e.g., FIGS. 1B and 1C, which depict the mutated residues as circled residues in the mEnv+ and cEnv amino acid sequence, respectively, between the gp120 and gp41 moieties). The optimized gp140 Env polypeptides may additionally have a signal/leader sequence to maximize protein expression (see, e.g., the signal/leader sequence of mEnv+ or cEnv, demarcated in FIGS. 1B and 1C, respectively). Further, the optimized gp140 Env polypeptides may include a Factor Xa cleavage site (SRIEGR) (SEQ ID NO:33), which may, for example, be incorporated upstream of (N-terminal to) the trimerization domain (see, e.g., FIGS. 1B and 1C, which depict the location of the Factor Xa cleavage site in the amino acid sequence of mEnv+ and cEnv, respectively). As discussed herein below, the stabilized trimers of the invention are preferably homotrimers (e.g., trimers composed of three identical polypeptides). Heterotrimers (e.g., trimers composed of three polypeptides that are not all identical) of the invention are also envisioned.

The stabilized trimers of the invention are preferably stabilized homotrimers that include, for example, three gp140 polypeptides, wherein each of the gp140 polypeptides includes an amino acid sequence having at least 90% identity (e.g., at least 91%, 92%, 93%, 94%, 95%, 96%, 97%, 98%, or 99% identity) to, or the sequence of, SEQ ID NO: 2 (mEnv+). The invention also features stabilized homotrimers including three gp140 polypeptides, wherein each of said gp140 polypeptides includes an amino acid sequence having substantially the sequence of (e.g., 99% or more identity), or the sequence of, SEQ ID NO: 1 (mEnv)

or SEQ ID NO: 3 (cEnv) or SEQ ID NO:4 or SEQ ID NO:5. Exemplary homotrimers of the invention include Trimers 1, 2, and 3 in Table 1 below.

Alternatively, the stabilized trimer of the invention may be a stabilized heterotrimer. For example, the stabilized trimer may be a stabilized heterotrimer that includes a combination of two different mosaic Env1 sequences (e.g., one mEnv and two mEnv+; two mEnv and one mEnv+; or one mEnv, one mEnv+, and cEnv). In some instances, the stabilized heterotrimer includes cEnv and two of the same Env1 polypeptides (e.g., two mEnv and one cEnv; two mEnv+ and one cEnv). In other instances, the stabilized heterotrimer includes one cEnv and two different mosaic Env1 polypeptides (e.g., one cEnv, one mEnv, and one mEnv+).

Alternatively, the stabilized heterotrimer may include one or two constituent Env polypeptides including an amino acid sequence of SEQ ID NO: 4 (mosaic gp140 Env2, "mEnv2") or SEQ ID NO: 5 (mosaic gp140 Env3, "mEnv3"). Preferably, mEnv2 or mEnv3 is modified in a similar manner to that of mEnv, mEnv+, or cEnv, which each possess a trimerization domain, as discussed above and as depicted in FIGS. 1A-1C. Therefore, other stabilized heterotrimers of the invention include trimers having the following constituent polypeptides: one mEnv and two mEnv2; two mEnv and one mEnv2; one mEnv+ and two mEnv2; two mEnv+ and one mEnv2; one cEnv and two mEnv2; two cEnv and one mEnv2; one mEnv, one mEnv+, and one mEnv2; one mEnv, one cEnv, and mEnv2; one mEnv+, one cEnv, and one mEnv2; one mEnv and two mEnv3; two mEnv and one mEnv3; one mEnv+ and two mEnv3; two mEnv+ and one mEnv3; one cEnv and two mEnv3; two cEnv and one mEnv3; one mEnv, one mEnv+, and one mEnv3; one mEnv, one cEnv, and mEnv3; one mEnv+, one cEnv, and one mEnv3; one mEnv, one mEnv2, and one mEnv3; one mEnv+, one mEnv2, and one mEnv3; or one cEnv, one mEnv2, and one mEnv3. Exemplary heterotrimers of the invention include Trimers 4-31 in Table 1 below.

TABLE 1

Exemplary stabilized Env trimers

| Exemplary Trimer | Constituent Polypeptides | | |
|---|---|---|---|
| | Polypeptide 1 | Polypeptide 2 | Polypeptide 3 |
| Trimer 1 | SEQ ID NO: 1 | SEQ ID NO: 1 | SEQ ID NO: 1 |
| Trimer 2 | SEQ ID NO: 2 | SEQ ID NO: 2 | SEQ ID NO: 2 |
| Trimer 3 | SEQ ID NO: 3 | SEQ ID NO: 3 | SEQ ID NO: 3 |
| Trimer 4 | SEQ ID NO: 1 | SEQ ID NO: 2 | SEQ ID NO: 2 |
| Trimer 5 | SEQ ID NO: 1 | SEQ ID NO: 1 | SEQ ID NO: 2 |
| Trimer 6 | SEQ ID NO: 1 | SEQ ID NO: 3 | SEQ ID NO: 3 |
| Trimer 7 | SEQ ID NO: 1 | SEQ ID NO: 1 | SEQ ID NO: 3 |
| Trimer 8 | SEQ ID NO: 2 | SEQ ID NO: 3 | SEQ ID NO: 3 |
| Trimer 9 | SEQ ID NO: 2 | SEQ ID NO: 2 | SEQ ID NO: 3 |
| Trimer 10 | SEQ ID NO: 1 | SEQ ID NO: 2 | SEQ ID NO: 3 |
| Trimer 11 | SEQ ID NO: 1 | SEQ ID NO: 4 | SEQ ID NO: 4 |
| Trimer 12 | SEQ ID NO: 1 | SEQ ID NO: 1 | SEQ ID NO: 4 |
| Trimer 13 | SEQ ID NO: 2 | SEQ ID NO: 4 | SEQ ID NO: 4 |
| Trimer 14 | SEQ ID NO: 2 | SEQ ID NO: 2 | SEQ ID NO: 4 |
| Trimer 15 | SEQ ID NO: 3 | SEQ ID NO: 4 | SEQ ID NO: 4 |
| Trimer 16 | SEQ ID NO: 3 | SEQ ID NO: 3 | SEQ ID NO: 4 |
| Trimer 17 | SEQ ID NO: 1 | SEQ ID NO: 2 | SEQ ID NO: 4 |
| Trimer 18 | SEQ ID NO: 1 | SEQ ID NO: 3 | SEQ ID NO: 4 |
| Trimer 19 | SEQ ID NO: 2 | SEQ ID NO: 3 | SEQ ID NO: 4 |
| Trimer 20 | SEQ ID NO: 1 | SEQ ID NO: 5 | SEQ ID NO: 5 |
| Trimer 21 | SEQ ID NO: 1 | SEQ ID NO: 1 | SEQ ID NO: 5 |
| Trimer 22 | SEQ ID NO: 2 | SEQ ID NO: 5 | SEQ ID NO: 5 |
| Trimer 23 | SEQ ID NO: 2 | SEQ ID NO: 2 | SEQ ID NO: 5 |
| Trimer 24 | SEQ ID NO: 3 | SEQ ID NO: 5 | SEQ ID NO: 5 |
| Trimer 25 | SEQ ID NO: 3 | SEQ ID NO: 3 | SEQ ID NO: 5 |
| Trimer 26 | SEQ ID NO: 1 | SEQ ID NO: 2 | SEQ ID NO: 5 |
| Trimer 27 | SEQ ID NO: 1 | SEQ ID NO: 3 | SEQ ID NO: 5 |
| Trimer 28 | SEQ ID NO: 2 | SEQ ID NO: 3 | SEQ ID NO: 5 |
| Trimer 29 | SEQ ID NO: 1 | SEQ ID NO: 4 | SEQ ID NO: 5 |
| Trimer 30 | SEQ ID NO: 2 | SEQ ID NO: 4 | SEQ ID NO: 5 |
| Trimer 31 | SEQ ID NO: 3 | SEQ ID NO: 4 | SEQ ID NO: 5 |

Stabilized Gp140 Env Trimer Compositions of the Invention

Any one of the stabilized gp140 Env trimers of the invention, such as those described above, can be included in compositions (e.g., pharmaceutical compositions). Accordingly, the invention features a composition including at least one of the stabilized gp140 Env trimers described above (e.g., at least 2, 3, 4, 5, or more different types of stabilized gp140 Env trimers may be included in a single composition or vaccine). For example, a composition including a homotrimer of mEnv or mEnv+ may additionally include an additional stabilized trimer form, for example, an additional stabilized trimer form that includes three gp140 polypeptides, wherein each of the gp140 polypeptides comprises an amino acid sequence having at least 90% identity (e.g., at least 91%, 92%, 93%, 94%, 95%, 96%, 97%, 98%, or 99% identity) to, or the sequence of, SEQ ID NO: 3 (cEnv).

The compositions may include a stabilized homotrimer including three mosaic Env1 polypeptides, for example, three polypeptides of mEnv or three polypeptides of mEnv+ or three optimized clade C Env polypeptides, such as the cEnv polypeptide of SEQ ID NO: 3.

Alternatively, the compositions may also include a stabilized heterotrimer. For example, the composition (e.g., a vaccine) may include at least one stabilized heterotrimer that includes a combination of two different mosaic Env1 sequences (e.g., one mEnv and two mEnv+; and two mEnv and one mEnv+). In some embodiments, the composition (e.g., a vaccine) includes at least one stabilized heterotrimer that includes cEnv and Env1 polypeptide (e.g., two mEnv and one cEnv; two mEnv+ and one cEnv; two cEnv and one mEnv; and two cEnv and one mEnv+). In other embodiments, the compositions include at least one stabilized heterotrimer that includes one cEnv and two different mosaic Env1 polypeptides (e.g., one cEnv, one mEnv, and one mEnv+).

Optionally, the compositions may include at least one stabilized heterotrimer having one or two constituent Env polypeptides including an amino acid sequence of SEQ ID NO: 4 (mosaic gp140 Env2, "mEnv2") or SEQ ID NO: 5 (mosaic gp140 Env3, "mEnv3"). As noted above, preferably, mEnv2 or mEnv3 may be, and is preferably, modified in a similar manner to that of mEnv, mEnv+, or cEnv, which each possess a trimerization domain, as discussed above and depicted in FIGS. 1A-1C. Therefore, other vaccines of the invention may include stabilized heterotrimers having the following constituent polypeptides: one mEnv and two mEnv2; two mEnv and one mEnv2; one mEnv+ and two mEnv2; two mEnv+ and one mEnv2; one cEnv and two mEnv2; two cEnv and one mEnv2; one mEnv, one mEnv+, and one mEnv2; one mEnv, one cEnv, and mEnv2; one mEnv+, one cEnv, and one mEnv2; one mEnv and two mEnv3; two mEnv and one mEnv3; one mEnv+ and two mEnv3; two mEnv+ and one mEnv3; one cEnv and two mEnv3; two cEnv and one mEnv3; one mEnv, one mEnv+, and one mEnv3; one mEnv, one cEnv, and mEnv3; one mEnv+, one cEnv, and one mEnv3; one mEnv, one mEnv2, and one mEnv3; one mEnv+, one mEnv2, and one mEnv3; or one cEnv, one mEnv2, and one mEnv3.

Any one of the compositions of the invention may further include a pharmaceutically acceptable carrier, excipient, or diluent, and/or an adjuvant.

Stabilized Gp140 Env Trimer Vaccines of the Invention

The invention features vaccines including at least one of the compositions of the invention described herein and above. The vaccine may be used for treating or reducing the risk of a human immunodeficiency virus (HIV) infection in a subject in need thereof. For example, the vaccine may elicit production of neutralizing anti-HIV antisera (e.g., neutralizing anti-HIV-1 antisera) after administration to the subject. The anti-HIV antisera may also be able to neutralize HIV (e.g., HIV-1), for example, selected from any one or more of clade A, clade B, and clade C.

Nucleic Acid Molecules of the Invention

In some embodiments, the vaccines of the invention include one or more nucleic acid molecules of the invention, such as a nucleic acid molecule having a nucleotide sequence that encodes a gp140 polypeptide, in which the gp140 polypeptide includes (a) an amino acid sequence having at least 95% identity (e.g., 96%, 97%, 98%, 99%, or 100% identity) to SEQ ID NO: 1, (b) an amino acid sequence having at least 95% identity (e.g., 96%, 97%, 98%, 99%, or 100% identity) to SEQ ID NO: 2, and/or (c) an amino acid sequence having the sequence of SEQ ID NO: 3, (d) an amino acid sequence having the sequence of SEQ ID NO:4, (e) an amino acid sequence having the sequence of SEQ ID NO:5 and/or combinations thereof. As discussed below, vectors (e.g., viral vectors, such as an adenovirus or poxvirus vector) of the invention can include one or more of these nucleic acid molecules. Accordingly, vaccines of the invention may include one or more of these vectors. The stabilized gp140 Env trimer polypeptides of the invention, as well as vaccines, nucleic acids, and vectors that incorporate one or more optimized gp140 Env polypeptides, can be recombinantly expressed in a cell or organism, or can be directly administered to a subject (e.g., a human) infected with, or at risk of becoming infected with, HIV (e.g., HIV-1).

Vectors of the Invention

As noted above, the invention features vectors including one or more of the nucleic acid molecules of the invention. The vector can be, for example, a carrier (e.g., a liposome), a plasmid, a cosmid, a yeast artificial chromosome, or a virus (e.g., an adenovirus vector or a poxvirus vector) that includes one or more of the nucleic acid molecules of the invention.

An adenovirus vector of the invention can be derived from a recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48)). A poxvirus vector of the invention may be derived, for example, from modified vaccinia virus Ankara (MVA). These vectors can include additional nucleic acid sequences from several sources.

Vectors of the invention can be constructed using any recombinant molecular biology technique known in the art. The vector, upon transfection or transduction of a target cell or organism, can be extrachromosomal or integrated into the host cell chromosome. The nucleic acid component of a vector can be in single or multiple copy number per target cell, and can be linear, circular, or concatamerized. The vectors can also include internal ribosome entry site (IRES) sequences to allow for the expression of multiple peptide or polypeptide chains from a single nucleic acid transcript (e.g., a polycistronic vector, e.g., a bi- or tri-cistronic vector).

Vectors of the invention can also include gene expression elements that facilitate the expression of the encoded polypeptide(s) of the invention (e.g., SEQ ID NOs: 1 (mEnv), 2 (mEnv+), and/or 3 (cEnv) or polypeptides having amino acids sequences with at least 90%, 91%, 92$, 93&, 94%, 95%, 96%, 97%, 98%, or 99% sequence identity to SEQ ID NO: 1 or 2). Gene expression elements include, but are not limited to, (a) regulatory sequences, such as viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Also included are plasmid origins of replication, antibiotic resistance or selection genes, multiple cloning sites (e.g., restriction enzyme cleavage loci), and other viral gene sequences (e.g., sequences encoding viral structural, functional, or regulatory elements, such as the HIV long terminal repeat (LTR)).

Exemplary vectors are described below.

Adenovirus Vectors

Recombinant adenoviruses offer several significant advantages for use as vectors for the expression of, for example, one or more of the optimized gp140 Env polypeptides of the invention. The viruses can be prepared to high titer, can infect non-replicating cells, and can confer high-efficiency transduction of target cells ex vivo following contact with a target cell population. Furthermore, adenoviruses do not integrate their DNA into the host genome. Thus, their use as expression vectors has a reduced risk of inducing spontaneous proliferative disorders. In animal models, adenoviral vectors have generally been found to mediate high-level expression for approximately one week. The duration of transgene expression (expression of a nucleic acid molecule of the invention) can be prolonged by using cell or tissue-specific promoters. Other improvements in the molecular engineering of the adenovirus vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., *Proc. Natl. Acad. Sci. USA* 91:6196 (1994) and Kochanek et al., *Proc. Natl. Acad. Sci. USA* 93:5731 (1996), each herein incorporated by reference).

The rare serotype and chimeric adenoviral vectors disclosed in International Patent Application Publications WO 2006/040330 and WO 2007/104792, each incorporated by reference herein, are particularly useful as vectors of the invention. For example, recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48)) can encode and/or deliver one or more of the optimized gp140 Env polypeptides of the invention to facilitate formation and presentation of gp140 Env trimer formation. In some embodiments, one or more recombinant adenovirus vectors can be administered to the subject in order to express gp140 Env polypeptides for formation of stabilized trimers of the invention.

Adeno-Associated Virus (AAV) Vectors

Adeno-associated viruses (AAV), derived from non-pathogenic parvoviruses, can also be used to facilitate delivery and/or expression of one or more of the optimized gp140 Env polypeptides of the invention as these vectors evoke almost no anti-vector cellular immune response, and produce transgene expression lasting months in most experimental systems.

Stabilized trimers of the invention may be produced upon expression of the gp140 Env polypeptides described herein using an AAV vector.

Retrovirus Vectors

Retroviruses are useful for the expression of optimized gp140 Env polypeptides of the invention. Unlike adenoviruses, the retroviral genome is based in RNA. When a retrovirus infects a cell, it will introduce its RNA together with several enzymes into the cell. The viral RNA molecules from the retrovirus will produce a double-stranded DNA copy, called a provirus, through a process called reverse transcription. Following transport into the cell nucleus, the proviral DNA is integrated in a host cell chromosome, permanently altering the genome of the transduced cell and any progeny cells that may derive from this cell. The ability to permanently introduce a gene into a cell or organism is the defining characteristic of retroviruses used for gene therapy. Retroviruses include lentiviruses, a family of viruses including human immunodeficiency virus (HIV) that includes several accessory proteins to facilitate viral infection and proviral integration. Current, "third-generation," lentiviral vectors feature total replication incompetence, broad tropism, and increased gene transfer capacity for mammalian cells (see, e.g., Mangeat and Trono, *Human Gene Therapy* 16(8):913 (2005) and Wiznerowicz and Trono, *Trends Biotechnol.* 23(1):42 (2005), each herein incorporated by reference).

Stabilized trimers of the invention may be produced upon expression of the gp140 Env polypeptides described herein using a retrovirus vector.

Other Viral Vectors

Besides adenoviral and retroviral vectors, other viral vectors and techniques are known in the art that can be used to facilitate delivery and/or expression of one or more of the optimized gp140 Env polypeptides of the invention in a cell (e.g., a blood cell, such as a lymphocyte) or subject (e.g., a human) in order to promote formation of the trimers of the invention. These viruses include poxviruses (e.g., vaccinia virus and modified vaccinia virus Ankara (MVA); see, e.g., U.S. Pat. Nos. 4,603,112 and 5,762,938, each incorporated by reference herein), herpesviruses, togaviruses (e.g., Venezuelan Equine Encephalitis virus; see, e.g., U.S. Pat. No. 5,643,576, incorporated by reference herein), picornaviruses (e.g., poliovirus; see, e.g., U.S. Pat. No. 5,639,649, incorporated by reference herein), baculoviruses, and others described by Wattanapitayakul and Bauer (*Biomed. Pharmacother.* 54:487 (2000), incorporated by reference herein).

Naked DNA and Oligonucleotides

Naked DNA or oligonucleotides encoding one or more of the optimized gp140 Env polypeptides of the invention can also be used to express these polypeptides in a cell or a subject (e.g., a human) in order to promote formation of the trimers of the invention. See, e.g., Cohen, *Science* 259:1691-1692 (1993); Fynan et al., *Proc. Natl. Acad. Sci. USA,* 90:11478 (1993); and Wolff et al., *BioTechniques* 11:474485 (1991), each herein incorporated by reference. This is the simplest method of non-viral transfection. Efficient methods for delivery of naked DNA exist, such as electroporation and the use of a "gene gun," which shoots DNA-coated gold particles into a cell using high pressure gas and carrier particles (e.g., gold).

Lipoplexes and Polyplexes

To improve the delivery of a nucleic acid encoding one or more of the optimized gp140 Env polypeptides of the invention into a cell or subject in order to promote formation of the trimers of the invention, lipoplexes (e.g., liposomes) and polyplexes can be used to protect the nucleic acid from undesirable degradation during the transfection process. The nucleic acid molecules can be covered with lipids in an organized structure like a micelle or a liposome. When the organized structure is complexed with the nucleic acid molecule it is called a lipoplex. There are three types of lipids: anionic (negatively-charged), neutral, or cationic (positively-charged). Lipoplexes that utilize cationic lipids have proven utility for gene transfer. Cationic lipids, due to their positive charge, naturally complex with the negatively-charged nucleic acid. Also as a result of their charge they interact with the cell membrane, endocytosis of the lipoplex occurs, and the nucleic acid is released into the cytoplasm. The cationic lipids also protect against degradation of the nucleic acid by the cell.

Complexes of polymers with nucleic acids are called polyplexes. Most polyplexes consist of cationic polymers and their production is regulated by ionic interactions. One large difference between the methods of action of polyplexes and lipoplexes is that polyplexes cannot release their nucleic acid load into the cytoplasm, so, to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Exemplary cationic lipids and polymers that can be used in combination with one or more of the nucleic acid molecules encoding one or more of the optimized gp140 Env polypeptides of the invention to form lipoplexes or polyplexes include, but are not limited to, polyethylenimine, lipofectin, lipofectamine, polylysine, chitosan, trimethylchitosan, and alginate.

Hybrid Methods

Several hybrid methods of gene transfer combine two or more techniques. Virosomes, for example, combine lipoplexes (e.g., liposomes) with an inactivated virus. This approach has been shown to result in more efficient gene transfer in respiratory epithelial cells compared to either viral or liposomal methods alone. Other methods involve mixing other viral vectors with cationic lipids or hybridizing viruses. Each of these methods can be used to facilitate transfer of one or more of the nucleic acid molecules of the invention encoding one or more of the optimized gp140 Env polypeptides of the invention into a cell or subject in order to promote formation of the trimers of the invention.

Dendrimers

Dendrimers may be also be used to transfer one or more of the nucleic acid molecules of the invention encoding one or more of the optimized gp140 Env polypeptides of the invention into a cell or subject in order to promote formation of the trimers of the invention. A dendrimer is a highly branched macromolecule with a spherical shape. The surface of the particle may be functionalized in many ways, and many of the properties of the resulting construct are determined by its surface. In particular it is possible to construct a cationic dendrimer (i.e., one with a positive surface charge). When in the presence of genetic material (e.g., a nucleic acid molecule), charge complimentarily leads to a temporary association of the nucleic acid with the cationic dendrimer. On reaching its destination the dendrimer-nucleic acid complex is then taken into the cell via endocytosis.

Methods of Treatment Using the Compositions of the Invention

In vivo Administration

The invention features methods for the in vivo administration of a therapeutically effective amount of one or more of the compositions (i.e., vaccines, vectors, stabilized trimer (s), nucleic acids, polypeptides, stabilized trimer, or other composition thereof described herein) of the invention to a subject (e.g., a human, e.g., a human infected with HIV or a human at risk of an HIV infection) in need thereof. Upon administering one or more of the compositions of the invention to the subject, the stabilized trimers of the invention can elicit protective or therapeutic immune responses (e.g., cellular or humoral immune responses, e.g., neutralizing anti-HIV antisera production, e.g., anti-HIV antisera that neutralizes HIV selected from clade A, clade B, and/or clade C HIV) directed against the viral immunogens.

The method may be used to treat or reduce the risk of an HIV infection in a subject in need thereof. The subject may be infected with HIV or may be at risk of exposure to HIV. The compositions of the invention can be administered to a subject infected with HIV to treat AIDS. Examples of symptoms of diseases caused by a viral infection, such as AIDS, that can be treated using the compositions of the invention include, for example, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. These symptoms, and their resolution during treatment, may be measured by, for example, a physician during a physical examination or by other tests and methods known in the art.

In cases in which the subject is infected with HIV, the method may be used to reduce an HIV-mediated activity (e.g., infection, fusion (e.g., target cell entry and/or syncytia formation), viral spread, etc.) and/or to decrease HIV titer in the subject. HIV-mediated activity and/or HIV titer may be decreased, for example, by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control subject (e.g., an untreated subject or a subject treated with a placebo).

One or more of the compositions of the invention may also be administered in the form of a vaccine for prophylactic treatment of a subject (e.g., a human) at risk of an HIV infection.

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions.

The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the chimeric Ad5 vector composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

Compositions according to the invention described herein may be formulated to release the composition immediately upon administration (e.g., targeted delivery) or at any predetermined time period after administration using controlled or extended release formulations Administration of the composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastrointestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, for example, appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide pre-infection prophylaxis or after a subject has been diagnosed with an HIV infection or a disease with an etiology traceable to an HIV infection (e.g., AIDS). The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-infection or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis or post-infection to HIV. The subject can be administered a single dose of the composition(s) (or, e.g., 2, 3, 4, 5, 6, 7, 8, 9, 10, or more doses) or the subject can be administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. The composition(s) may also be administered to said subject as a prime or a boost composition or in a prime-boost regimen. In a preferred embodiment, the composition (e.g., vaccine) of the invention is administered as a boost following administration of an additional composition (e.g., vaccine) as a prime, where the prime includes at least a first vector including a first nucleic acid molecule that encodes a polypeptide having at least 85% amino acid sequence identity (e.g., 86%, 87%, 88%, 89%, 90%, 91%, 92%, 93%, 94%, 95%, 96%, 97%, 98%, or 99% identity) to, or the sequence of, SEQ ID NO: 6, and optionally a second vector including a second nucleic acid molecule that encodes a polypeptide having at least 85% identity (e.g., 85%, 86%, 87%, 88%, 89%, 90%, 91%, 92%, 93%, 94%, 95%, 96%, 97%, 98%, or 99% identity) to, or the sequence of, SEQ ID NO: 7. The boost in this regimen includes one or more of the composition(s) of the invention (e.g., any one of the stabilized trimers, the compositions, the vaccines, the nucleic acid molecules, and/or the vectors of the invention). In still other embodiments, the prime includes at least a first vector including a nucleic acid molecule that encodes a polypeptide having the sequence of any one of SEQ ID NOs: 8-32. Alternatively, the composition (e.g., vaccine) of the invention is administered as a prime. In some embodiments where the composition of the invention is administered as a prime, a different vaccine (e.g., a vaccine including at least a first vector including a first nucleic acid molecule that encodes a polypeptide having at least 85% amino acid sequence identity (e.g., 86%, 87%, 88%, 89%, 90%, 91%, 92%, 93%, 94%, 95%, 96%, 97%, 98%, or 99% identity) to, or the sequence of, SEQ ID NO: 6, and optionally a second vector including a second nucleic acid molecule that encodes a polypeptide having at least 85% identity (e.g., 85%, 86%, 87%, 88%, 89%, 90%, 91%, 92%, 93%, 94%, 95%, 96%, 97%, 98%, or 99% identity) to, or the sequence of, SEQ ID NO: 7; or a vaccine including at least a first vector including a nucleic acid molecule that encodes a polypeptide having the sequence of any one of SEQ ID NOs: 8-32) is administered as a boost.

When treating disease (e.g., AIDS), the compositions of the invention may be administered to the subject either before the occurrence of symptoms or a definitive diagnosis or after diagnosis or symptoms become evident. For example, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of any one or more of the optimized gp140 Env nucleic acids required to support formation of one or more of the stabilized trimers of the invention and/or one or more of the stabilized trimers of the invention of the invention and, if desired, one or more immunomodulatory agents, such as in a sealed package of tablets or capsules, or in a suitable dry powder inhaler (DPI) capable of administering one or more doses.

Dosages

The dose of a composition of the invention (e.g., a vaccine including one or more of the stabilized gp140 Env trimers of the invention) or the number of treatments using a composition of the invention may be increased or decreased based on the severity of, occurrence of, or progression of, the HIV infection and/or disease related to the HIV infection (e.g., AIDS) in the subject (e.g., based on the severity of one or more symptoms of HIV infection/AIDS described above).

The stabilized gp140 Env trimer compositions of the invention can be administered in a therapeutically effective amount that provides an immunogenic and/or protective effect against HIV or target protein of HIV (e.g., gp140). The subject may, for example, be administered polypeptide compositions of the invention (e.g., stabilized gp140 Env trimers of the invention) in a non-vectored composition. The polypeptide composition administered may include between approximately 1 µg and 1 mg of stabilized Env trimers, and more preferably between 50 µg and 300 µg of stabilized Env trimers of the invention.

Alternatively, the subject may be administered, in the form of a viral vector, at least about $1 \times 10^3$ viral particles (vp)/dose or between $1 \times 10^1$ and $1 \times 10^{14}$ vp/dose, preferably between $1 \times 10^3$ and $1 \times 10^{12}$ vp/dose, and more preferably between $1 \times 10^5$ and $1 \times 10^{11}$ vp/dose.

Viral particles include nucleic acid molecules encoding one or more of the optimized gp140 Env polypeptides of the invention and are surrounded by a protective coat (a protein-based capsid with hexon and fiber proteins). Viral particle number can be measured based on, for example, lysis of vector particles, followed by measurement of the absorbance at 260 nm (see, e.g., Steel, Curr. Opin. Biotech., 1999).

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessel epithelial cells, nasal epithelial cells, or pulmonary epithelial cells). The composition is preferably administered in an amount that provides a sufficient level of the stabilized gp140 Env trimer gene product (e.g., a level of stabilized gp140 Env trimer that elicits an immune response without undue adverse physiological effects in the subject caused by the immunogenic trimer).

In addition, single or multiple administrations of the compositions of the present invention may be given (pre- or post-infection and/or pre- or post-diagnosis) to a subject (e.g., one administration or administration two or more times). For example, subjects who are particularly susceptible to, for example, HIV infection may require multiple treatments to establish and/or maintain protection against the virus. Levels of induced immunity provided by the pharmaceutical compositions described herein can be monitored by, for example, measuring amounts of neutralizing anti-HIV secretory and serum antibodies. The dosages may then be adjusted or repeated as necessary to trigger the desired level of immune response. For example, the immune response triggered by a single administration (prime) of a composition of the invention may not be sufficiently potent and/or persistent to provide effective protection. Accordingly, in some embodiments, repeated administration (boost), such that a prime-boost regimen is established, may significantly enhance humoral and cellular responses to the antigen of the composition.

Alternatively, as applies to recombinant therapy, the efficacy of treatment can be determined by monitoring the level of the one or more optimized gp140 Env trimers expressed by or present in a subject (e.g., a human) following administration of the compositions of the invention. For example, the blood or lymph of a subject can be tested for the immunogenic trimer(s) using, for example, standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.).

A single dose of one or more of the compositions of the invention may achieve protection, pre-infection or pre-diagnosis. In addition, a single dose administered post-infection or post-diagnosis can function as a treatment according to the present invention.

A single dose of one or more of the compositions of the invention can also be used to achieve therapy in subjects being treated for a disease. Multiple doses (e.g., 2, 3, 4, 5, or more doses) can also be administered, in necessary, to these subjects.

Carriers, Excipients, Diluents

Therapeutic formulations of the compositions of the invention (e.g., vaccines, vectors, stabilized trimer(s), nucleic acid molecules, etc.) may be prepared using standard methods known in the art by mixing the active ingredient having the desired degree of purity with optional physiologically acceptable carriers, excipients, or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

Adjuvants

Any one of the compositions of the invention (e.g., vaccines, vectors, stabilized trimer(s), nucleic acid molecules, etc.) can be formulated to include, be administered concurrently with, and/or be administered in series with one or more pharmaceutically acceptable adjuvants to increase the immunogenicity of the composition (e.g., upon administration to a subject in need thereof, e.g., a subject infected with HIV or at risk of an HIV infection). Adjuvants approved for human use include aluminum salts (alum). These adjuvants have been useful for some vaccines including hepatitis B, diphtheria, polio, rabies, and influenza. Other useful adjuvants include Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1,2-dipalmitoyl-s-gly-cero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter.

Ex Vivo Transfection and Transduction

The present invention also provides for the ex vivo transfection or transduction of cells, followed by administration of these cells back into a subject (e.g., human) to allow for the expression of one or more of the optimized gp140 Env polypeptides of the invention that have immunogenic properties. In one embodiment, the cells are autologous to the treated subject. Cells can be transfected or transduced ex vivo with, for example, one or more vectors of the invention to allow for the temporal or permanent expression of one or more of the optimized gp140 Env polypeptides in the treated subject. Upon administering these modified cells to the subject, the one or more vectors of the invention will be expressed, eliciting protective or therapeutic immune responses (e.g., cellular or humoral immune responses, e.g., production of neutralizing anti-HIV antisera) directed against the gp140 immunogenic timer or trimers that form.

Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells and hematopoietic stem cells (HSC), can be isolated and transfected or transduced with, for example, a vector of the invention, and administered to a subject according to the methods of the invention.

The method of transfection or transduction has a strong influence on the strength and longevity of protein expression (e.g., stabilized gp140 trimer expression) in the transfected or transduced cell, and subsequently, in the subject (e.g., human) receiving the cell. The present invention provides vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Kits

The invention provides kits that include a pharmaceutical composition containing a vaccine, vector, stabilized timer, or optimized viral polypeptide of the invention, and a pharmaceutically-acceptable carrier, in a therapeutically effective amount for preventing or treating a viral infection. The kits include instructions to allow a clinician (e.g., a physician or nurse) to administer the composition contained therein.

Preferably, the kits include multiple packages of the single-dose pharmaceutical composition(s) containing an effective amount of a vaccine, vector, stabilized timer, or optimized viral polypeptide of the invention. Optionally, instruments or devices necessary for administering the pharmaceutical composition(s) may be included in the kits. For instance, a kit of this invention may provide one or more pre-filled syringes containing an effective amount of a vaccine, vector, stabilized timer, or optimized viral polypeptide of the invention. Furthermore, the kits may also include additional components such as instructions or administration schedules for a patient infected with or at risk of being infected with a virus to use the pharmaceutical composition (s) containing a vaccine, vector, stabilized timer, or optimized viral polypeptide of the invention.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The present invention is illustrated by the following examples, which are in no way intended to be limiting of the invention.

Example 1. Materials and Methods

Western Blot Immunodetection

Volumes containing 10-μg equivalents of DNA expression vectors pVRC8400 empty, pVRC8400 mosaic gp140 version-1 (expression vector for a polypeptide including the amino acid sequence of SEQ ID NO: 1), or pVRC8400 mosaic gp140 version-2 (expression vector for a polypeptide including the amino acid sequence of SEQ ID NO: 2) were each made up to 100 μl with Dulbeco's Modified Eagle Medium (DMEM; Invitrogen). 40 μl of Lipofectamine (Invitrogen) transfection reagent was then added 60 μl DMEM and 100 μl of this mix added to each DNA vector followed by gentle agitation and incubation at room temperature for 30 minutes. 293T cells grown to approximately 70-80% confluency in T-25 flasks were washed once with 2.5 ml DMEM, 2.3 ml of DMEM added followed by 200 μl DNA/Lipofectamine mix. Cells were then incubated at 37° C., 10% $CO_2$ for 48 hours. 48 hours post-transfection, 0.5 ml of supernatant from each T-25 flask was harvested, briefly spun and 20 μl placed in a fresh eppendorf tube. 5 μl of 5× reducing sample buffer (Pierce) was added to each tube, each sample heated for 5 minutes at 100° C. and then place on ice to cool. 20 μl of each sample was loaded on a 4-15% pre-cast SDS-PAGE (Biorad), and the gel run at 150V for approximately 70 minutes. Transfer of protein from gel to membrane was performed using the iblot dry blotting system (Invitrogen) as per vendor protocol using PVDF gel transfer stacks. Membrane blocking was performed overnight at 4° C. in 20 ml of PBS-T Block (i.e., Dulbeco's phosphate buffered saline (Invitrogen), containing 0.2% V/V Tween 20 (Sigma) and 5% W/V non-fat milk powder) on an orbital shaker. 10 μl of monoclonal HRP conjugated anti-His tag antibody (Qiagen) was then added to 20 ml PBS-T Block (1:2000 dilution) followed by incubation on an orbital shaker at room temperature for 1 hour. Membranes were washed 5 times in PBS-T block, membranes touch dried on absorbent paper to remove excess block, and for detection, Amersham ECL Plus Western Blotting Detection System (GE Healthcare) was utilized.

Roller Bottle Transfection and Protein Purification

DMEM growth media supplemented with 10% Fetal Bovine Serum (FBS) was used to grow 293T to confluence in Cell Bind® roller bottles (Corning), growth media removed, followed by addition of 250 ml of pre-warmed Freestyle 293 expression medium (Invitrogen) and incubation for 2 hours at 37° C., 5% $CO_2$. 250 μg of DNA expression vector pVRC8400 mosaic gp140 version-2 was mixed with 320 μl of polyethylenimine (PEI) (1 mg/ml) added to 20 ml of room temperature freestyle 293 medium, incubated at room temperature for 20 minutes and then added in each roller bottle followed by incubation for 6 days in 37° C., 5% $CO_2$. The cell supernatant was harvested at 6 days after medium change. The Histidine-tagged optimized mosaic gp140 Env version-2 protein, including SEQ ID NO: 2, was purified by Ni-NTA (Qiagen) followed by size-exclusion chromatography. Briefly, after a clarifying spin and the addition of imidazole to the final concentration of 10 mM, the cell supernatant was loaded onto a nickel column at a flow rate of 0.8 mL/min and was washed with 20 mM imidazole in PBS followed by further washing with 40 mM imidazole in PBS. The protein then was eluted with 300 mM imidazole in PBS. The fractions containing the purified protein were pooled, concentrated, and further purified by gel-filtration chromatography on Superose 6 (GE Healthcare) in a column running buffer containing 25 mM Tris (pH 7.5) and 150 mM NaCl. The purified proteins were concentrated, frozen in liquid nitrogen, and stored at −80° C.

Animals and Immunizations

Outbred female Hartley guinea pigs (Elm Hill Labs) were housed at the Animal Research Facility of Beth Israel Deaconess Medical Center under protocols approved by the Institutional Animal Care and Use Committee. Guinea pigs were immunized by bilateral intramuscular injections in the upper quadriceps with clade C gp140 Env polypeptide (i.e., homotrimer of three molecules including the amino acid sequence of SEQ ID NO: 3), mosaic gp140 Env (i.e., homotrimer of three molecules including the amino acid sequence of SEQ ID NO: 1), or a clade C gp140 Env/mosaic gp140 Env mixture (100 μg/animal) at 4-week intervals (weeks 0, 4, and 8) using 500 μl of a dual adjuvant combination comprising 15% (v/v) oil-in-water Emulsigen (MVP Laboratories)/PBS and 50 μg of immunostimulatory di-nucleotide CpG DNA (5'-TCGTCGTTGTCGTTTTGTCGTT-3') (SEQ ID NO:34) (Midland Reagent Company). The clade C gp140 Env/mosaic gp140 Env mixture contained 50 μg of each protein. Serum samples were obtained from the vena cava of anesthetized animals 4 weeks after each immunization.

Neutralizing Antibody Assay in TZM.bl Cells

Neutralizing antibody responses against HIV-1 Env pseudoviruses were measured using luciferase-based virus neutralization assays in TZM.bl cells. These assays measure the reduction in luciferase reporter gene expression in TZM-bl cells following a single round of virus infection. The $ID_{50}$ was calculated as the serum dilution that resulted in a 50% reduction in relative luminescence units compared with the virus control wells after the subtraction of cell control relative luminescence units. Briefly, threefold serial dilutions of serum samples were performed in duplicate (96-well flat-bottomed plate) in 10% DMEM growth medium (100 µl per well). Virus was added to each well in a volume of 500, and the plates were incubated for 1 hour at 37° C. Then TZM.bl cells were added ($1 \times 10^4$ per well in 100 µl volume) in 10% DMEM growth medium containing diethylaminoethyldextran (Sigma) at a final concentration of 11 µg/ml. Murine leukemia virus (MuLV) negative controls were included in all assays. HIV-1 Envelope pseudoviruses included clade A (MS208.A1 and Q23.17) isolates, clade B (SF162.LS, BaL.26, SS1196.1 and 6535.3), and clade C (MW965.26, TV1.21, ZM109F.PB4 and ZM197M.PB7) isolates.

Example 2. Generation of Optimized Mosaic Gp140 Env1 Trimers of the Invention mEnv+(polypeptide including the amino acid sequence of SEQ ID NO: 2) has been modified from mEnv (polypeptide including the amino acid sequence of SEQ ID NO: 1) in the following manner. First, the leader peptide secretion sequence has been made identical to that used in the stabilized clade C gp140 Env (cEnv) trimer polypeptide constituent (SEQ ID NO: 3). Second, cleavage site mutations have been incorporated between gp120 and gp41 moieties to further enhance stability. Third, a factor Xa protease cleavage site (SRIEGR) (SEQ ID NO:33) has been incorporated upstream of the foldon trimerization domain. The amino acid sequences of the three Env polypeptides (SEQ ID NOs: 1-3) and the specific modifications present in each are depicted in FIGS. 1A-1C.

Surprisingly, these modifications resulted in a remarkably stabilized gp140 Env1 trimer (e.g., an mEnv+ trimer of the invention). In order to assess stability, we first compared the expression levels of mEnv+ relative to mEnv by Western blot analysis. To this end, T-25 flasks containing 80% confluent 293T cells were transfected with eukaryotic expression vector pVRC8400 expressing mEnv or mEnv+ using lipofectamine 2000 (Invitrogen) and 10µl of each supernatant analyzed by Western blot immunodetection using anti-Histidine tag HRP (Qiagen). FIG. 2 depicts a Western blot showing the expression levels of mEnv and mEnv+ in lanes 3 and 4, respectively. Notably, the expression levels of mEnv+ were remarkably higher compared to that of mEnv or cEnv, which was used as a positive control (see lane 1). In this experiment, empty pVRC8400 was used as a negative control (see lane 2).

Figure 3:
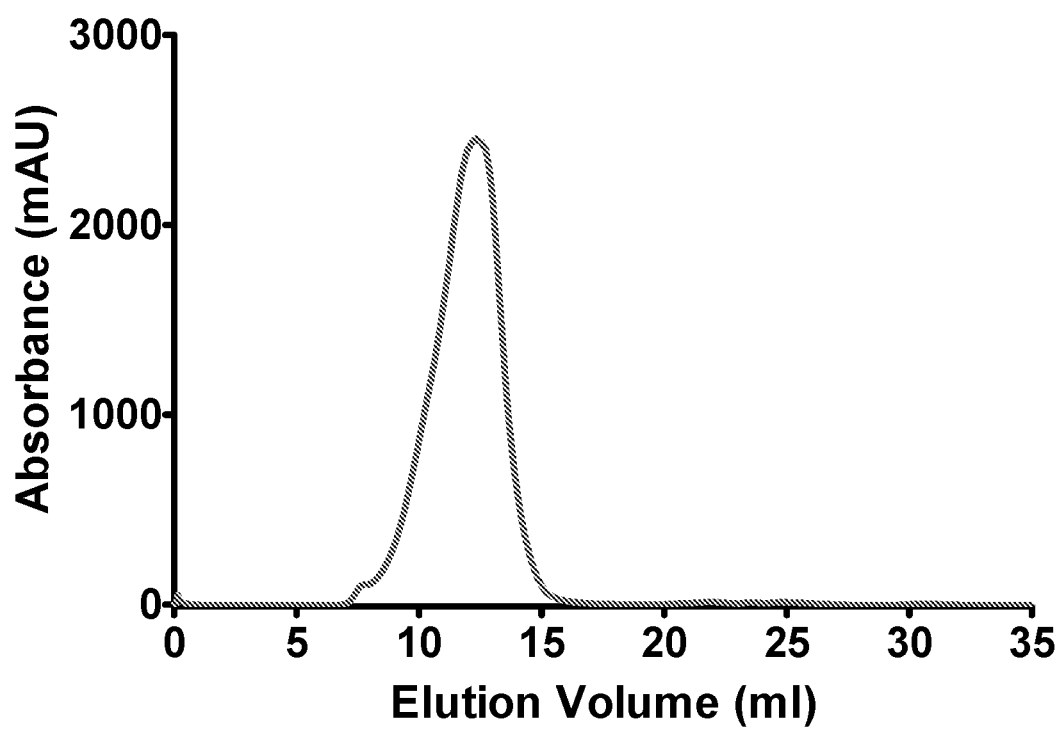
FIG. 3 is a gel filtration chromatograph depicting the uniform elution of mEnv+trimers six days post-PEI transfection of 293T cells in roller bottles (750-ml of supernatant).
Figure 4:
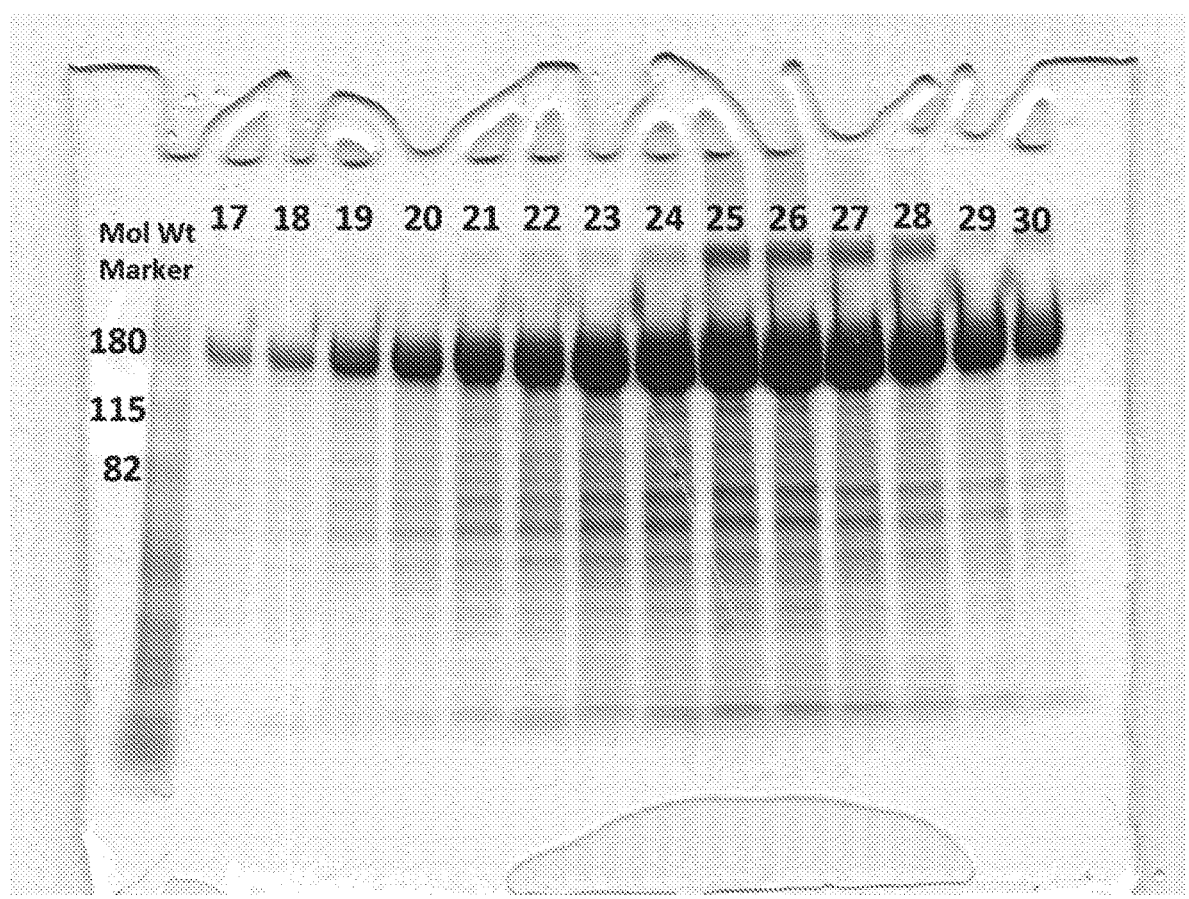
FIG. 4 is an image of a 4-16% gradient SDS-PAGE showing the peak fractions of mEnv+ following gel filtration elution. The final protein yield per purification is approximately 8.44 mg following gel filtration. The final concentration is approximately 5.62 mg/ml.

As noted above, the mEnv+ was expressed in 293T cells and purified following cell lysis and clarification by virtue of a His-tag using a Ni-NTA (Qiagen) column. The collected fractions following imidazole elution were pooled, concentrated, and further purified by gel-filtration chromatography on Superose 6 (GE Healthcare) in a column running buffer containing 25 mM Tris (pH 7.5) and 150 mM NaCl. A chromatography trace of depicting mEnv+ elution from the Superose 6 column is depicted in FIG. 3. The peak fractions (i.e., the fractions obtained under the peak curve in FIG. 3) were then individually analyzed on a 4-15% pre-case SDS-PAGE gel (FIG. 4). The SDS-PAGE gel demonstrates that the gel-filtration purification successfully resulted in the isolation of a homogenous population of mEnv+ polypeptides. As described further herein, the immunogenicity of these stabilized gp140 Env trimers (both homotrimers of mEnv and mEnv+, as well as a combination of mEnv and cEnv homotrimers) was assessed in guinea pigs using a panel of tier 1 isolates from clades A, B, and C.

Example 3. Analysis of Neutralizing Antibody Responses

Preclinical evaluation of candidate Env immunogens is critical for concept testing and for prioritization of vaccine candidates. Luciferase-based virus neutralization assays in TZM.bl cells (Li et al. (2005) J. Virol. 79:10108; Montefiori (2005) Curt Prot. Immunol. Chapter 12: Unit 1211) have been developed as high throughput assay that can be standardized (Montefiori (2009) Methods Mol. Biol. 485:395; Polonis et al. (2008) Virology 375:315). A luciferase reporter gene assay was performed in TZM-bl cells (a genetically engineered cell line that expresses CD4, CXCR4 and CCR5 and contains Tat-inducible Luc and β-Gal reporter genes) based on single round infection with molecularly cloned Env-pseudotyped viruses. This assay resulted in a high success rate in single round infections, increased assay capacity (e.g., a two day assay), increased precision (e.g., accurately measured 50% neutralization), and an improved level of standardization (e.g., a stable cell line). The luciferase reporter gene assay was optimized and validated.

Figures 5A, 5B, 5C:
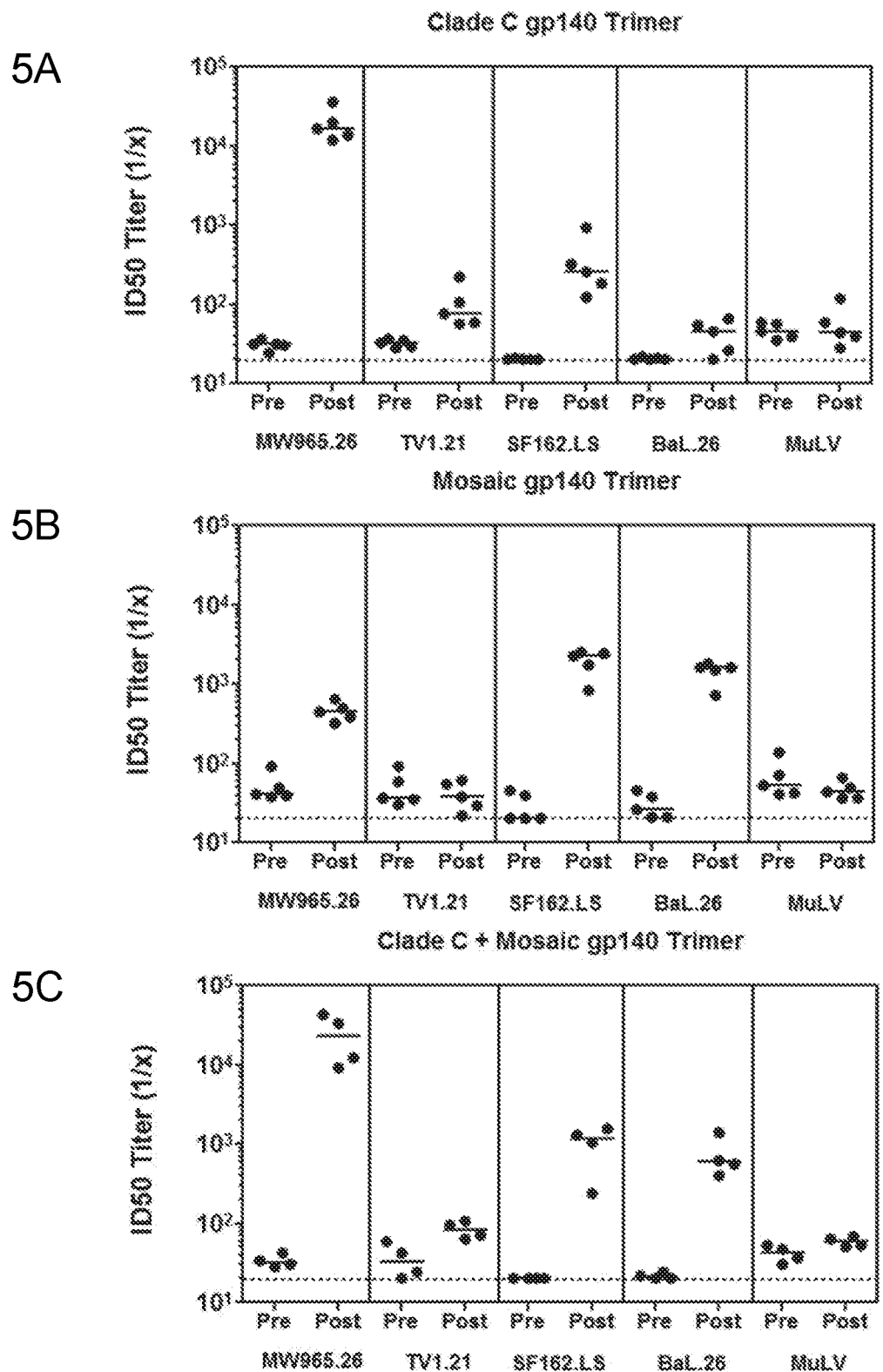
FIG. 5A is a graph showing a quantitative analysis of $ID_{50}$ titer measuring TZM.bl neutralizing antibody responses in guinea pigs pre-vaccination (Pre) and post-vaccination (Post) with clade C gp140 Env (cEnv) homotrimer tested against a multi-clade panel of tier 1 neutralization-sensitive isolates including clade B (SF162.LS and Bal.26) and clade C (MW965.26 and TV1.21) HIV-1 Envelope pseudoviruses, as well as Murine leukemia virus (MuLV) (negative control).
FIG. 5B is a graph showing a quantitative analysis of $ID_{50}$ titer measuring TZM.bl neutralizing antibody responses in guinea pigs pre-vaccination (Pre) and post-vaccination (Post) with mosaic gp140 Env version-1 (mEnv) homotrimer tested against a multi-Glade panel of tier 1 neutralization-sensitive isolates including clade B (SF162.LS and Bal.26) and clade C (MW965.26 and TV1.21) HIV-1 Envelope pseudoviruses, as well as Murine leukemia virus (MuLV) (negative control).
FIG. 5C is a graph showing a quantitative analysis of $ID_{50}$ titer measuring TZM.bl neutralizing antibody responses in guinea pigs pre-vaccination (Pre) and post-vaccination (Post) with both cEnv and mEnv trimers tested against a multi-clade panel of tier 1 neutralization-sensitive isolates including clade B (SF162.LS and Bal.26) and clade C (MW965.26 and TV1.21) HIV-1 Envelope pseudoviruses, as well as Murine leukemia virus (MuLV) (negative control).

To assess the neutralization profile afforded by the stabilized gp140 Env trimers of the invention, TZM.bl assays were performed in which guinea pig sera obtained pre-vaccination (Pre) and four weeks after the third vaccination (Post) with cEnv homotrimers, mEnv homotrimers, or both cEnv and mEnv homotrimers were tested against a multi-clade panel of tier 1 neutralization-sensitive isolates including clade B (SF162.LS and Bal.26), and clade C (MW965.26 and TV1.21) HIV-1 Envelope pseudoviruses and Murine leukemia virus (MuLV) (negative control) (FIGS. 5A-5C).

Figure 6A:
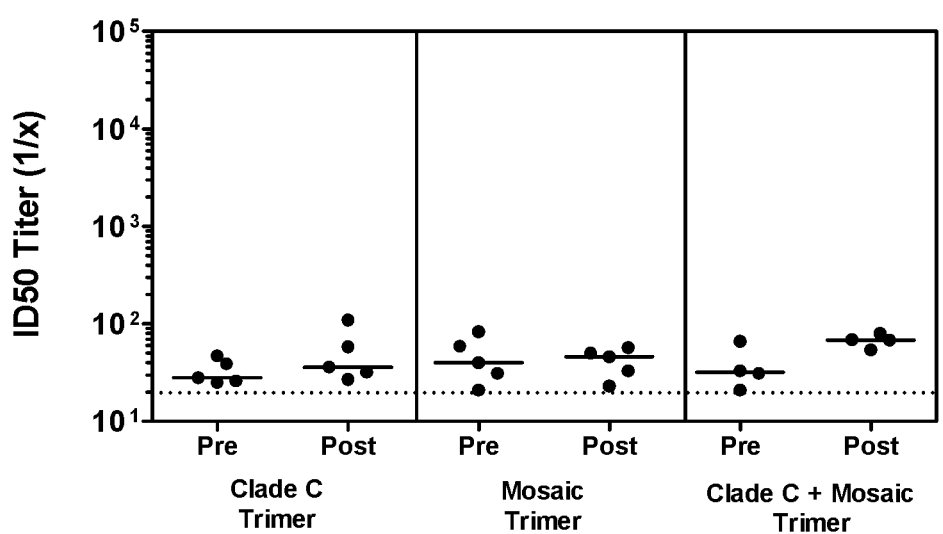
FIG. 6A is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv timers tested against a Tier 1B intermediate neutralization-sensitive clade A HIV-1 Envelope pseudovirus, MS208.A1.
Figure 6B:
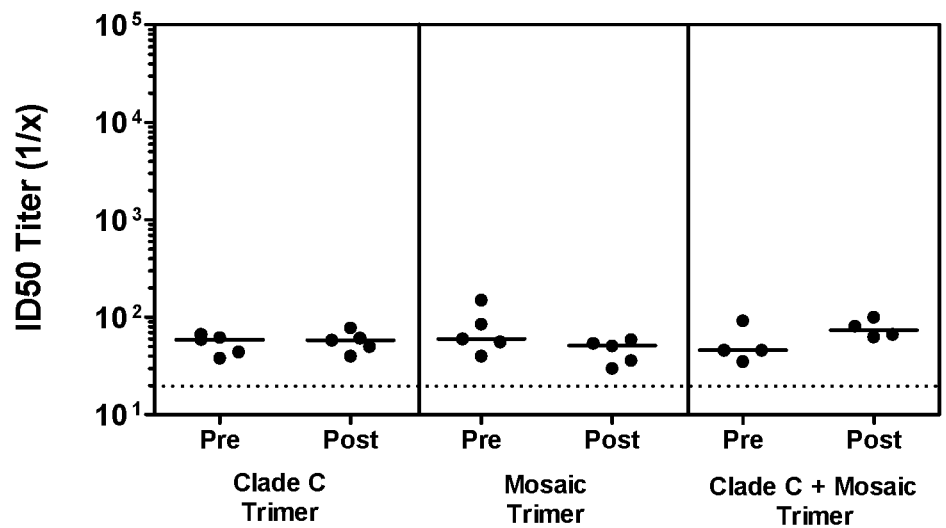
FIG. 6B is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv timers tested against a Tier 1B intermediate neutralization-sensitive clade A HIV-1 Envelope pseudovirus, Q23.17.
Figure 7A:
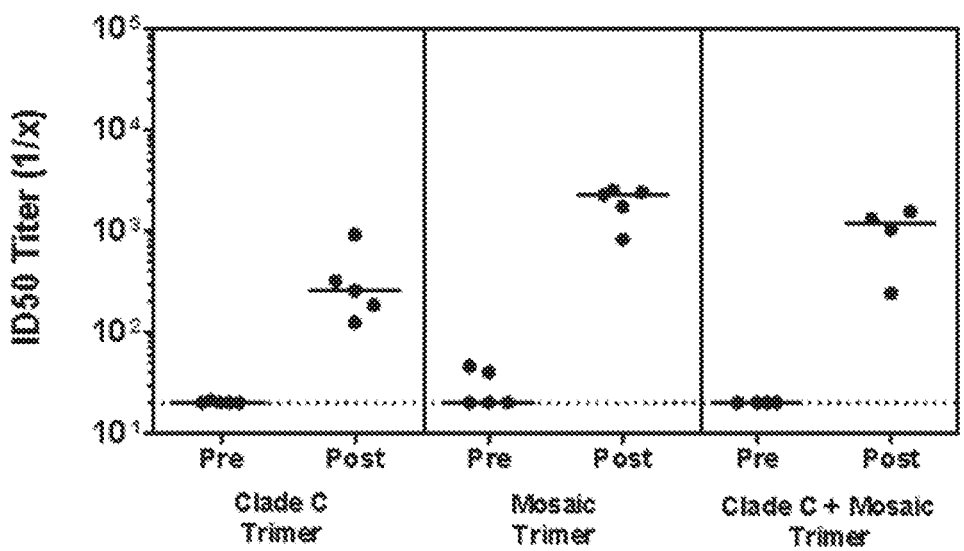
FIG. 7A is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv timers tested against a Tier 1A highly neutralization-sensitive clade B HIV-1 Envelope pseudovirus, SF162.LS.
Figure 7B:
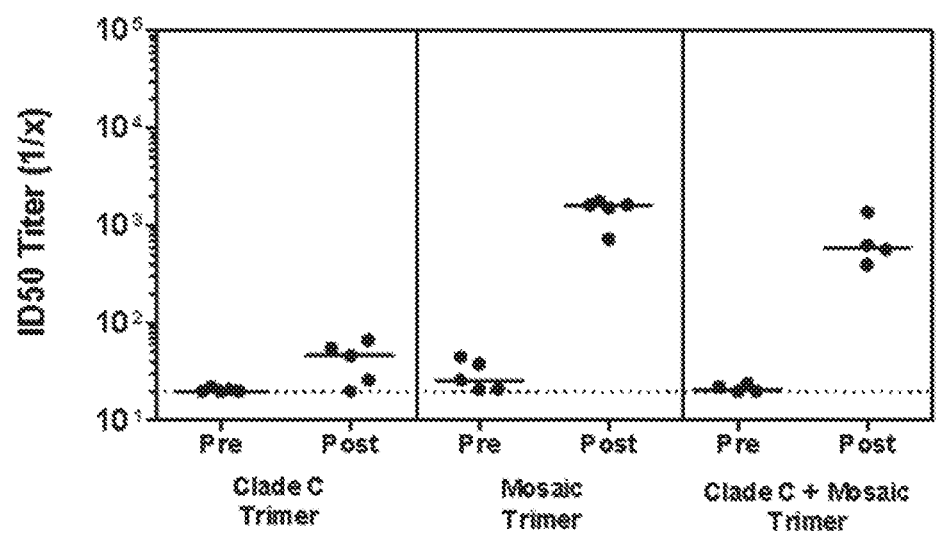
FIG. 7B is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv trimers tested against a Tier 1B intermediate neutralization-sensitive clade B HIV-1 Envelope pseudovirus, BaL.26.
Figure 7C:
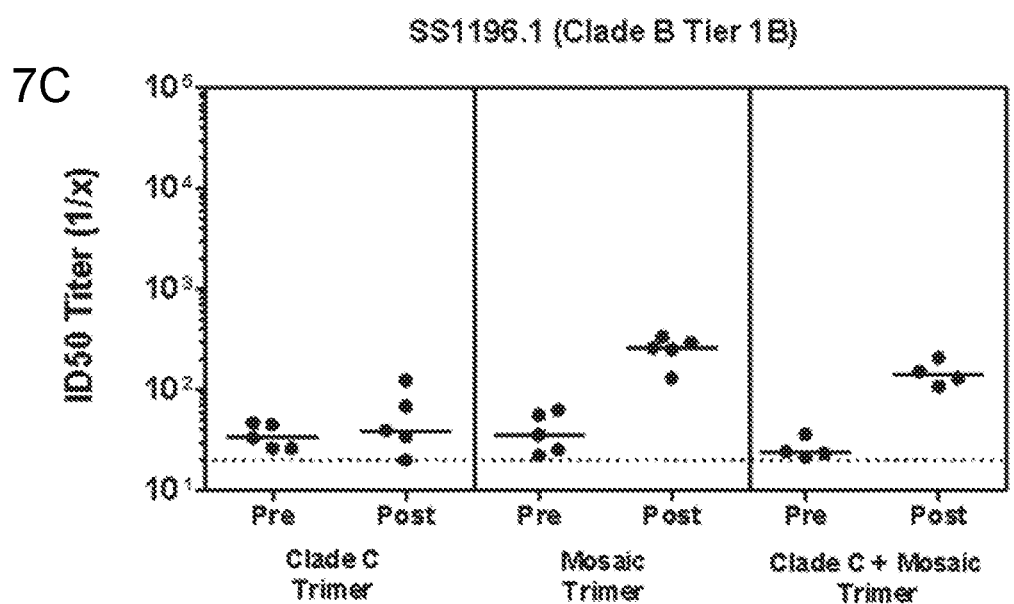
FIG. 7C is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv trimers tested against a Tier 1B intermediate neutralization-sensitive clade B HIV-1 Envelope pseudovirus, SS1196.1.
Figure 7D:
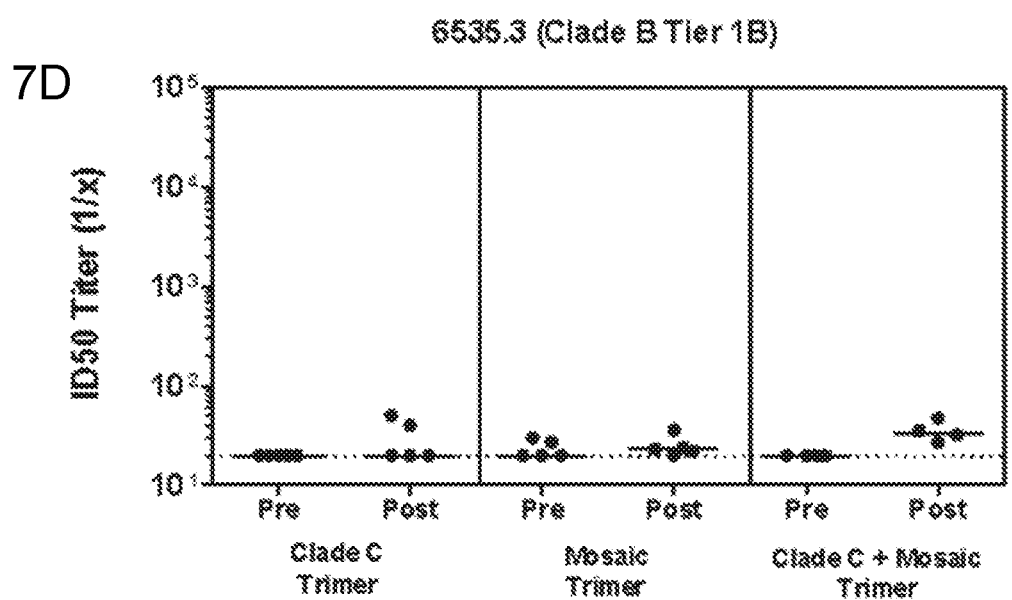
FIG. 7D is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv trimers tested against a Tier 1B intermediate neutralization-sensitive clade B HIV-1 Envelope pseudovirus, 6535.3.
Figure 8A:
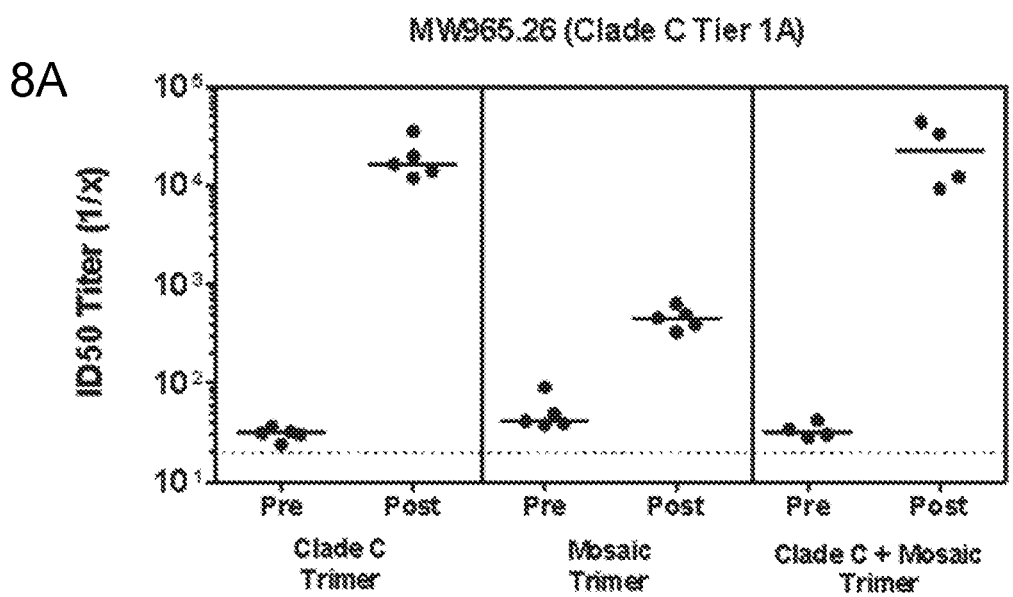
FIG. 8A is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv timers tested against a Tier 1A highly neutralization-sensitive clade C HIV-1 Envelope pseudovirus, MW965.26.
Figure 8B:
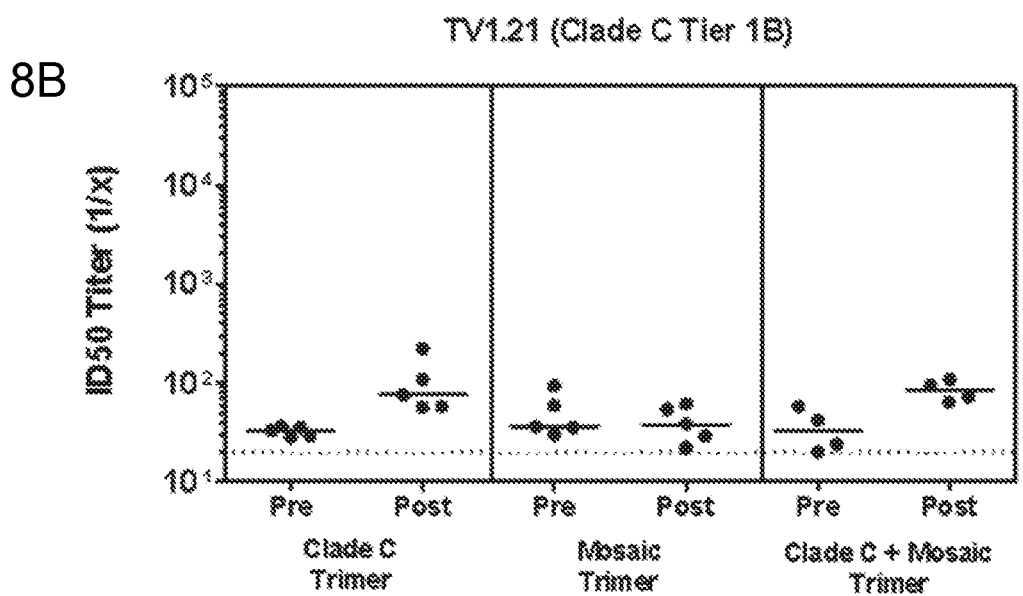
FIG. 8B is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv trimers tested against a Tier 1B intermediate neutralization-sensitive clade C HIV-1 Envelope pseudovirus, TV1.21.
Figure 8C:
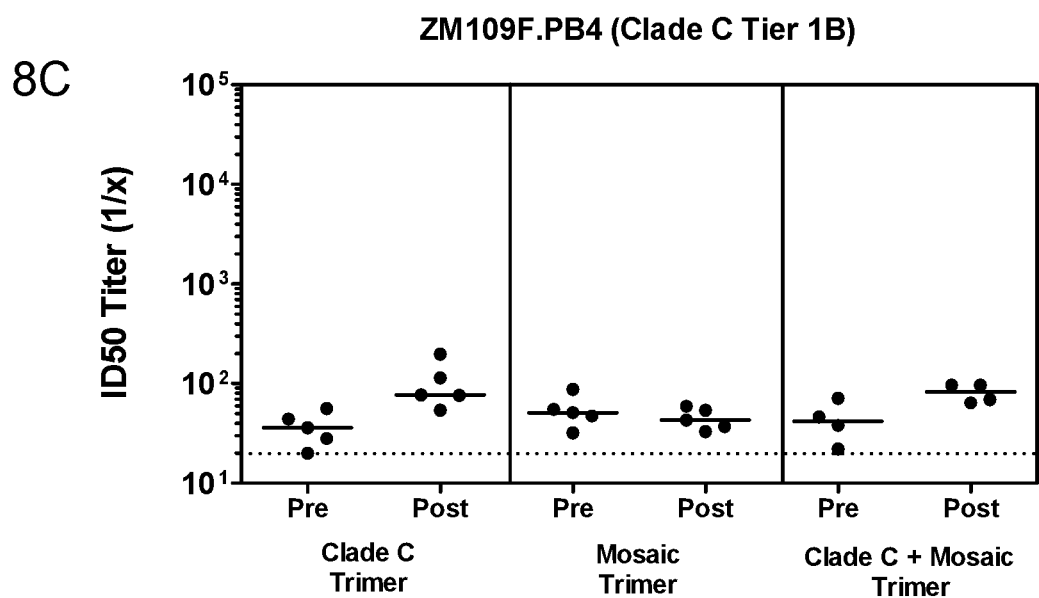
FIG. 8C is a graph showing a quantitative analysis of $ID_{50}$ titer measuring TZM.bl neutralizing antibody responses in guinea pigs pre-vaccination (Pre) and post-vaccination (Post) with cEnv homotrimer, mEnv homotrimer, or both cEnv and mEnv trimers tested against a Tier 1B intermediate neutralization-sensitive clade C HIV-1 Envelope pseudovirus, ZM109F.PB4.
Figure 8D:
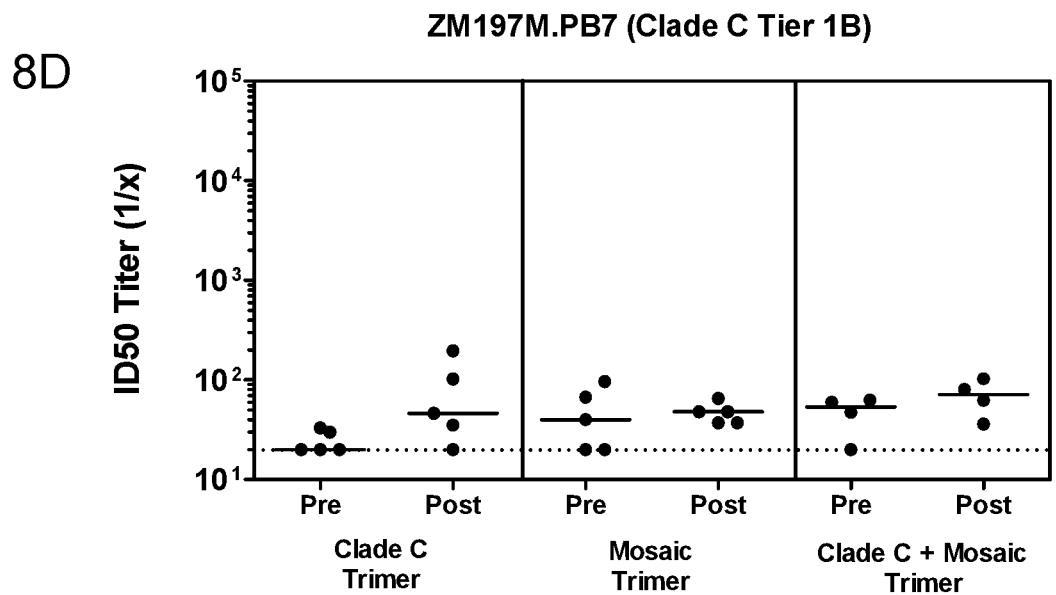
FIG. 8D is a graph showing a quantitative analysis of $ID_{50}$ titer measuring TZM.bl neutralizing antibody responses in guinea pigs pre-vaccination (Pre) and post-vaccination (Post) cEnv homotrimer, mEnv homotrimer, or both cEnv and mEnv trimers tested against a Tier 1B intermediate neutralization-sensitive clade C HIV-1 Envelope pseudovirus, ZM197M.PB7.

TZM.bl assays were also performed in which guinea pig sera obtained pre-vaccination (Pre) and four weeks after the third vaccination (Post) using cEnv homotrimers, mEnv homotrimers, or both cEnv and mEnv heterotrimers were tested against HIV-1 Envelope pseudoviruses of intermediate neutralization-sensitive tier-1 (Tier 1B) clade A isolates (MS208.A1 and Q23.17) (FIGS. 6A-6B), highly neutralization sensitive (Tier 1A) and Tier 1B clade B isolates (SF162.LS, BaL.26, SS1196.1, and 6535.3) (FIGS. 7A-7D), and Tier 1A and Tier 1B clade C isolates (MW965.26, TV1.21, ZM109F.PB4, and ZM197M.PB7) (FIGS. 8A-8D).

Unexpectedly, quantitation of $ID_{50}$ titer data collectively demonstrate that the combination of cEnv and mEnv homotrimers induced neutralizing antibody responses that were superior to either cEnv or mEnv alone. Specifically, the combination of cEnv and mEnv was particularly surprising in terms of expanding the breadth of neutralizing antibody responses induced. Such an expansion of neutralizing antibody breadth has not previously been described and is a major unmet need in the field.

Example 4. Treating or Reducing the Risk of an HIV Infection in a Subject Using the Compositions of the Invention The composition of the invention (e.g., a vaccine of the invention) may be administered to a subject (e.g., a human infected with HIV or at risk of an HIV infection) in a prime-boost vaccination regimen to treat or reduce the risk of an HIV infection in a subject in need thereof. For example, one or more of the compositions of the invention, such as vaccine including mEnv, mEnv+, or cEnv trimers, or combination of mEnv or mEnv+ and cEnv trimers may be administered as a boost. Prior to administration of the boost, the subject is administered as a prime vaccination at least a first vector including a first nucleic acid molecule that encodes a polypeptide having at least 85% amino acid sequence identity (e.g., 86%, 87%, 88%, 89%, 90%, 91%, 92%, 93%, 94%, 95%, 96%, 97%, 98%, or 99% identity) to, or the sequence of, SEQ ID NO: 6, and optionally a second vector including a second nucleic acid molecule that encodes a polypeptide having at least 85% identity (e.g., 86%, 87%, 88%, 89%, 90%, 91%, 92%, 93%, 94%, 95%, 96%, 97%, 98%, or 99% identity) to, or the sequence of, SEQ ID NO: 7.

The composition is preferably administered in an amount that provides a sufficient level of the stabilized gp140 Env trimer gene product (e.g., a level of stabilized gp140 Env trimer that elicits an immune response without undue adverse physiological effects in the subject caused by the immunogenic trimer). If the composition is non-vectored, the polypeptide composition administered may include between approximately 1 µg and 1 mg of stabilized Env trimers, and more preferably between 50 µg and 300 µg of stabilized Env trimers of the invention. Alternatively, the subject may be administered, in the form of a viral vector, at least about $1\times10^3$ viral particles (vp)/dose or between $1\times10^1$ and $1\times10^{14}$ vp/dose, preferably between $1\times10^3$ and $1\times10^{12}$ vp/dose, and more preferably between $1\times10^5$ and $1\times10^{11}$ vp/dose.

Following administration of the composition of the invention in a prime-boost regimen, the patient can be assessed for changes in one or more symptoms or, in particular, the level of HIV titer in the treated subject, and the regimen can be repeated as necessary as described herein above.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

The invention claimed is:

1. An oligomeric protein comprising three gp140 polypeptides, wherein at least one of said gp140 polypeptides comprises an amino acid sequence comprising amino acids 30-724 of SEQ ID NO:2.

2. The oligomeric protein of claim 1, wherein each of said three gp140 polypeptides comprises an amino acid sequence comprising amino acids 30-724 of SEQ ID NO:2.

3. A pharmaceutical composition comprising the oligomeric protein of claim 1 and a pharmaceutically acceptable carrier, excipient, or diluent.

4. The pharmaceutical composition of claim 3, further comprising an adjuvant.

5. The pharmaceutical composition of claim 4, wherein the adjuvant comprises an aluminum salt.

6. The pharmaceutical composition of claim 3, further comprising one or more different oligomeric proteins comprising three gp140 polypeptides.

7. The pharmaceutical composition of claim 6, wherein the one or more different oligomeric proteins comprise three gp140 polypeptides that each comprise an amino acid sequence comprising amino acids 30-708 of SEQ ID NO:3.

8. A pharmaceutical composition comprising the oligomeric protein of claim 2 and a pharmaceutically acceptable carrier, excipient, or diluent.

9. The pharmaceutical composition of claim 8, further comprising an adjuvant.

10. The pharmaceutical composition of claim 9, wherein the adjuvant comprises an aluminum salt.

11. The pharmaceutical composition of claim 8, further comprising one or more different oligomeric proteins comprising three gp140 polypeptides.

12. The pharmaceutical composition of claim 11, wherein the one or more different oligomeric proteins comprise three gp140 polypeptides that each comprise an amino acid sequence comprising amino acids 30-708 of SEQ ID NO:3.

13. A method of inducing an antibody response against HIV in a subject in need thereof, the method comprising administering to the subject a therapeutically effective amount of the pharmaceutical composition of claim 3.

14. The method of claim 13, wherein said subject is infected with HIV and an HIV titer in said subject is decreased after administration of said pharmaceutical composition to said subject.

15. The method of claim 13, wherein the pharmaceutical composition is administered intramuscularly, intradermally, subcutaneously, or mucosally.

16. The method of claim 13, wherein said subject is administered at least one dose of said composition.

17. The method of claim 13, wherein the pharmaceutical composition is administered to said subject as a prime, a boost, or as a prime-boost.

18. An oligomeric protein comprising three gp140 polypeptides, wherein the oligomeric protein is obtained in eukaryotic cell culture by expressing a nucleic acid sequence encoding a gp140 polypeptide comprising the amino acid sequence of SEQ ID NO:2.

19. A pharmaceutical composition comprising the oligomeric protein of claim 18 and a pharmaceutically acceptable carrier, excipient, or diluent.

20. An oligomeric protein comprising three gp140 polypeptides, wherein each of said gp140 polypeptides comprises the amino acid sequence of SEQ ID NO:2.

21. A pharmaceutical composition comprising the oligomeric protein of claim 20 and a pharmaceutically acceptable carrier, excipient, or diluent.

\* \* \* \* \*